(12) United States Patent
Sagehashi et al.

(10) Patent No.: US 11,492,337 B2
(45) Date of Patent: *Nov. 8, 2022

(54) EPOXY COMPOUND, RESIST COMPOSITION, AND PATTERN FORMING PROCESS

(71) Applicant: Shin-Etsu Chemical Co., Ltd., Tokyo (JP)

(72) Inventors: Masayoshi Sagehashi, Joetsu (JP); Ryosuke Taniguchi, Joetsu (JP); Takeru Watanabe, Joetsu (JP); Yoshinori Matsui, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 327 days.

This patent is subject to a terminal disclaimer.

(21) Appl. No.: 16/800,447

(22) Filed: Feb. 25, 2020

(65) Prior Publication Data

US 2020/0283400 A1    Sep. 10, 2020

(30) Foreign Application Priority Data

Mar. 6, 2019    (JP) .............................. JP2019-040260

(51) Int. Cl.
| | | |
|---|---|---|
| *C07D 303/06* | (2006.01) | |
| *G03F 7/004* | (2006.01) | |
| *G03F 7/038* | (2006.01) | |
| *G03F 7/039* | (2006.01) | |
| *C08F 212/08* | (2006.01) | |
| *C08F 220/38* | (2006.01) | |
| *C08L 33/14* | (2006.01) | |

(52) U.S. Cl.
CPC .......... *C07D 303/06* (2013.01); *C08F 212/08* (2013.01); *C08F 220/382* (2020.02); *C08L 33/14* (2013.01); *G03F 7/0045* (2013.01); *G03F 7/0382* (2013.01); *G03F 7/0392* (2013.01)

(58) Field of Classification Search
CPC .......................... C07D 303/06; C07D 303/40
See application file for complete search history.

(56) References Cited

U.S. PATENT DOCUMENTS

| | | | |
|---|---|---|---|
| 6,265,131 B1 | 7/2001 | Chang et al. | |
| 6,492,091 B2 | 12/2002 | Kodama et al. | |
| 6,797,832 B1 * | 9/2004 | Terashima | ............ C07C 69/757 549/546 |
| 7,511,169 B2 | 3/2009 | Ohsawa et al. | |
| 8,173,354 B2 | 5/2012 | Ohsawa et al. | |
| 8,394,570 B2 | 3/2013 | Ohashi et al. | |
| 8,535,869 B2 | 9/2013 | Ohsawa et al. | |
| 8,900,796 B2 | 12/2014 | Ohashi et al. | |
| 2005/0181299 A1 * | 8/2005 | Trefonas | .................. G03F 7/091 430/271.1 |
| 2009/0124776 A1 * | 5/2009 | Takai | ........................ C08F 8/14 525/438 |
| 2017/0131634 A1 * | 5/2017 | Nakagawa | ............... G03F 7/203 |
| 2018/0059542 A1 * | 3/2018 | Aqad | ................... C07D 333/76 |
| 2019/0377261 A1 | 12/2019 | Sakita et al. | |
| 2020/0285152 A1 | 9/2020 | Matsui et al. | |

FOREIGN PATENT DOCUMENTS

| | | |
|---|---|---|
| JP | 3790649 B2 | 6/2006 |
| JP | 2007-145797 A | 6/2007 |
| JP | 4226803 B2 | 2/2009 |
| JP | 2011-16746 A | 1/2011 |
| JP | 5246220 B2 | 7/2013 |
| JP | 2013-209360 A | 10/2013 |
| JP | 5471363 B2 | 4/2014 |
| JP | 2020-149048 A | 9/2020 |
| WO | 2018/180070 A1 | 10/2018 |

OTHER PUBLICATIONS

Office Action dated Dec. 14, 2021, issued in counterpart JP application No. 2019-040260, with English translation. (5 pages).
Lin, "Semiconductor Foundry, Lithography, and Partners", Proc. SPIE, 2002, vol. 4690, xxix. (14 pages).

* cited by examiner

*Primary Examiner* — Anca Eoff

(74) *Attorney, Agent, or Firm* — WHDA, LLP

(57) ABSTRACT

An epoxy compound of formula (1) is provided. A resist composition comprising the epoxy compound is capable of adequately controlling the diffusion length of acid generated from an acid generator without sacrificing sensitivity.

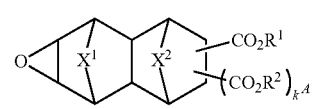

(1)

7 Claims, 2 Drawing Sheets

EPOXY COMPOUND, RESIST COMPOSITION, AND PATTERN FORMING PROCESS

CROSS-REFERENCE TO RELATED APPLICATION

This non-provisional application claims priority under 35 U.S.C. § 119(a) on Patent Application No. 2019-040260 filed in Japan on Mar. 6, 2019, the entire contents of which are hereby incorporated by reference.

TECHNICAL FIELD

This invention relates to an epoxy compound, a resist composition comprising the same, and a pattern forming process using the resist composition.

BACKGROUND ART

To meet the demand for higher integration density and operating speed of LSIs, the effort to reduce the pattern rule is in rapid progress. As the advanced micropatterning technology, the ArF immersion lithography involving exposure through a liquid (typically water) held between a projection lens and a substrate is implemented in a mass scale. Besides, studies are being made on the multi-patterning of ArF lithography and the lithography using extreme ultraviolet (EUV) of wavelength 13.5 m.

The mainstream ArF lithography resist compositions are chemically amplified resist compositions comprising a base polymer and a photoacid generator as essential components. Upon light exposure, the acid generator generates an acid, which reacts with the base polymer. Thus the base polymer undergoes a change only in the exposed region. The exposed rest film is then developed in an alkaline solution or organic solvent, forming a resist pattern.

With the advance of miniaturization, the resist composition used in photolithography is required to improve various properties including resolution and sensitivity. For example an attempt is made to improve the edge roughness (LWR) of line patterns by precisely controlling the diffusion length of acid generated from the acid generator.

For controlling the diffusion length of acid, the first approach is to modify the structure of acid generator to a low acid diffusion design. For example, Patent Document 1 discloses a photoacid generator having a cation structure and an anion structure in a common molecule, which is designed so as to generate an acid of higher molecular weight, thereby rendering the generated acid low diffusive. This design, however, accompanies drawbacks in lithography performance including a lowering of sensitivity, poor solvent solubility of a high molecular weight acid generator, and a lack of solubility in alkaline aqueous solution, suggesting technical difficulty to meet both low acid diffusion and high sensitivity. The second approach is to improve the design of quenchers like amine compounds and salt compounds of low acidity acids (see Patent Documents 2 and 3). The diffusion length of acid can be controlled in proportion to the amount of a quencher added, but a lowering of sensitivity of resist material is inevitable. The approach is not necessarily satisfactory partly became of the demand for the lithography process with higher throughputs.

CITATION LIST

Patent Document 1: JP-A 2011-016746 (U.S. Pat. No. 8,173,354)
Patent Document 2: JP 3790649
Patent Document 3: JP 5471363 (U.S. Pat. No. 8,394,570)

DISCLOSURE OF INVENTION

In the efforts to achieve further miniaturization, both the prior art approaches toward low acid diffusion and high sensitivity originate from structural modifications of acid generators or quenchers. Partly because of the tradeoff relationship of low acid diffusion and high sensitivity mentioned above, these approaches are not necessarily sufficient to satisfy various resist properties including resolution, roughness, and pattern profile.

An object of the invention is to provide a resist composition capable of adequately controlling the diffusion length of acid generated from an acid generator without sacrificing sensitivity, and a patterning process using the resist composition.

The inventors have found that when a specific epoxy compound as an additive is combined with an acid generator to formulate a resist composition, it is possible to adequately control the diffusion length of generated acid and meet both low acid diffusion and high sensitivity at the same time. When the resist composition is applied to ArF, EB and EUV lithography processes, a significant reduction of LWR is achieved. The resist composition is useful in precise micropatterning.

In one aspect, the invention provides an epoxy compound having the formula (1).

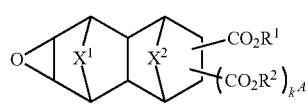

Herein $X^1$ and $X^2$ are each independently —$CH_2$— or —O—, $k^A$ is 0 or 1, $R^1$ and $R^2$ are each independently a $C_4$-$C_{20}$ tertiary hydrocarbon group or a group selected from the following:

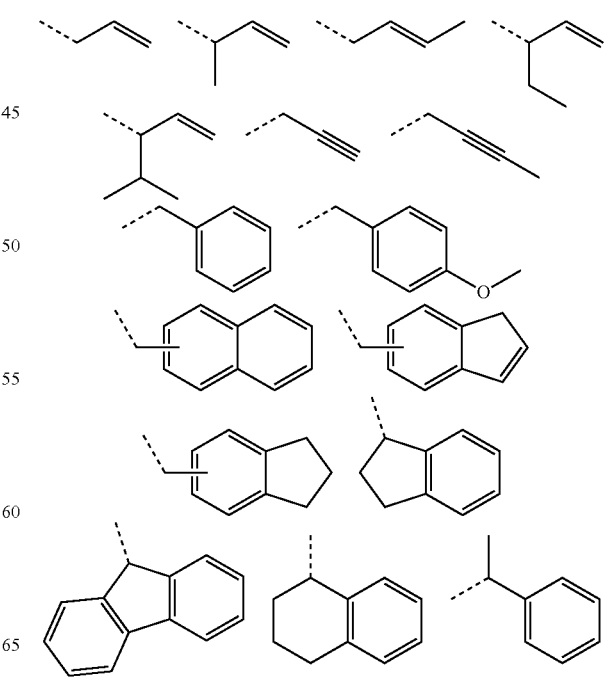

-continued

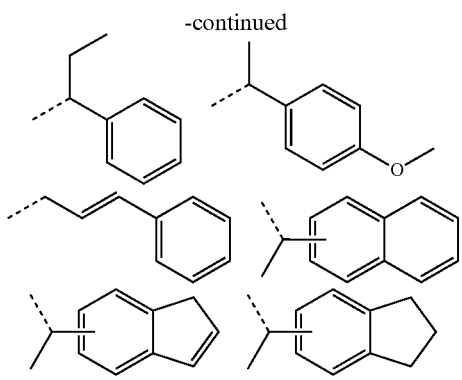

wherein the broken line denotes a valence bond.

In another aspect, the invention provides a resist composition comprising the epoxy compound having formula (1), a base polymer, an acid generator, and an organic solvent. The base polymer comprises recurring units adapted to a polarity switch under the action of acid and recurring units of at least one type selected from the formulae (B) to (E).

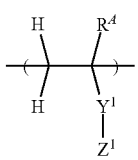 (B)

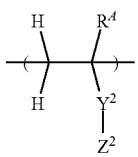 (C)

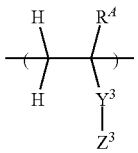 (D)

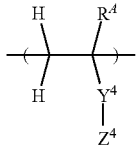 (E)

Herein $R^A$ is hydrogen, fluorine, methyl or trifluoromethyl, $Z^1$ is a $C_1$-$C_{20}$ fluoroalcohol-containing substituent group, $Z^2$ is a $C_1$-$C_{20}$ phenolic hydroxyl-containing substituent group, $Z^3$ is a $C_1$-$C_{20}$ carboxyl-containing substituent group, $Z^4$ is a substituent group containing lactone skeleton, sultone skeleton, carbonate skeleton, cyclic ether skeleton, acid anhydride skeleton, alcoholic hydroxyl moiety, alkoxycarbonyl moiety, sulfonamide moiety, or carbamoyl moiety, $Y^1$ to $Y^4$ are each independently a single bond, methylene, ethylene, phenylene, fluorinated phenylene, naphthylene, —O—$Y^5$—, —C(O)O—$Y^5$—, or —C(=O)—NH—$Y^5$—, $Y^5$ is a $C_1$-$C_6$ alkanediyl, phenylene or naphthylene group, which may contain a carbonyl moiety, ester bond, ether bond or hydroxyl moiety.

In a preferred embodiment, the base polymer further comprises recurring units of at least one type selected from the formulae (F1) to (F4).

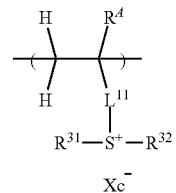 (F1)

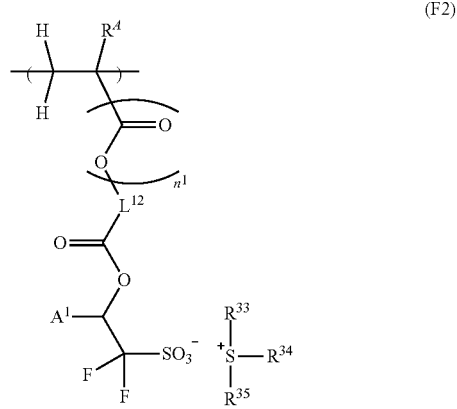 (F2)

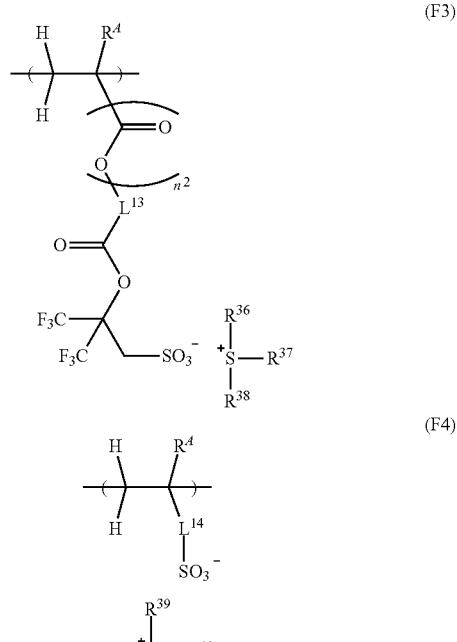 (F3)

(F4)

Herein $R^A$ is hydrogen, fluorine, methyl or trifluoromethyl, $L^{11}$ is a single bond, phenylene, —O-$L^{11A}$-, —C(=O)—O-$L^{11A}$-, or —C(=O)NH-$L^{11A}$-, $L^{11A}$ is a $C_1$-$C_{20}$ alkanediyl, $C_2$-$C_{20}$ alkenediyl, or phenylene group which may contain a heteroatom, $L^{12}$ and $L^{13}$ are each independently a single bond or a $C_1$-$C_{20}$ divalent hydrocarbon group which may contain a heteroatom, $L^{14}$ is a single bond, methylene, ethylene, phenylene, fluorinated phenylene, —O-$L^{14A}$-, —C(=O)—O-$L^{14A}$-, or —C(=O)—NH-$L^{14A}$-, $L^{14A}$ is an optionally substituted phenylene group, $R^{31}$ to $R^{41}$ are each independently a $C_1$-$C_{20}$ monovalent hydrocarbon group which may contain a heteroatom, any two of $L^{11}$, $R^{31}$ and $R^{32}$ may bond together to form a ring with the sulfur atom to which they are attached, any two of $R^{33}$, $R^{34}$ and $R^{35}$, any two of $R^{36}$, $R^{37}$ and $R^{38}$, or any two of $R^{39}$, $R^{40}$ and $R^{41}$ may bond together to form a ring with the sulfur atom to which they are attached, $Xc^-$ is a non-nucleophilic counter ion, $A^1$ is hydrogen or trifluoromethyl, $n^1$ is 0 or 1, $n^1$ is 0 when $L^{12}$ is a single bond, $n^2$ is 0 or 1, $n^2$ is 0 when $L^{13}$ is a single bond.

Also provided is a resist composition comprising the epoxy compound having formula (1), a base polymer, and an organic solvent. The base polymer comprises recurring units adapted to a polarity switch under the action of acid, recurring units of at least one type selected from the formulae (B) to (E), and recurring units of at least one type selected from the formulae (F1) to (F4).

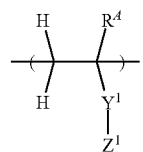
(B)

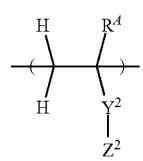
(C)

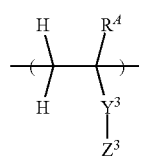
(D)

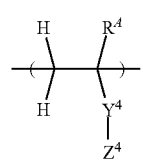
(E)

Herein $R^A$, $Z^1$ to $Z^4$, $Y^1$ to $Y^4$ are as defined above.

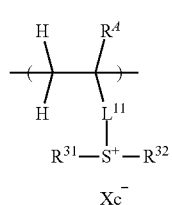
(F1)

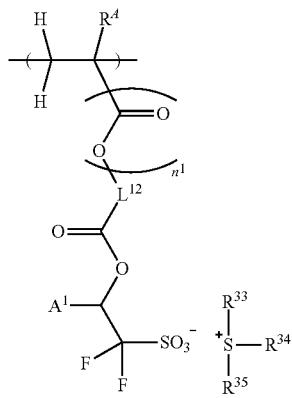
(F2)

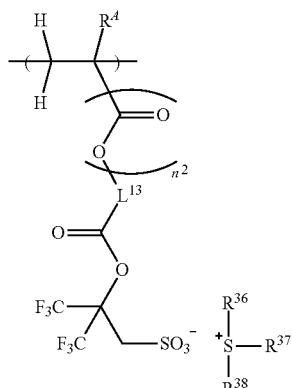
(F3)

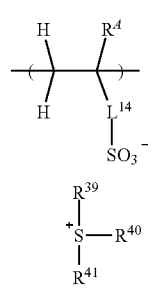
(F4)

Herein $R^A$, $L^{11}$ to $L^{14}$, $R^{31}$ to $R^{41}$, $Xc^-$, $A^1$, $n^1$, and $n^2$ are as defined above.

In a further aspect, the invention provides a pattern forming process comprising the steps of applying the resist composition defined above to form a resist film on a substrate, exposing the resist film to high-energy radiation, and developing the exposed resist film in a developer.

In one preferred embodiment, an alkaline aqueous solution is used as the developer in the developing step to form a positive pattern wherein the exposed region of film is dissolved and the unexposed region of film is not dissolved.

In another preferred embodiment, an organic solvent is used as the developer in the developing step to form a negative pattern wherein the unexposed region of film is dissolved and the exposed region of film is not dissolved.

Advantageous Effects of Invention

When the epoxy compound is used in resist compositions adapted for ArF, EB and EUV lithography processes, it is possible to adequately control the diffusion length of an acid generated from an acid generator. Then both low acid diffusion and high sensitivity are met at the same time, and a significant improvement in LWR is achieved.

DESCRIPTION OF PREFERRED EMBODIMENTS

Figure 1:
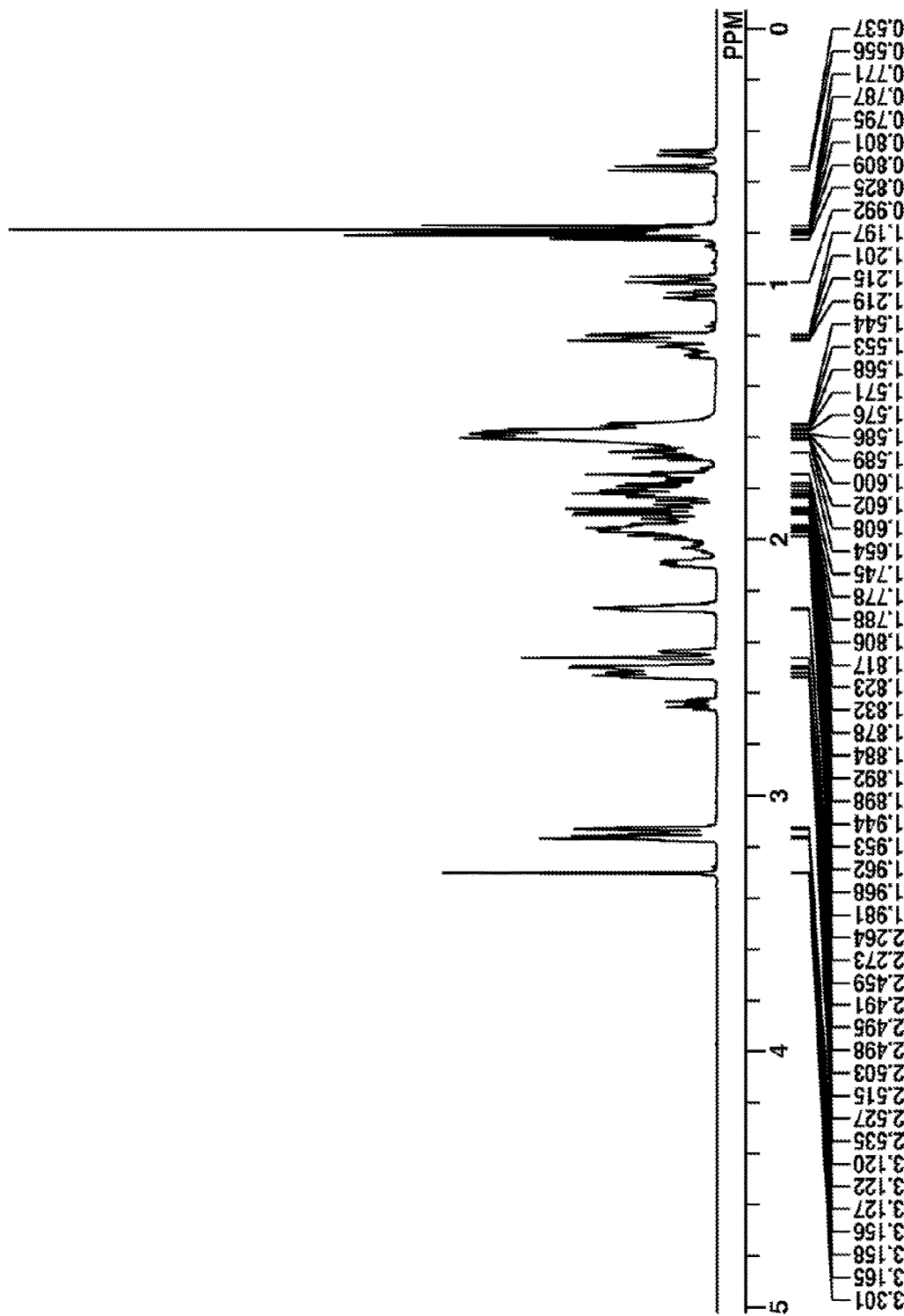
FIG. 1 is a diagram showing the $^1$H-NMR spectrum of epoxy compound EP-1 obtained in Example 1-1.

As used herein, the singular forms "a," "an" and "the" include plural referents unless the context clearly dictates otherwise. The notation ($C_n$-$C_m$) means a group containing from n to m carbon atoms per group. In chemical formulae, the broken line denotes a valence bond. Me stands for methyl, nBu for n-butyl, tBu for tert-butyl, Ac for acetyl, and Ph for phenyl.

The abbreviations and acronyms have the following meaning.
EB: electron beam
EUV: extreme ultraviolet
Mw: weight average molecular weight
Mn: number average molecular weight
Mw/Mn: molecular weight dispersity
GPC: gel permeation chromatography
PEB: post-exposure bake
PAG: photoacid generator
LWR line width roughness
CDU: critical dimension uniformity It is understood that for some structures represented by chemical formulae, there can exist enantiomers and diastereomers. In any cases, a single formula collectively represents all such stereoisomers unless otherwise stated. The stereoisomers may be used alone or in admixture.

Epoxy Compound

One embodiment of the invention is an epoxy compound having the formula (1).

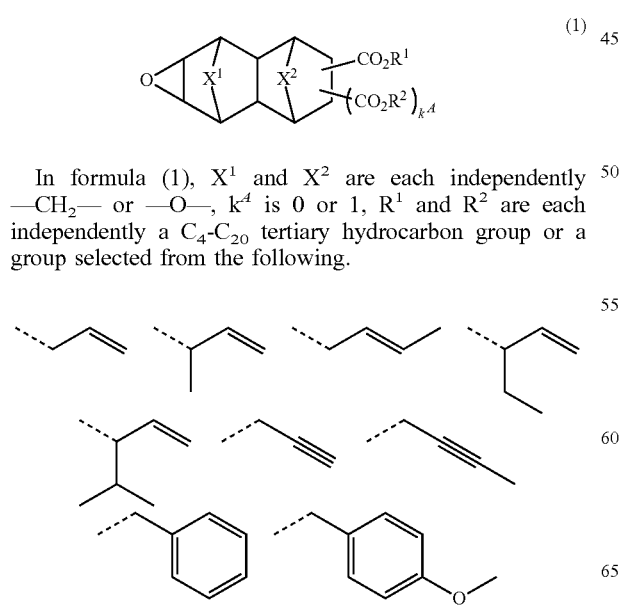

In formula (1), $X^1$ and $X^2$ are each independently —$CH_2$— or —O—, $k^4$ is 0 or 1, $R^1$ and $R^2$ are each independently a $C_4$-$C_{20}$ tertiary hydrocarbon group or a group selected from the following.

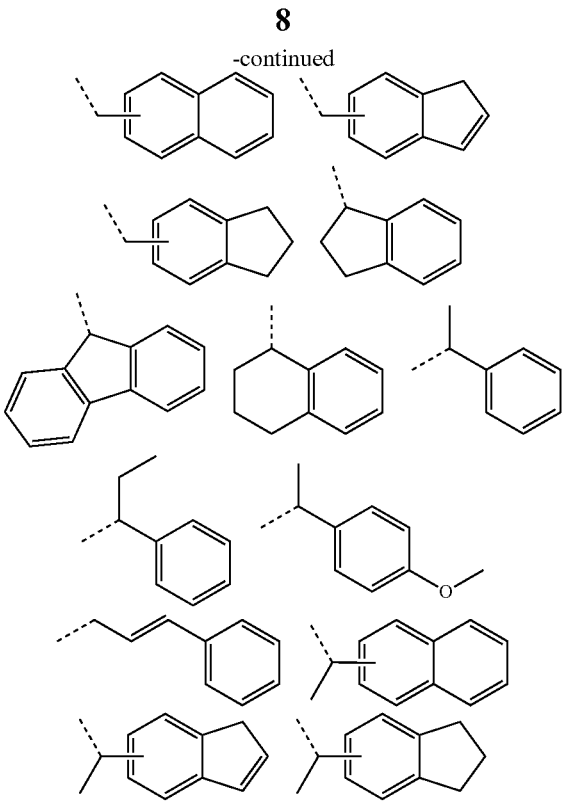

The $C_4$-$C_{20}$ tertiary hydrocarbon group is a group wherein the carbon atom attaching to the ester oxygen atom is a tertiary carbon atom. The tertiary hydrocarbon group may be either saturated or unsaturated and may contain an aromatic moiety therein. Exemplary of the $C_4$-$C_{20}$ tertiary hydrocarbon group are groups having the formulae (L3) to (L9) which will be shown later.

Examples of the epoxy compound having formula (1) are given below, but not limited thereto. Herein $X^1$ and $X^2$ are as defined above.

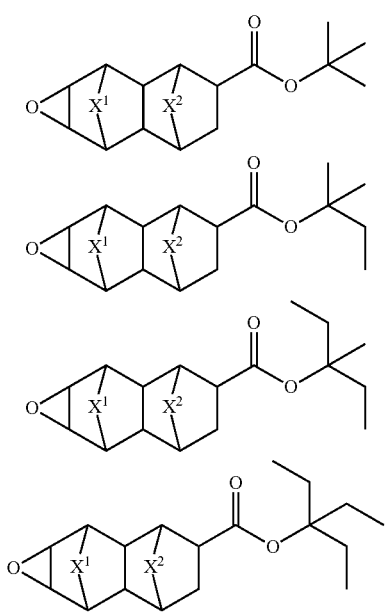

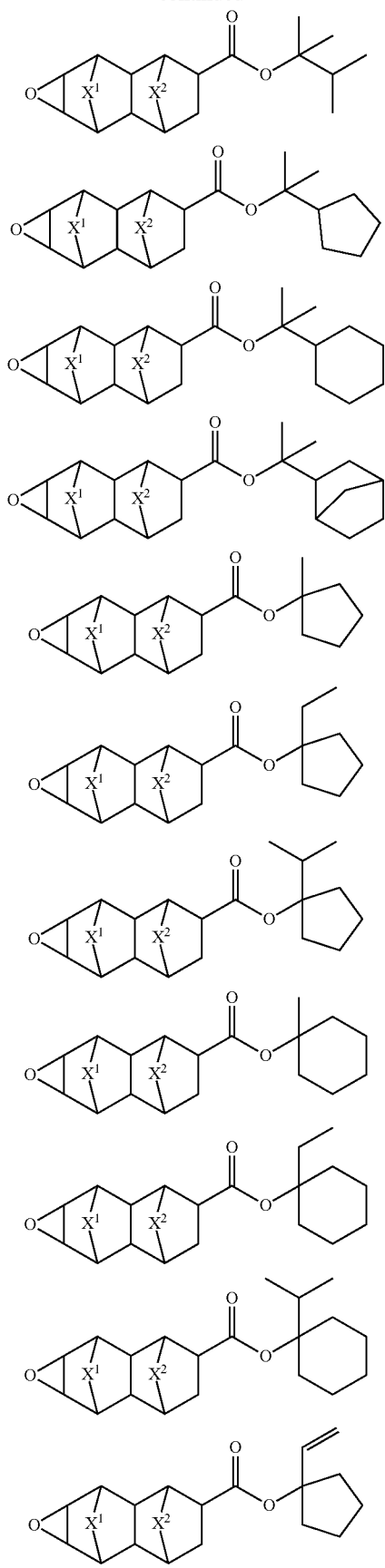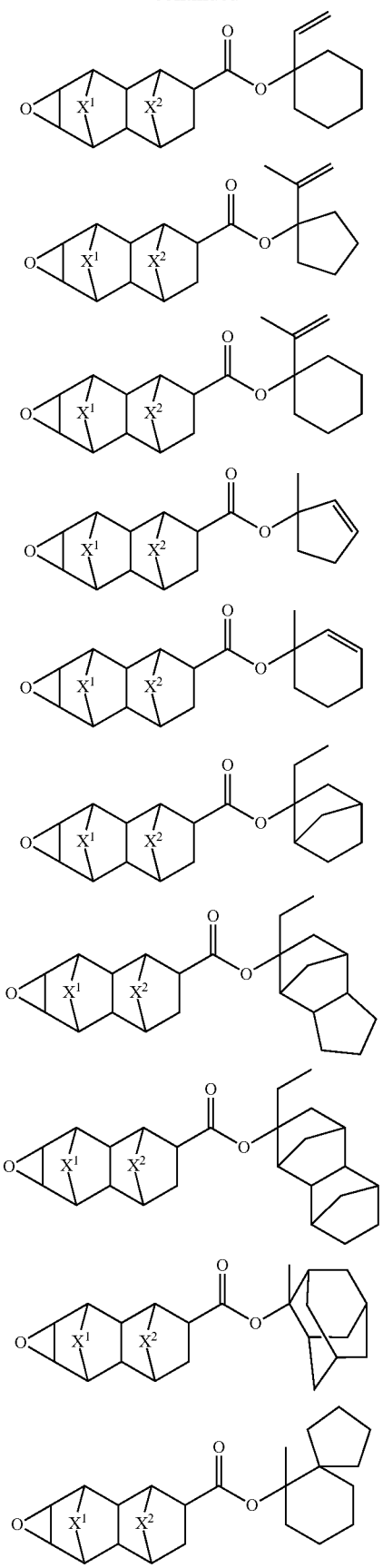

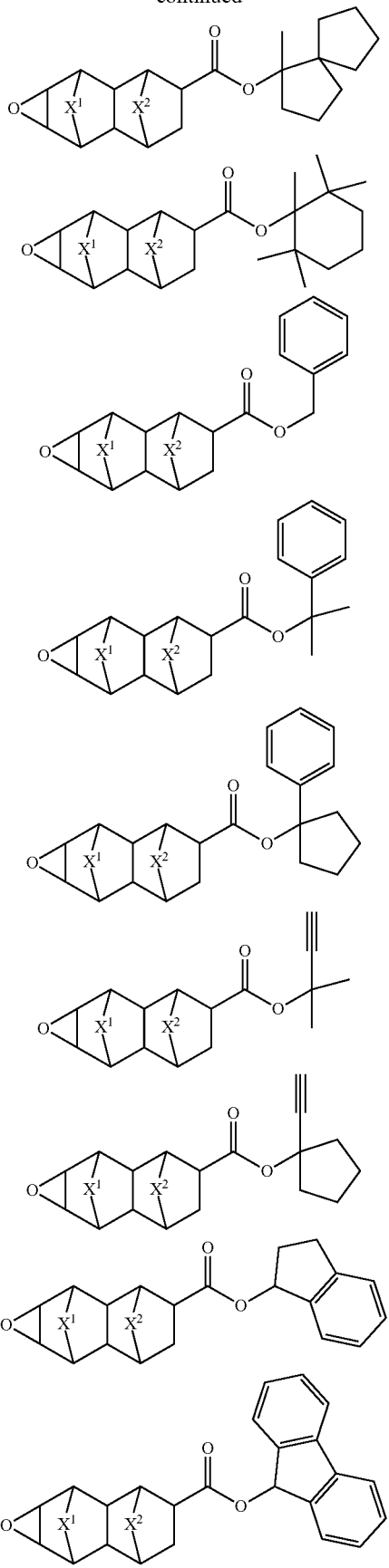

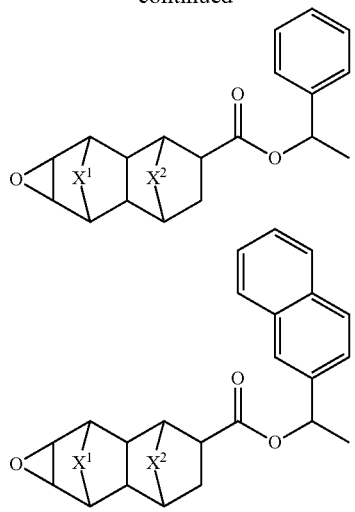

The epoxy compound may be obtained, for example, by effecting oxidation reaction on an olefin compound (pr-1) as a precursor, which can be synthesized by any well-known methods, to convert the double bond moiety to epoxide. This reaction process is shown by the following scheme, but the preparation of the epoxy compound is not limited to this route.

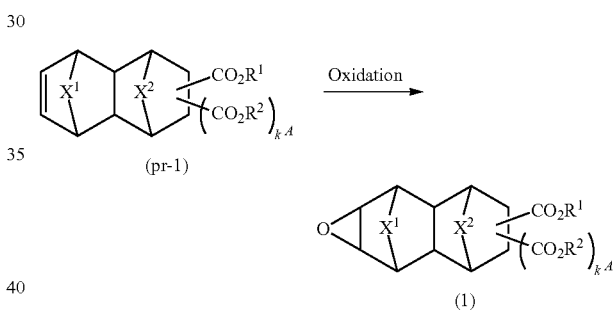

Herein $X^1$, $X^2$, $R^1$, $R^2$, and $k^A$ are as defined above.

The method for oxidizing olefin compound (pr-1) or precursor may be selected optimum from well-known oxidation methods including reactions with peroxides, for example, aqueous hydrogen peroxide, and organic carboxylic acid peroxides such as performic acid, peracetic acid, and m-chloroperbenzoic acid and catalytic reactions in the presence of transition metal oxides which are combinations of transition metal catalysts with the foregoing peroxides. Of these, aqueous hydrogen peroxide and organic carboxylic acid peroxides are preferably used because reaction runs under mild conditions at room temperature to about 40° C. without a need for complex steps.

It is desirable from the standpoint of yield that the reaction time is determined so as to drive the oxidation reaction to completion by monitoring the reaction process by gas chromatography (GC) or silica gel thin layer chromatography (LC). Usually, the reaction time is about 1 to about 72 hours. From the reaction mixture, the epoxy compound is recovered through an ordinary aqueous workup. If necessary, it may be purified by a standard technique such as distillation, chromatography or recrystallization.

Resist Composition

A second embodiment of the invention is a resist composition comprising the epoxy compound having formula (1), a base polymer, an acid generator, and an organic solvent. The acid generator may be a polymer-bound acid generator (i.e., acid generator is integrated with base polymer) or an acid generator of addition type (i.e., separate from base polymer). In the case of polymer-bound acid generator, the base polymer has both a base polymer function and an acid generator function.

The epoxy compound having formula (1) functions as a sensitivity regulator in a resist composition. In general, the epoxy compound is effective for suppressing the diffusion of acid generated from the acid generator upon light exposure, though its action is moderate as compared with amines and weak acid salt compounds used as the so-called quencher to strong acid. The inventive epoxy compound is characterized by a fused ring skeleton of 4 rings excluding the epoxy ring and an acid labile alkoxycarbonyl group. The use of the inventive epoxy compound as an additive in the resist composition enables to suppress otherwise excessive acid diffusion to an appropriate level, contributing to an improvement in contrast between the exposed and unexposed regions of a line-and-space pattern and succeeding in forming a line-and-space pattern with minimal LWR. It is believed that the robust quadri-cyclic fused ring skeleton contributes to adjustment of the mobility or kinematic behavior of the epoxy compound itself in the resist film during PEB. As a consequence, the reactivity or activity of the epoxy compound relative to the acid molecule is made adequate. Further, the epoxy compound contains an acid labile group structure, which gets involved in the excessively diffusive action of the generated acid molecule which is difficult to control completely with the epoxy group alone. This restrains the undesirable acid-catalyzed elimination reaction of acid labile groups on the base polymer in the unexposed region. Once the action of acid is restrained, the epoxy compound generates a highly polar carboxylic acid group, and turns soluble in alkaline aqueous solution, for example, contributing to an improvement in the dissolution contrast (of soluble/insoluble) at the boundary between exposed and unexposed regions during development.

In the resist composition, the epoxy compound is preferably used in an amount of 0.001 to 10 parts by weight, more preferably 0.01 to 5 parts by weight per 80 parts by weight of the base polymer. The epoxy compound may be used alone or in admixture. It is also expected that when the epoxy compound is used in combination with quenchers such as amines or onium salts of weak acids, the lithography performance of a resist composition is further improved.

Base Polymer

The base polymer used herein comprises recurring units adapted to undergo a polarity switch under the action of acid, referred to as recurring units (A), hereinafter.

Examples of the monomer from which recurring units (A) are derived include compounds having the formulae (A-1) and (A-2).

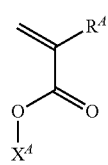
(A-1)

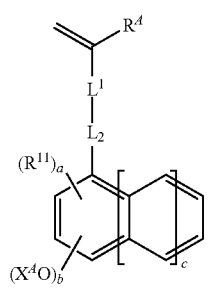
(A-2)

In formulae (A-1) and (A-2), $R^A$ is hydrogen, fluorine, methyl or trifluoromethyl. $X^A$ is an acid labile group. $R^{11}$ is each independently hydrogen or a $C_1$-$C_6$ alkyl group which may contain an ether bond or carbonyl moiety. $L^1$ is a single bond, carbonyloxy group or amide group. $L^2$ is a single bond or a $C_1$-$C_7$ alkanediyl group which may contain an ether bond or carbonyl moiety. The subscript "a" is an integer meeting: a≤5+2c−b, b is an integer of 1 to 5, and c is an integer of 0 to 2.

In formula (A-2), examples of the $C_1$-$C_6$ alkyl group which may contain an ether bond or carbonyl moiety, represented by $R^{11}$, include, but are not limited to, methyl, ethyl, propyl, isopropyl, n-butyl, sec-butyl, tert-butyl, pentyl, hexyl, heptyl, octyl, cyclopentyl, and cyclohexyl, as well as the groups shown below.

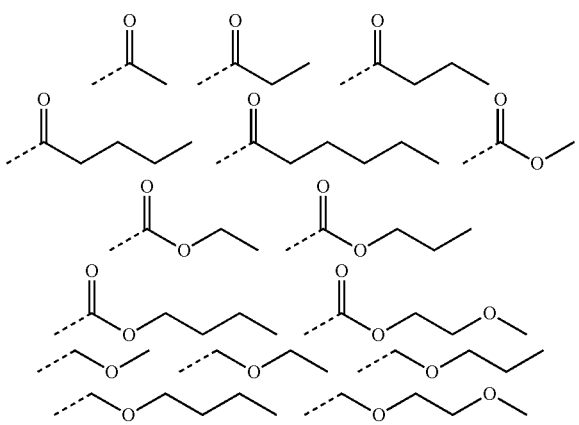

In formula (A-2), examples of the $C_1$-$C_7$ alkanediyl group which may contain an ether bond or carbonyl moiety, represented by $L^2$, include, but are not limited to, methylene, ethylene, propane-1,3-diyl, butane-1,4-diyl, pentane-1,5-diyl, hexane-1,6-diyl, and heptane-1,7-diyl, as well as the groups shown below.

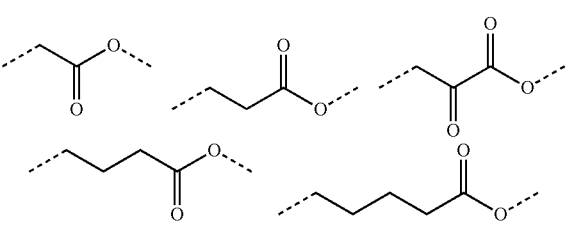

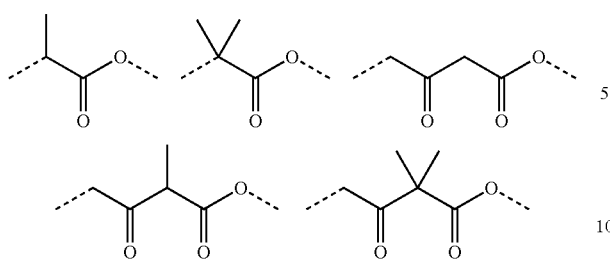

A polymer comprising recurring units derived from a monomer having formula (A-1) or (A-2) is decomposed under the action of acid to generate a carboxyl or phenolic hydroxyl group so that it may turn alkali soluble. The acid labile group $X^A$ may be selected from a variety of such groups. Examples of the acid labile group are groups of the following to formulae (L1) to (L9), tertiary alkyl groups of 4 to 20 carbon atoms, preferably 4 to 15 carbon atoms, trialkylsilyl groups in which each alkyl moiety has 1 to 6 carbon atoms, and $C_4$-$C_{20}$ oxoalkyl groups.

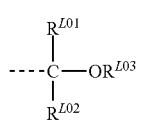 (L1)

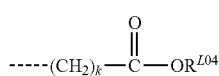 (L2)

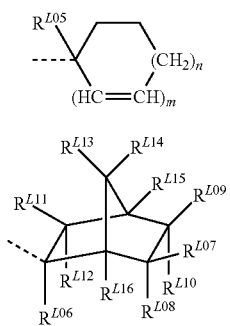 (L3)

(L4)

(L5)

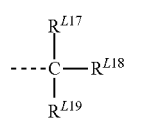 (L6)

(L7)

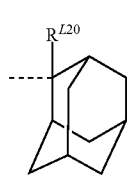

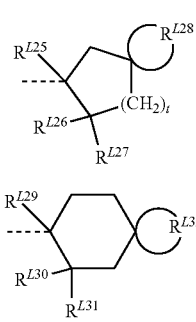 (L8)

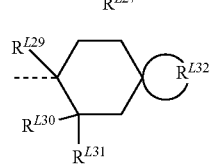 (L9)

In formula (L1), $R^{L01}$ and $R^{L02}$ are each independently hydrogen or a $C_1$-$C_{18}$, preferably $C_1$-$C_{10}$ alkyl group. The alkyl group may be straight, branched or cyclic, and examples thereof include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl.

In formula (L1), $R^{L03}$ is a $C_1$-$C_{18}$, preferably $C_1$-$C_{10}$ monovalent hydrocarbon group which may contain a heteroatom. Suitable heteroatoms include oxygen, nitrogen, and sulfur. Examples of the monovalent hydrocarbon group include straight, branched or cyclic alkyl groups, substituted forms of the alkyl groups in which same hydrogen is substituted by hydroxyl, alkoxy, oxo, amino, alkylamino or the like, and substituted forms of the alkyl groups in which some carbon is replaced by a moiety containing a heteroatom such as oxygen. Suitable alkyl groups are as exemplified for $R^{L01}$ and $R^{L02}$. Exemplary substituted alkyl groups are illustrated below.

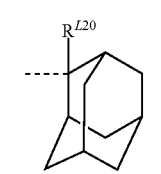

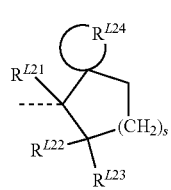

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. A ring-forming combination of $R^{L01}$, $R^{L02}$, and $R^{L03}$ is a $C_1$-$C_{18}$, preferably $C_1$-$C_{10}$ straight or branched alkanediyl group.

In formula (L2), $R^{L04}$ is a $C_4$-$C_{20}$, preferably $C_4$-$C_{15}$ tertiary alkyl group, a trialkylsilyl group in which each alkyl moiety has 1 to 6 carbon atoms, a $C_4$-$C_{20}$ oxoalkyl group, or a group of formula (L1), and k is an integer of 0 to 6.

Suitable tertiary alkyl groups include tert-butyl, tert-pentyl, 1,1-diethylpropyl, 2-cyclopentylpropan-2-yl, 2-cyclohexylpropan-2-yl, 2-bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Suitable trialkylsilyl groups include trimethylsilyl, triethylsilyl, and dimethyl-tert-butylsilyl. Suitable oxoalkyl groups include 3-oxocyclohexyl, 4-methyl-2-oxooxan-4-yl, and 5-methyl-2-oxooxolan-5-yl.

In formula (L3), $R^{L05}$ is a $C_1$-$C_8$ alkyl group which may contain a heteroatom or a $C_6$-$C_{20}$ aryl group which may contain a heteroatom. The alkyl group may be straight, branched or cyclic and examples thereof include methyl, ethyl, propyl, isopropyl, n-butyl, sec-butyl, tert-butyl, tert-pentyl, n-pentyl, n-hexyl, cyclopentyl, and cyclohexyl, and substituted forms of the foregoing in which some hydrogen is substituted by hydroxyl, alkoxy, carboxyl, alkoxycarbonyl, oxo, amino, alkylamino, cyano, mercapto, alkylthio, sulfo or the like. Exemplary aryl groups include phenyl, methylphenyl, naphthyl, anthryl, phenanthryl, and pyrenyl. In formula (L3), m is or 1, n is an integer of 0 to 3, and 2 m+n is equal to 2 or 3.

In formula (L4), $R^{L06}$ is a $C_1$-$C_{10}$ alkyl group which may contain a heteroatom or a $C_6$-$C_{20}$ aryl group which may contain a heteroatom. Examples of alkyl and aryl groups are as exemplified for $R^{L05}$.

In formula (L4), $R^{L07}$ to $R^{L16}$ are each independently hydrogen or a $C_1$-$C_{15}$ monovalent hydrocarbon group. The monovalent hydrocarbon group may be straight, branched or cyclic and examples thereof include straight, branched or cyclic alkyl groups such as methyl, ethyl, propyl, isopropyl, n-butyl, sec-butyl, tert-butyl, tert-pentyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen is substituted by hydroxyl, alkoxy, carboxyl, alkoxycarbonyl, oxo, amino, alkylamino, cyano, mercapto, alkylthio, sulfo or the like. Alternatively, a pair of $R^{L07}$ to $R^{L16}$ (e.g., $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, or $R^{L13}$ and $R^{L14}$) may bond together to form a ring with the carbon atom to which they are attached. A ring-forming combination of $R^{L07}$ to $R^{L16}$ is a $C_1$-$C_{15}$ divalent hydrocarbon group, examples of which are those exemplified above for the monovalent hydrocarbon groups, with one hydrogen atom being eliminated. Also a pair of $R^{L07}$ to $R^{L16}$ (e.g., $R^{L07}$ and $R^{L09}$, $R^{L09}$ and $R^{L15}$, or $R^{L13}$ and $R^{L15}$) which are attached to vicinal carbon atoms may bond together directly to form a double bond.

In formula (L5), $R^{L17}$ to $R^{L19}$ are each independently a $C_1$-$C_{15}$ alkyl group. The alkyl group may be straight, branched or cyclic and examples thereof include methyl, ethyl, propyl, isopropyl, n-butyl, sec-butyl, tert-buty, cyclopentyl, cyclohexyl, 2-ethylhexyl, n-octyl, 1-adamantyl and 2-adamantyl.

In formula (L6), $R^{L20}$ is a $C_1$-$C_{10}$ alkyl group which may contain a heteroatom or $C_6$-$C_{20}$ aryl group which may contain a heteroatom. Examples of the alkyl and aryl groups are as exemplified for $R^{L05}$.

In formula (L7), $R^{L21}$ is a $C_1$-$C_{10}$ alkyl group which may contain a heteroatom or a $C_6$-$C_{20}$ aryl group which may contain a heteroatom. Examples the alkyl and aryl groups are as exemplified for $R^{L05}$. $R^{L22}$ and $R^{L23}$ are each independently hydrogen or a $C_1$-$C_{10}$ monovalent hydrocarbon group. The monovalent hydrocarbon group may be straight, branched or cyclic, and examples thereof are as exemplified for $R^{L07}$ to $R^{L16}$. $R^{L22}$ and $R^{L23}$ may bond together to form a ring with the carbon atom to which they are attached, and the ring is a substituted or unsubstituted cyclopentane or cyclohexane ring. $R^{L24}$ is a divalent group which forms a substituted or unsubstituted cyclopentane, cyclohexane or norbornane ring with the carbon atom to which it is attached. In formula (L7), s is 1 or 2.

In formula (L8), $R^{L25}$ is a $C_1$-$C_{10}$ alkyl group which may contain a heteroatom or a $C_6$-$C_{20}$ aryl group which may contain a heteroatom. Examples of the alkyl ad aryl groups are as exemplified for $R^{L05}$. $R^{L26}$ and $R^{L27}$ are each independently hydrogen or a $C_1$-$C_{10}$ monovalent hydrocarbon group. The monovalent hydrocarbon group may be straight, branched or cyclic and examples thereof are as exemplified for $R^{L07}$ to $R^{L16}$. $R^{L26}$ and $R^{L27}$ may bond together to form a ring with the carbon atom to which they are attached, and the ring is a substituted or unsubstituted cyclopentane or cyclohexane ring. $R^{L28}$ is a divalent group which forms a substituted or unsubstituted cyclopentane, cyclohexane or norbornane ring with the carbon atom to which it is attached. In formula (L8), t is 1 or 2.

In formula (L9), $R^{L29}$ is a $C_1$-$C_{10}$ alkyl group which may contain a heteroatom or a $C_6$-$C_{20}$ aryl group which may contain a heteroatom. Examples of the alkyl and aryl groups are as exemplified for $R^{L05}$. $R^{L30}$ and $R^{L31}$ are each independently hydrogen or a $C_1$-$C_{10}$ monovalent hydrocarbon group. The monovalent hydrocarbon group may be straight, branched or cyclic and examples thereof are as exemplified for $R^{L07}$ to $R^{L16}$. $R^{L30}$ and $R^{L31}$ may bond together to form a ring with the carbon atom to which they are attached, and the ring is a substituted or unsubstituted cyclopentane or cyclohexane ring. $R^{L32}$ is a divalent group which forms a substituted or unsubstituted cyclopentane, cyclohexane or norbornane ring with the carbon atom to which it is attached.

Of the acid labile groups of formula (L1), the straight or branched groups we exemplified below, but not limited thereto.

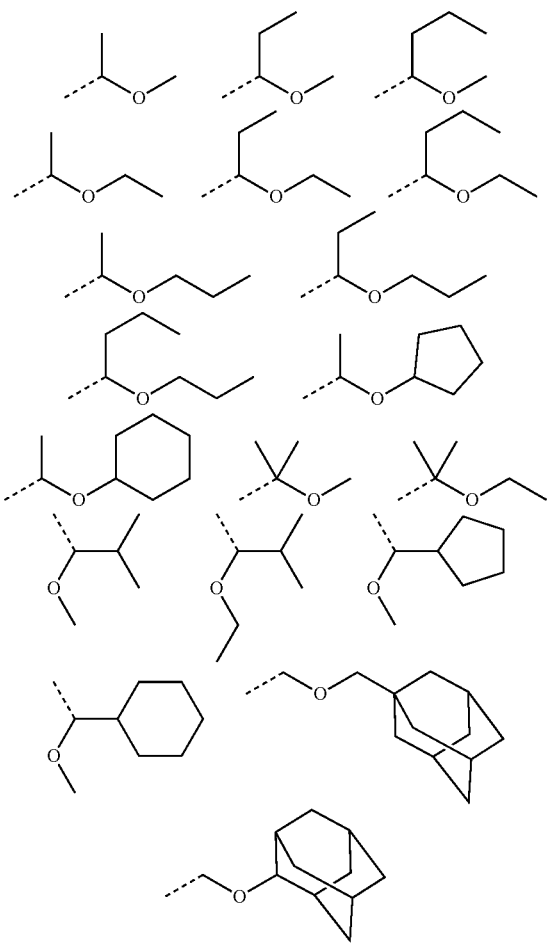

Of the acid labile groups of formula (L1), the cyclic groups are, for example, tetrahydrofuran-2-yl, 2-methyltetrahydrofuran-2-yl, tetrahydropyran-2-yl, and 2-methyltetrahydropyran-2-yl.

Examples of the acid labile group of formula (L2) include tert-butoxycarbonyl, tert-butoxycarbonylmethyl, tert-pentyloxycarbonyl, tert-pentyloxycarbonylmethyl, 1,1-diethylpropyloxycarbonyl, 1,1-diethylpropyloxycarbonylmethyl, 1,1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Examples of the acid labile group of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-tert-butylcyclopentyl, 1-cyclohexycyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups of formula (L4), those groups of the following formulae (L4-1) to (L4-4) are preferred.

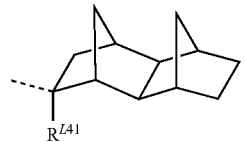

(L4-1)

(L4-2)

(L4-3)

(L4-4)

In formulas (L4-1) to (L4-4), the broken line denotes a point and direction of attachment. $R^{L41}$ is each independently a $C_1$-$C_{10}$ monovalent hydrocarbon group, which may be straight, branched or cyclic. Exemplary groups include alkyl groups such as methyl, ethyl, propyl, isopropyl, n-butyl, sec-butyl, tert-butyl, tert-pentyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. When the acid labile group $X^A$ is of formula (L4), a plurality of stereoisomers may be included.

For example, the formula (L4-3) represents one or a mixture of two selected from groups having the following formulas (L4-3-1) and (L4-3-2).

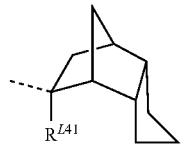

(L4-3-1)

(L4-3-2)

Note that $R^{L41}$ is as defined above.

Similarly, the formula (L4-4) represents one or a mixture of two or more selected from groups having the following formulas (L4-4-1) to (L4-4-4).

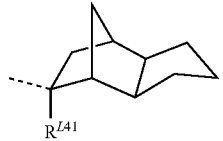

(L4-4-1)

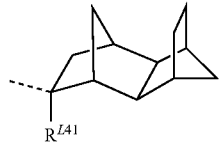

(L4-4-2)

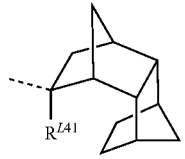

(L4-4-3)

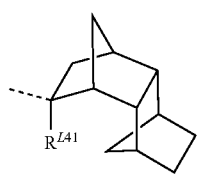

(L4-4-4)

Note that $R^{L41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-44), the direction of attachment is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo[2.2.1]heptane structure as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

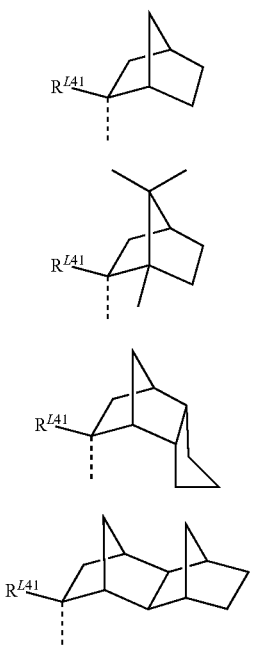

(L4-1-endo)

(L4-2-endo)

(L4-3-endo)

(L4-4-endo)

Note that $R^{L41}$ is as defined above.

Illustrative examples of the acid labile group of formula (L4) are given below.

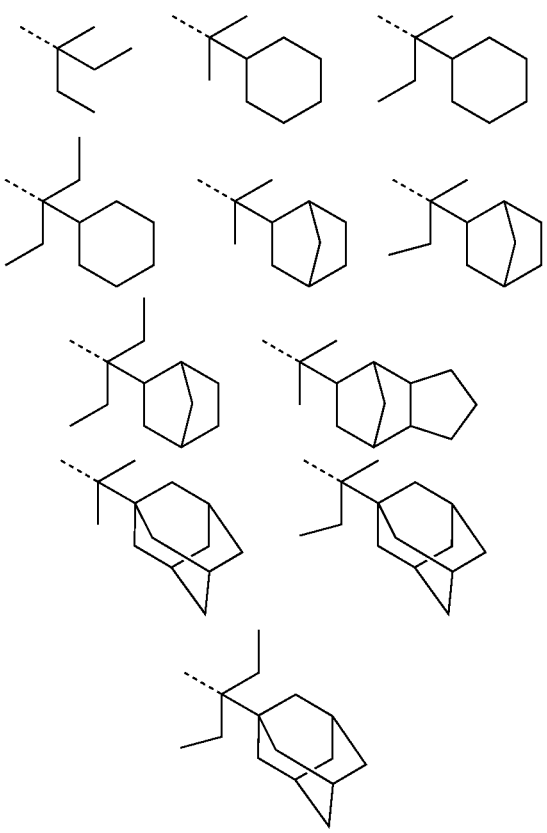

Illustrative examples of the acid labile group of formula (L6) are given below, but not limited thereto.

Illustrative examples of the acid labile group of formula (L7) are given below, but not limited thereto.

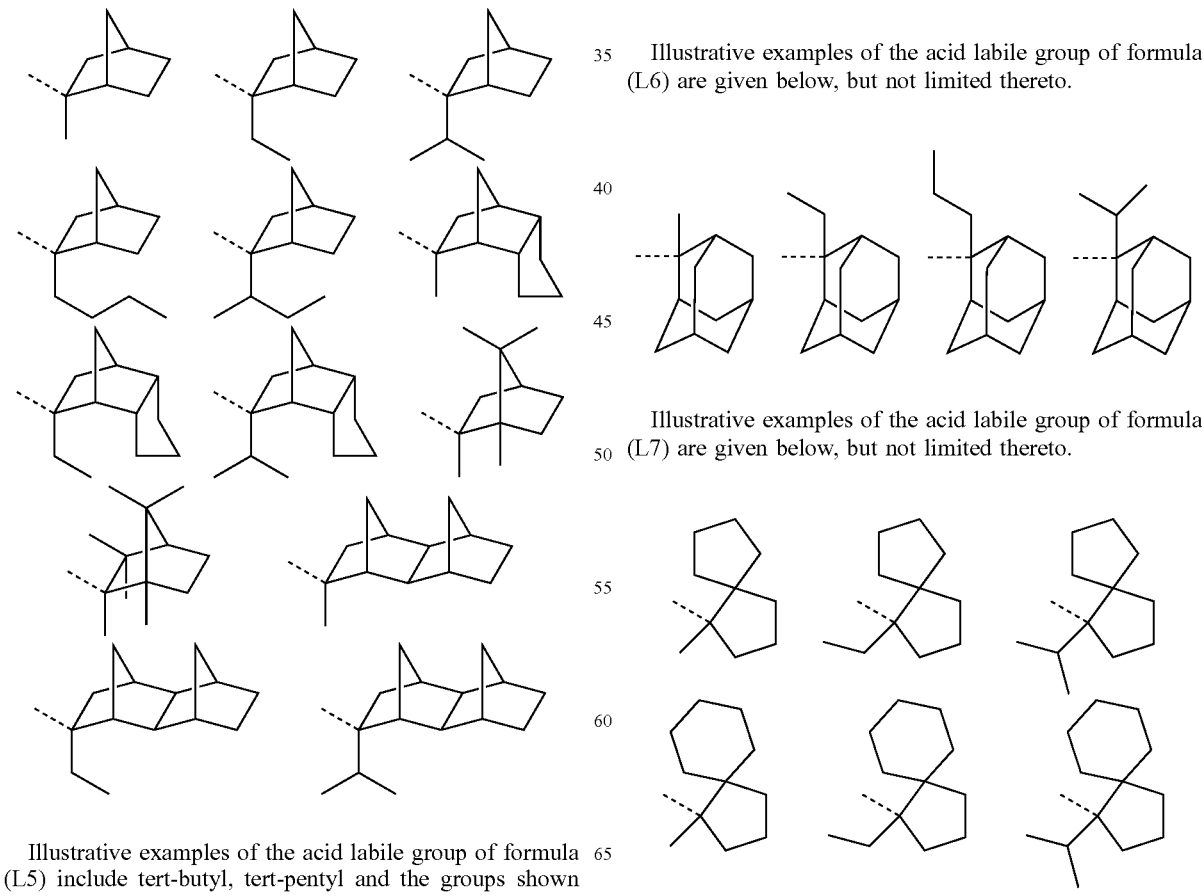

Illustrative examples of the acid labile group of formula (L5) include tert-butyl, tert-pentyl and the groups shown below, but are not limited thereto.

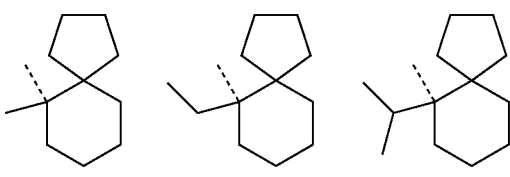
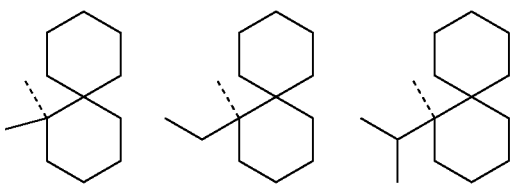
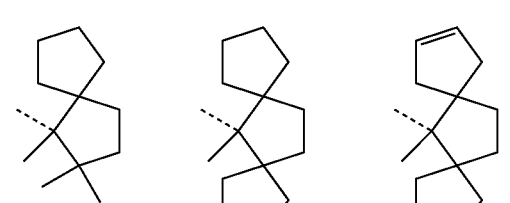

Illustrative examples of the acid labile group of formula (L8) are given below, but not limited thereto.

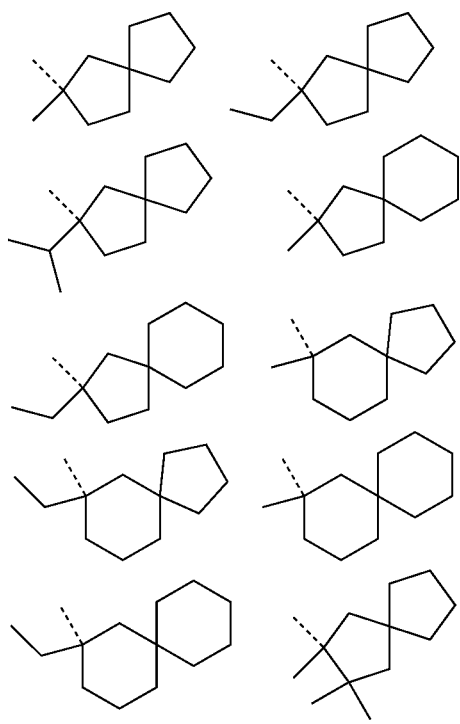

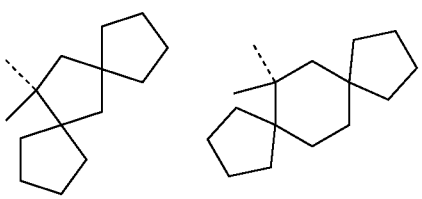

Illustrative examples of the acid labile group of formula (L9) are given below, but not limited thereto.

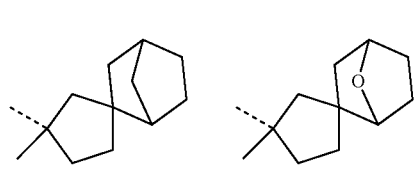
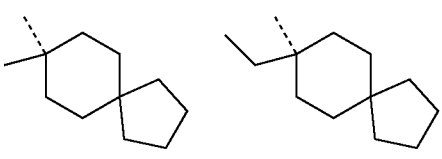
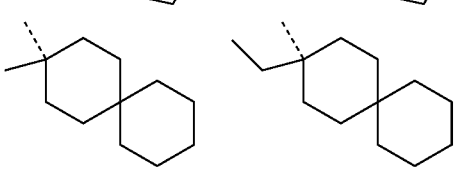
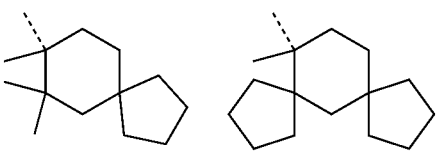
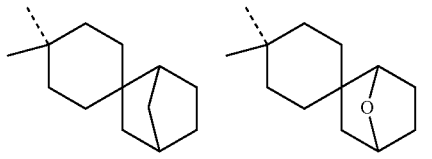

Of the acid labile groups $X^A$, suitable $C_4$-$C_{20}$ tertiary alkyl groups, trialkylsilyl groups in which each alkyl moiety has 1 to 6 carbon atoms, and $C_4$-$C_{20}$ oxoalkyl groups are as exemplified for $R^{L04}$.

Illustrative examples of the monomer having formula (A-1) are given below, but not limited thereto. $R^A$ is as defined above.

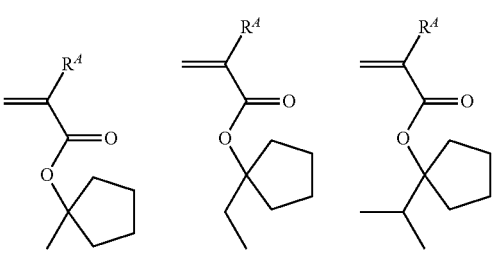

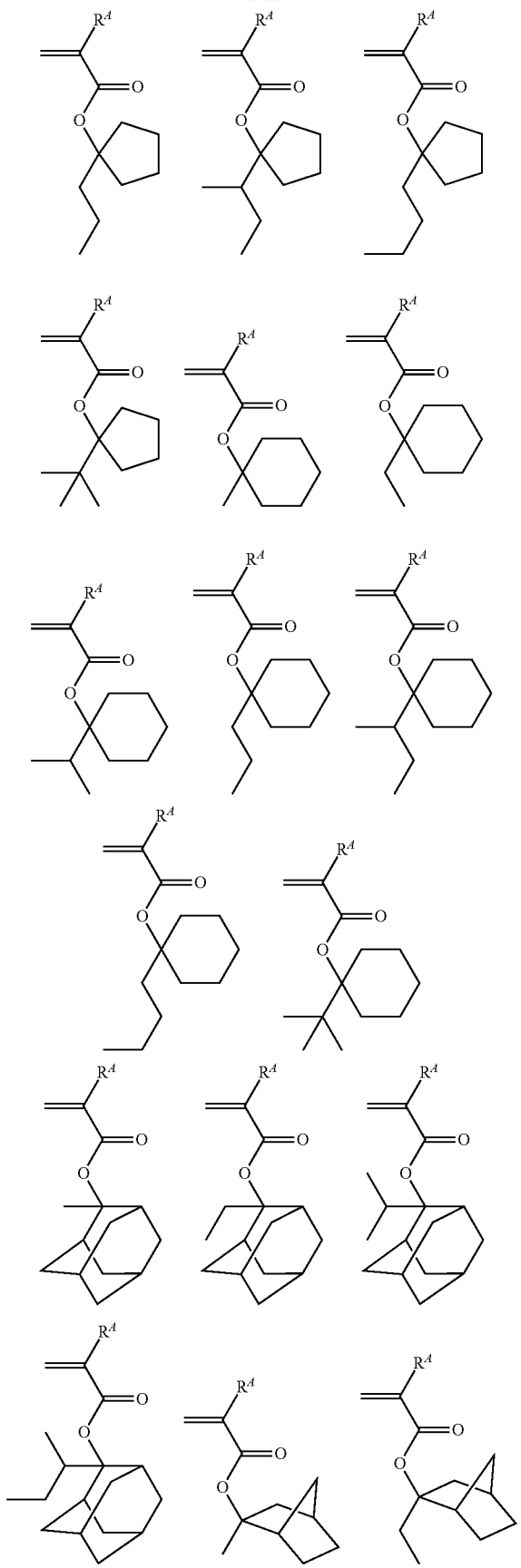
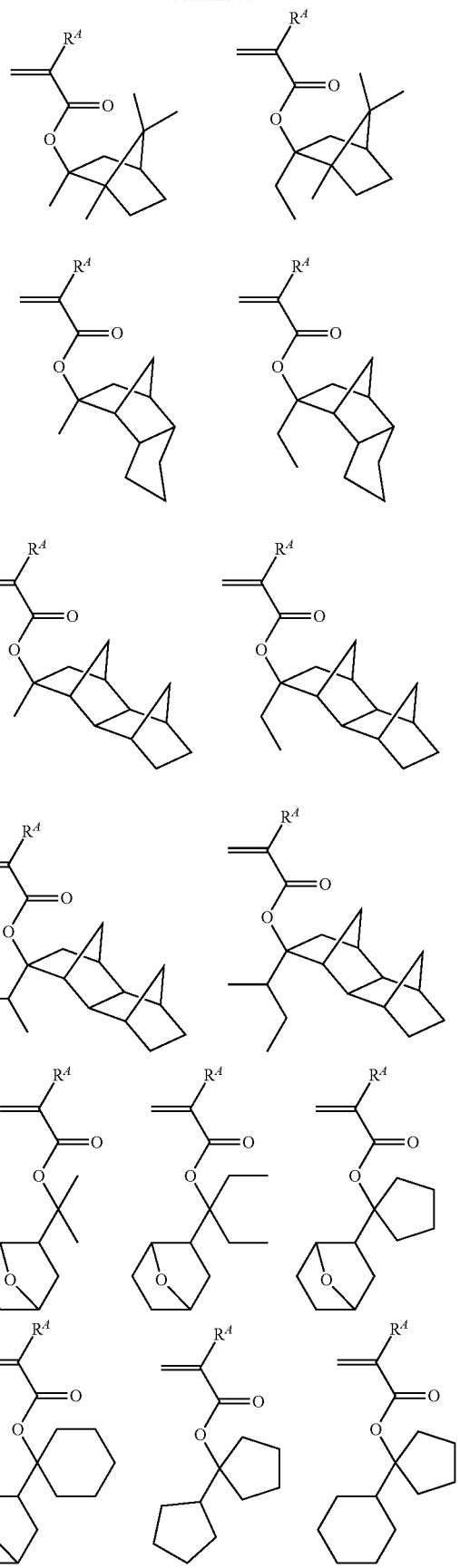

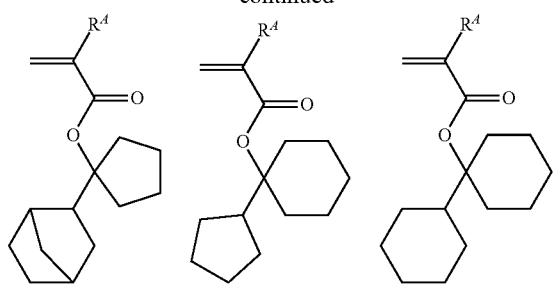
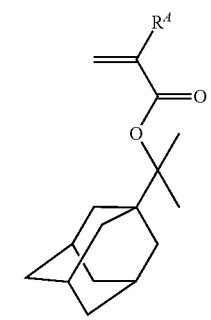
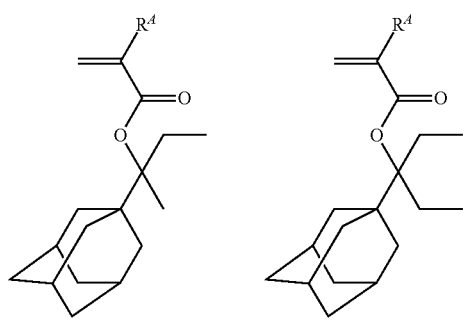
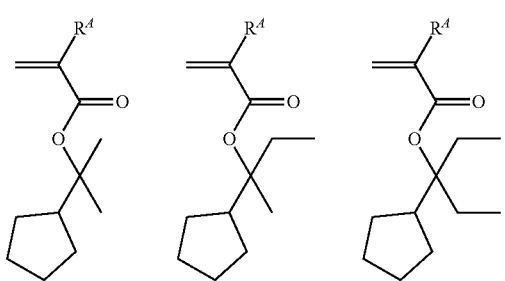
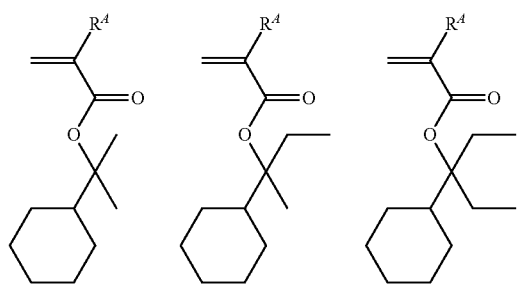
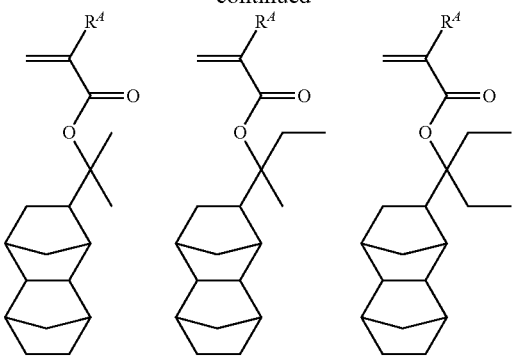
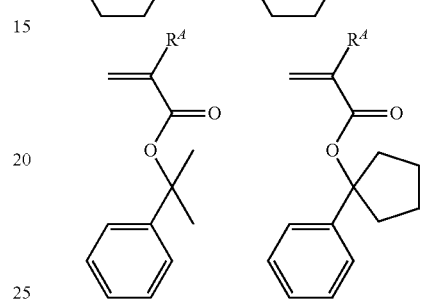
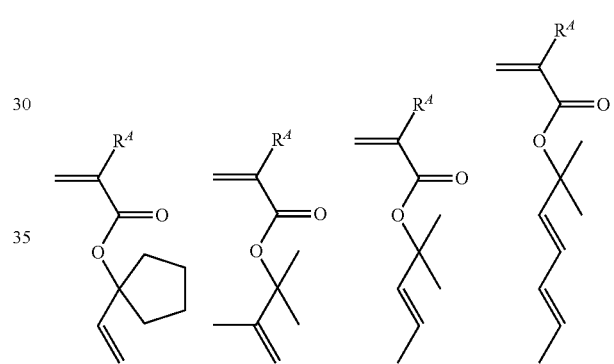
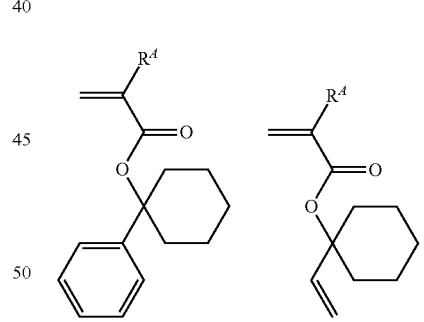
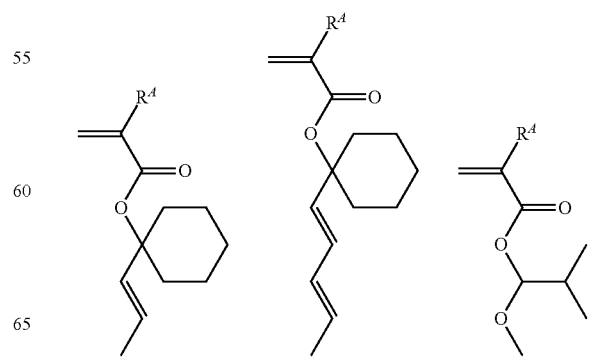

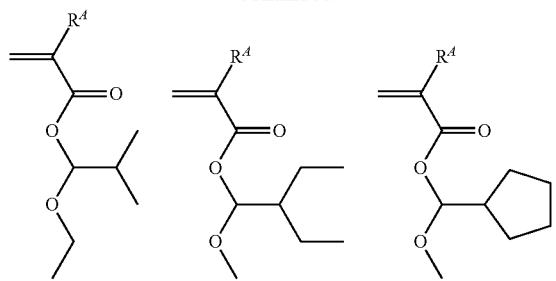
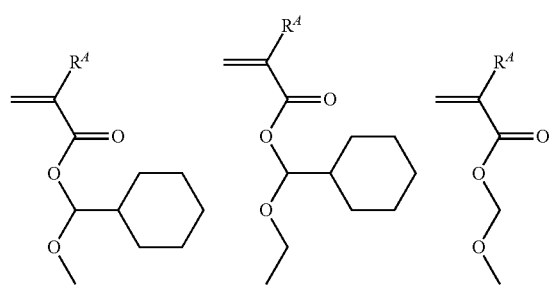
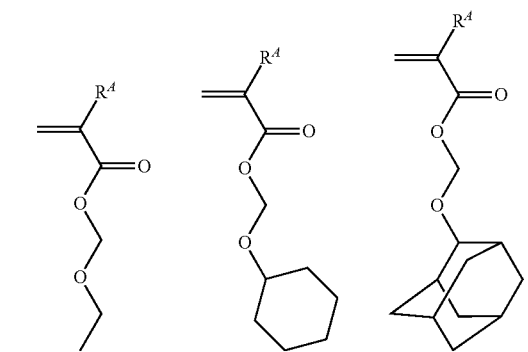
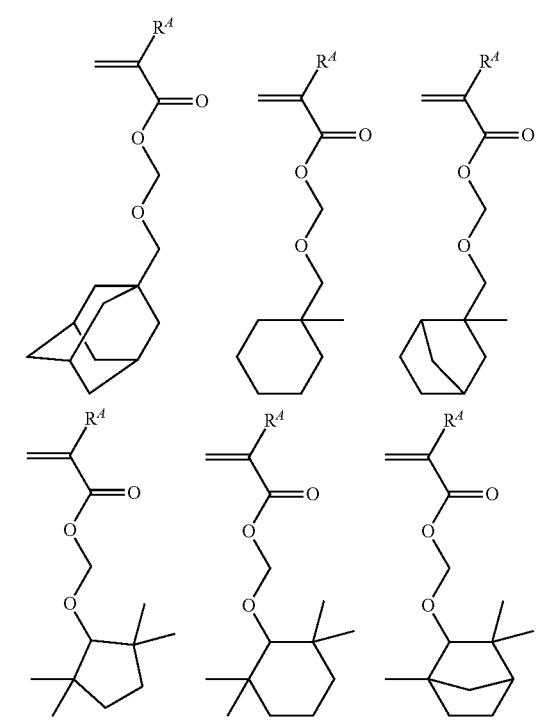
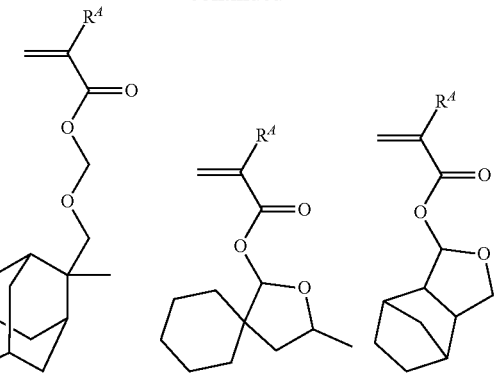
Illustrative examples of the monomer having formula (A-2) are given below, but not limited thereto. $R^A$ is as defined above.
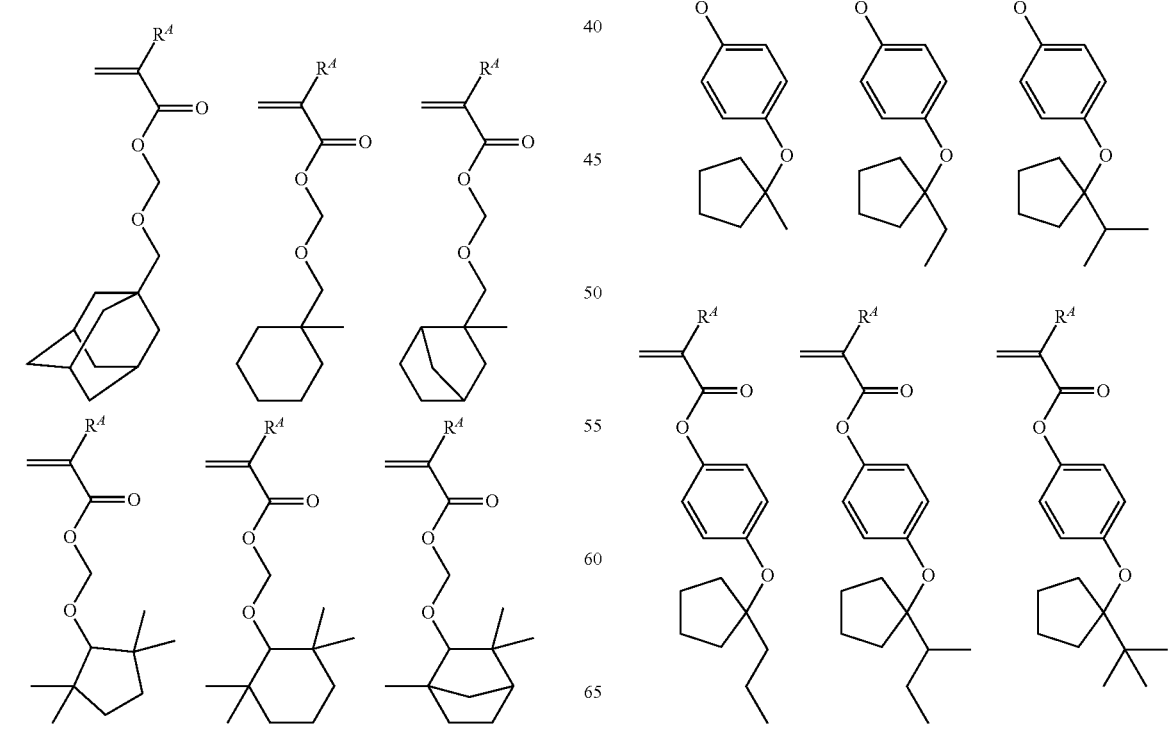

-continued
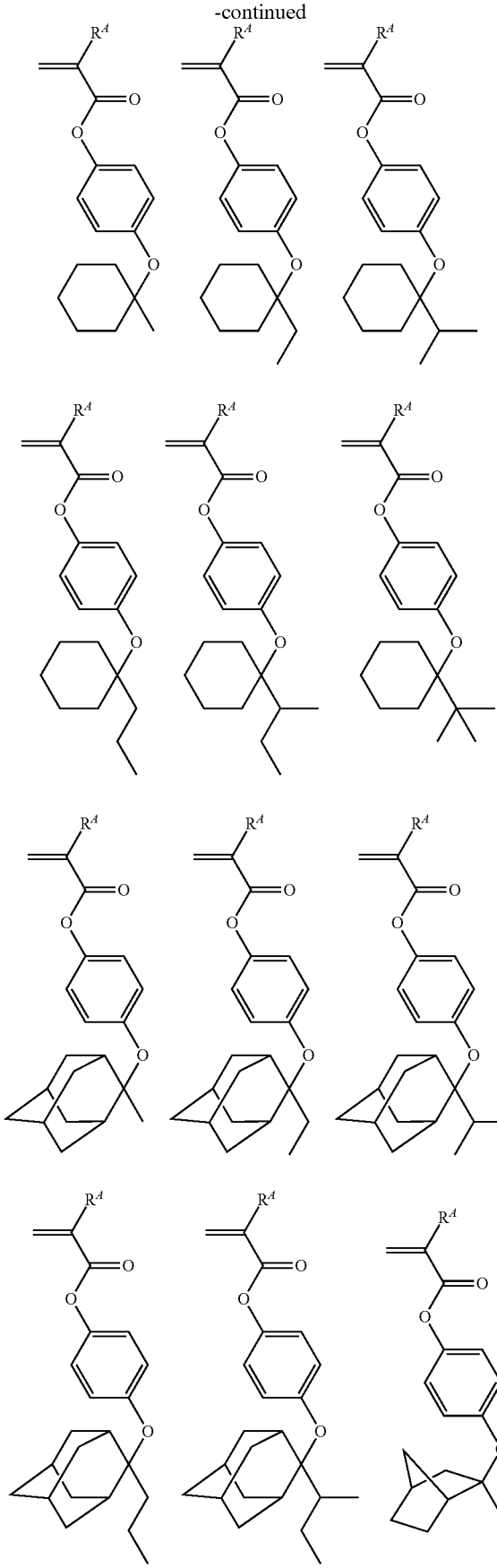
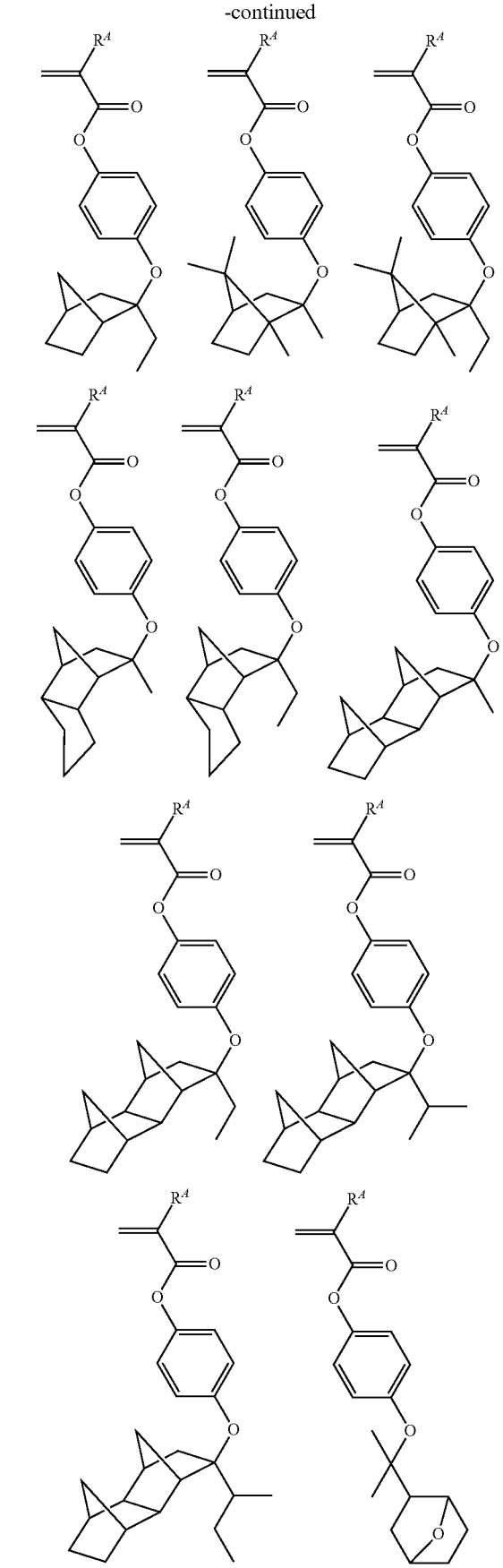

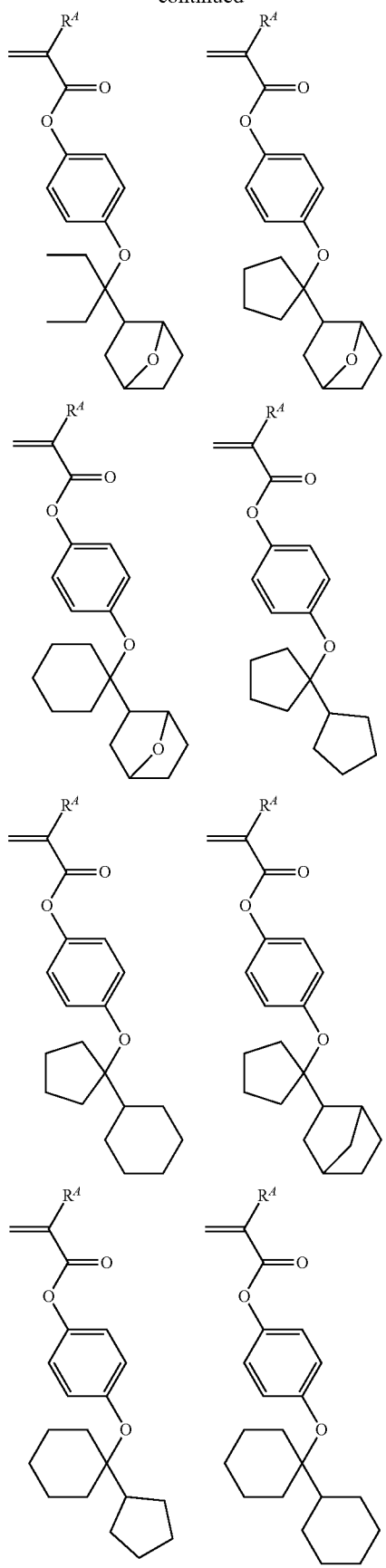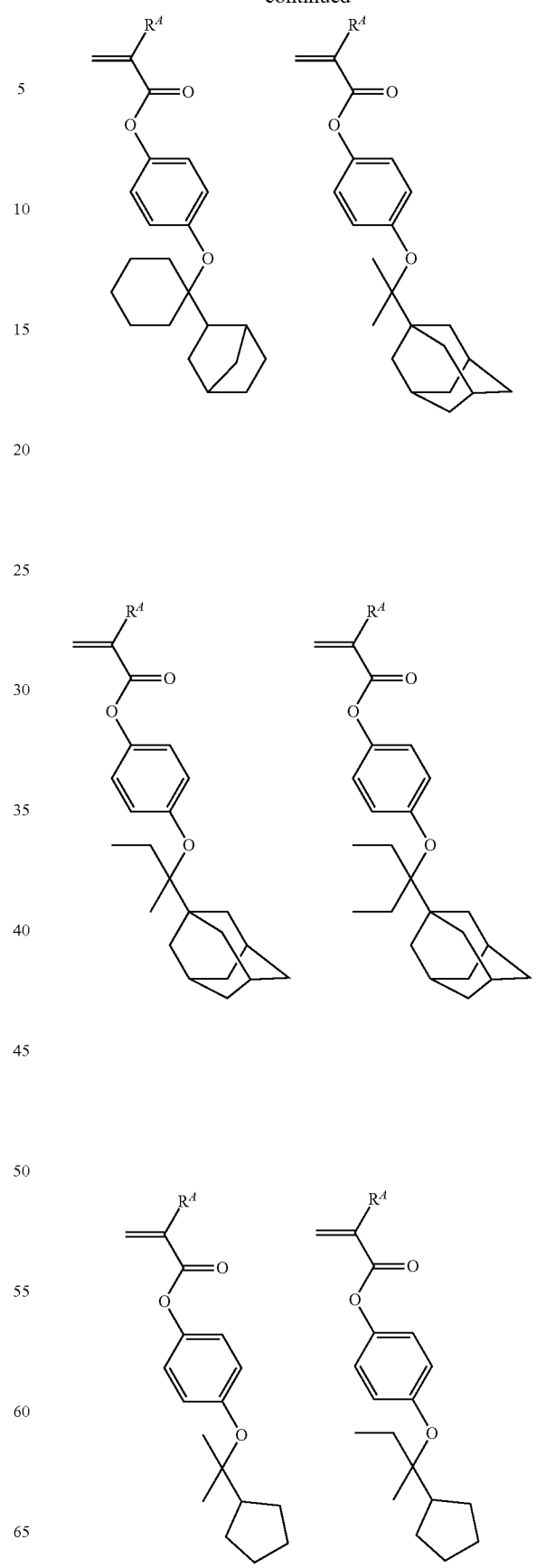

-continued
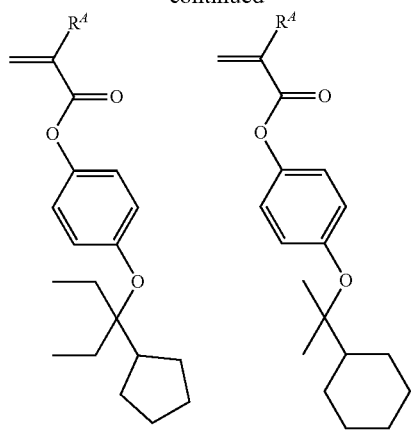
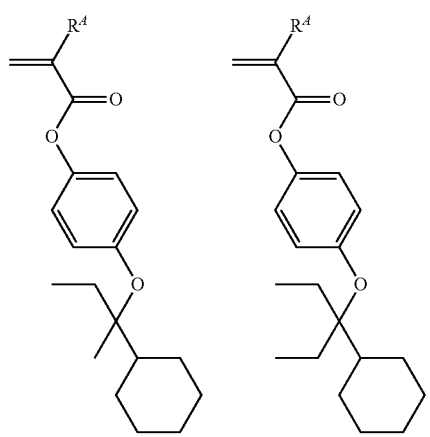
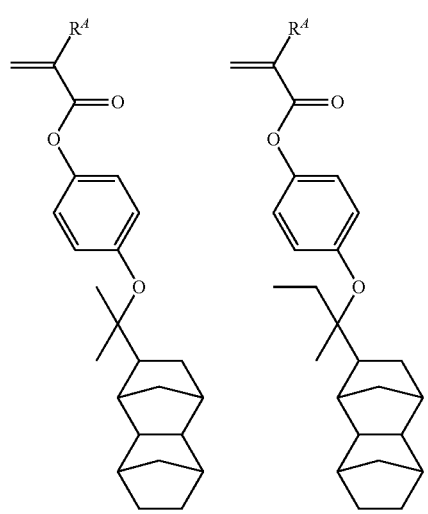
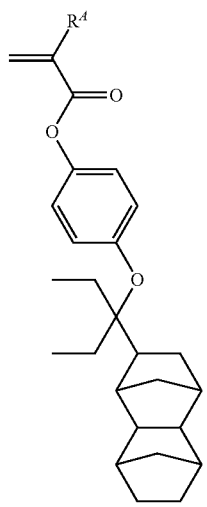
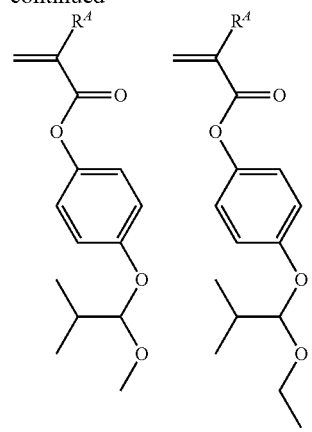
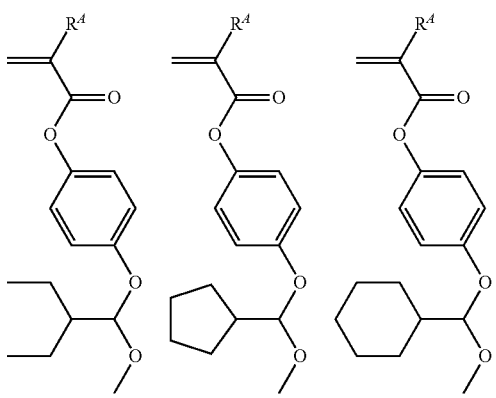
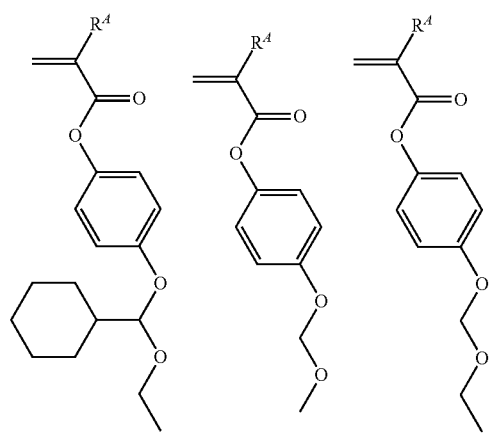

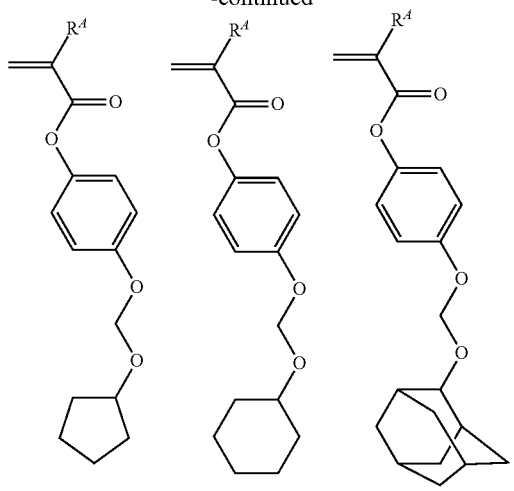
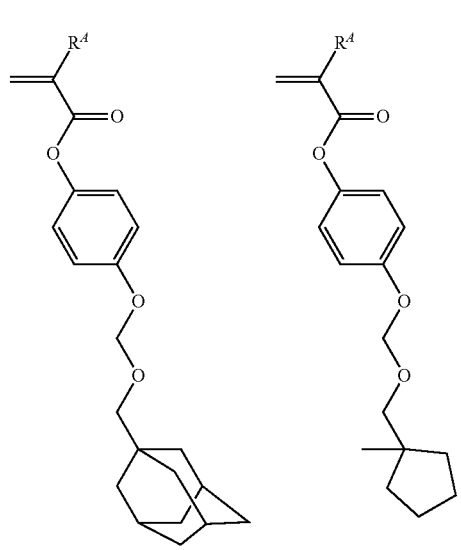
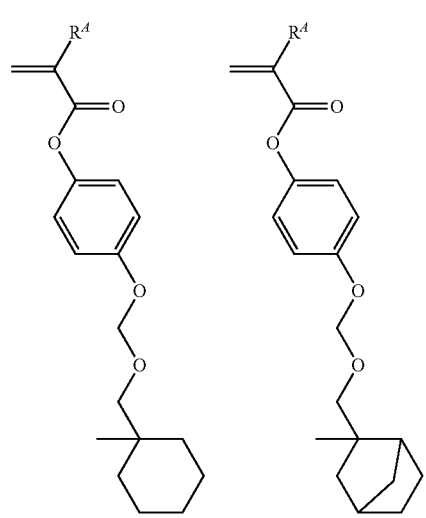
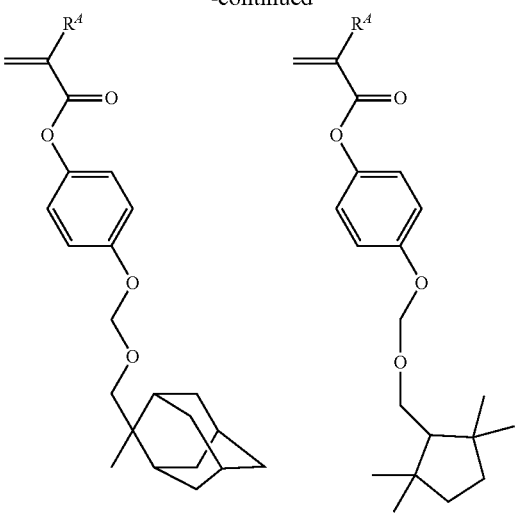
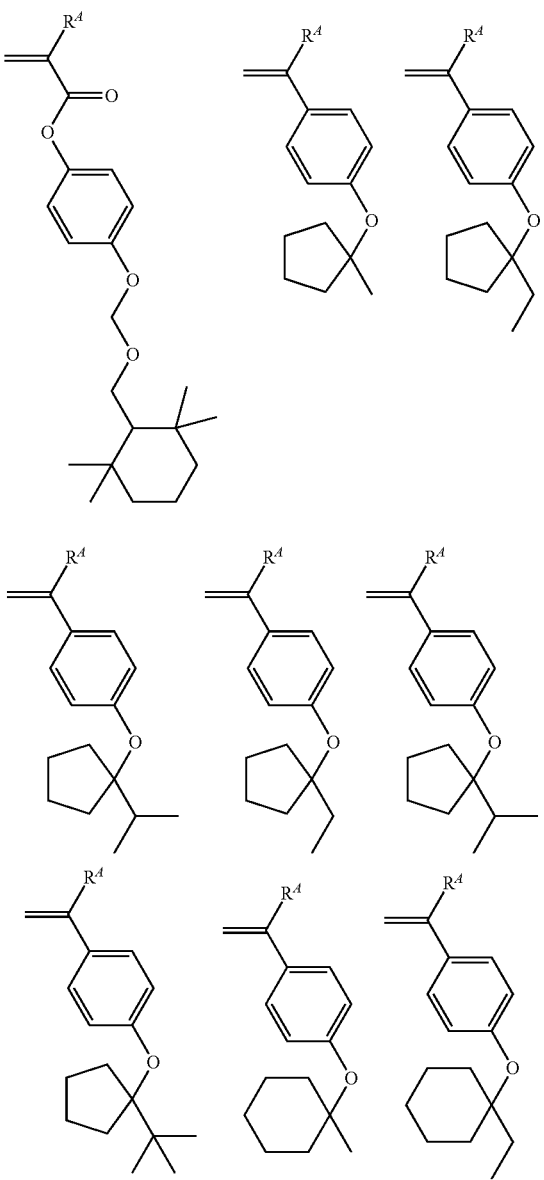

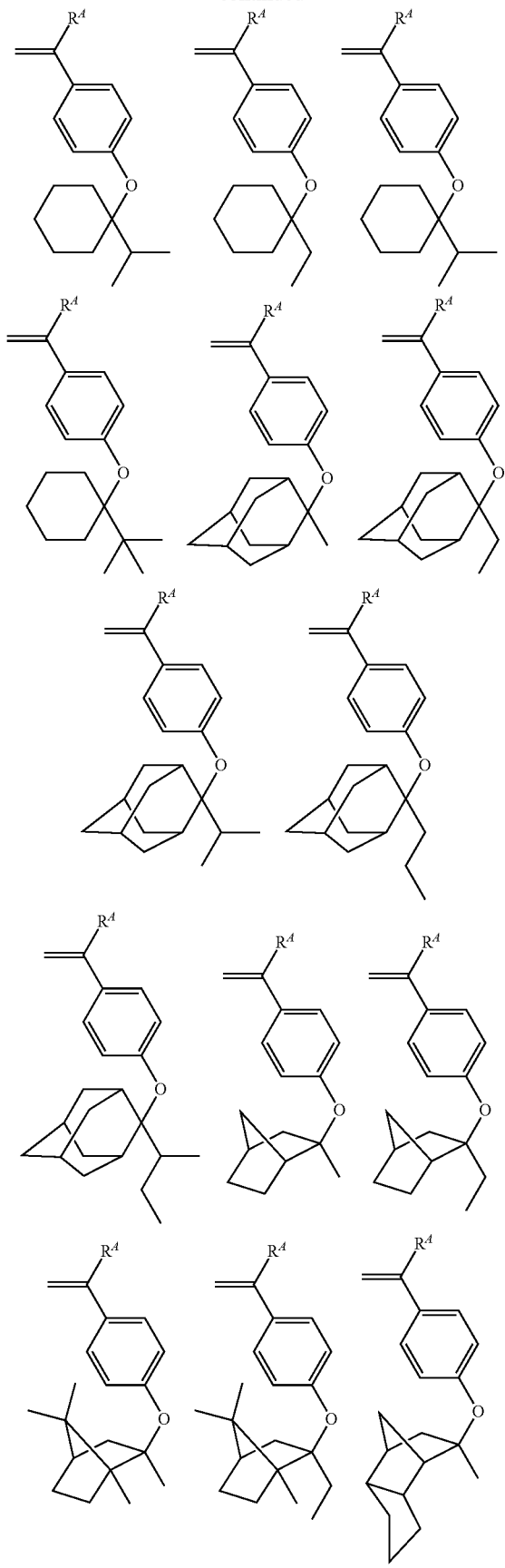
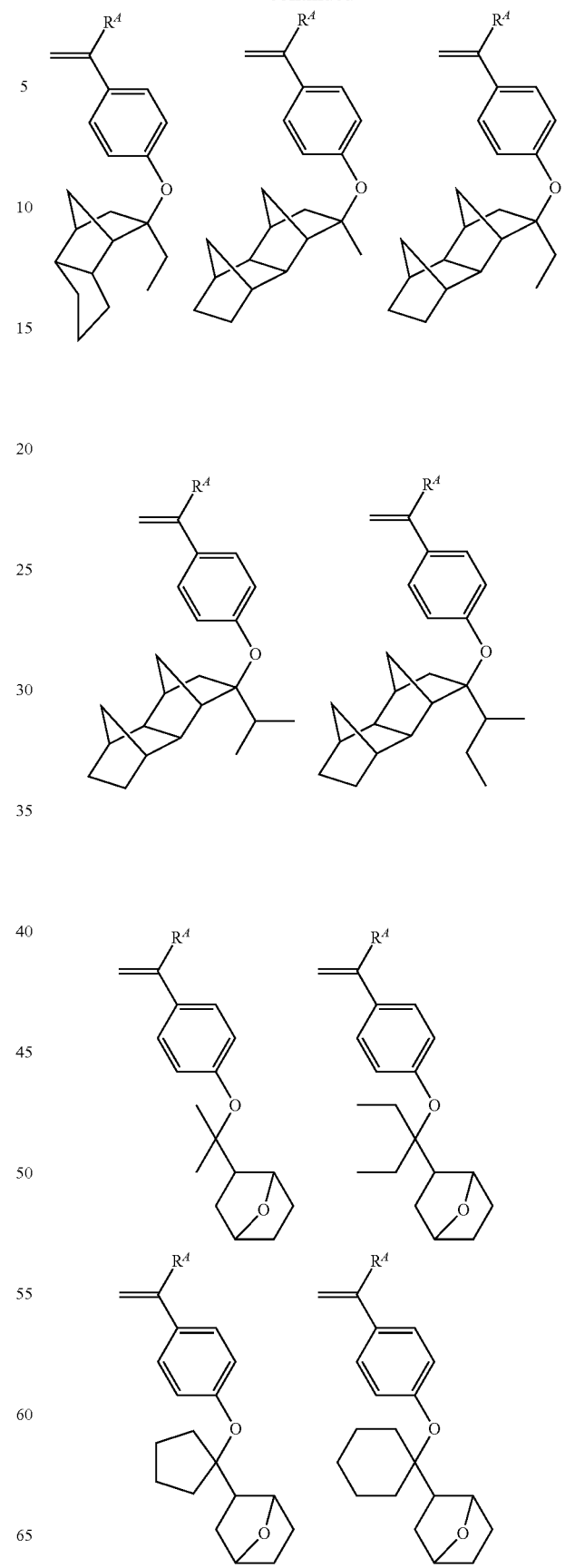

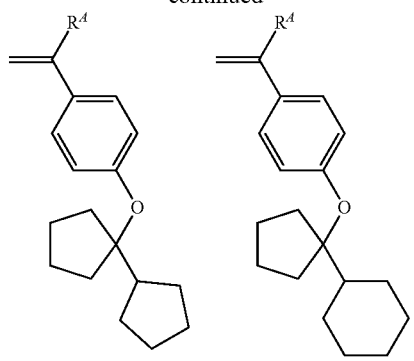
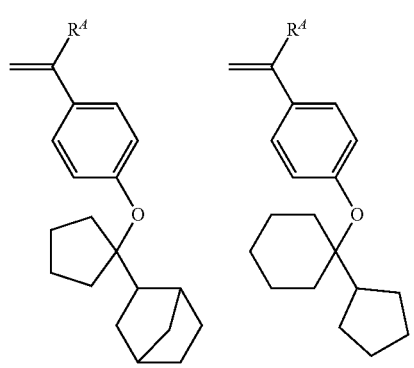
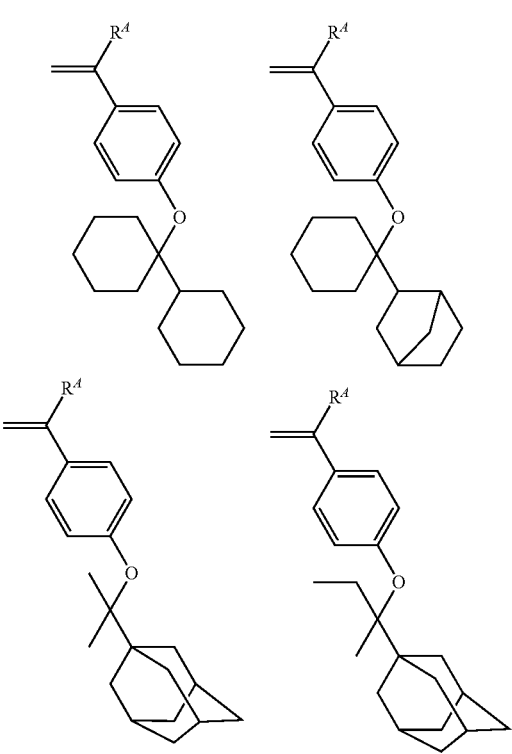
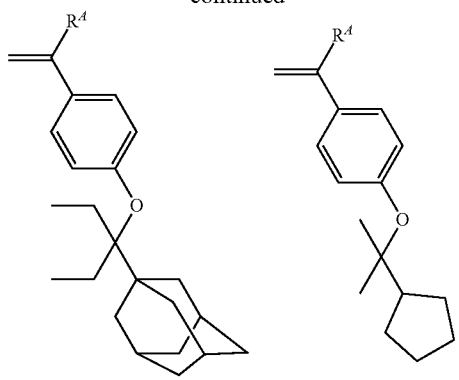
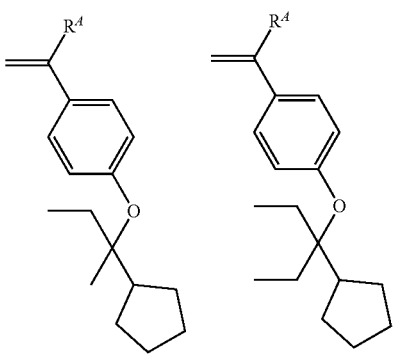
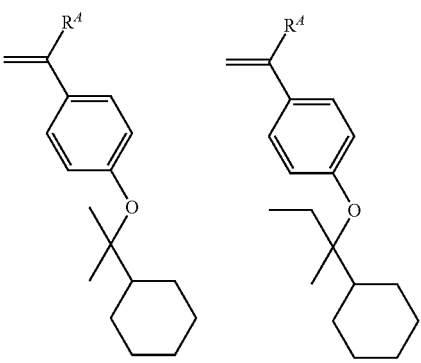
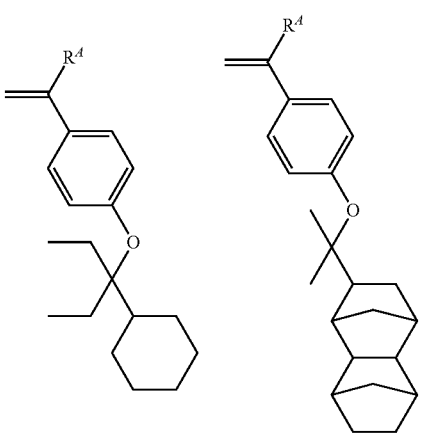

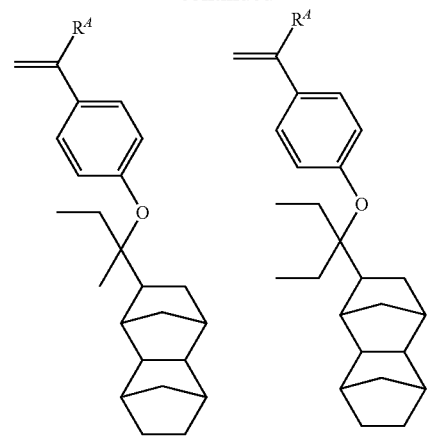
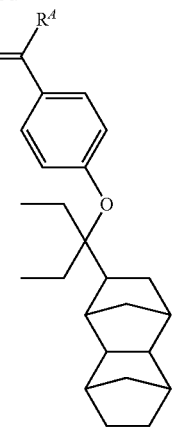
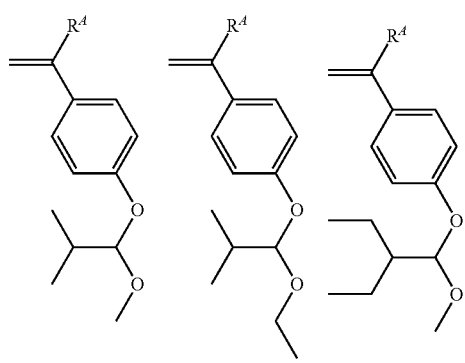
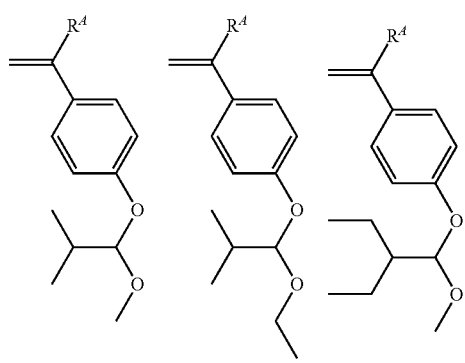
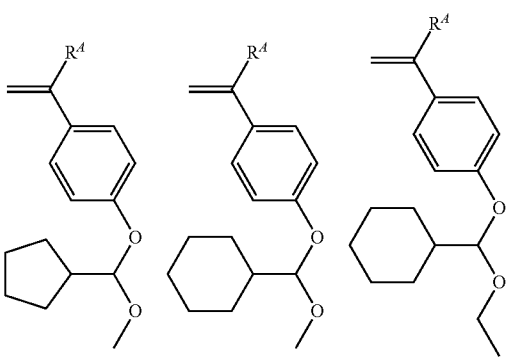
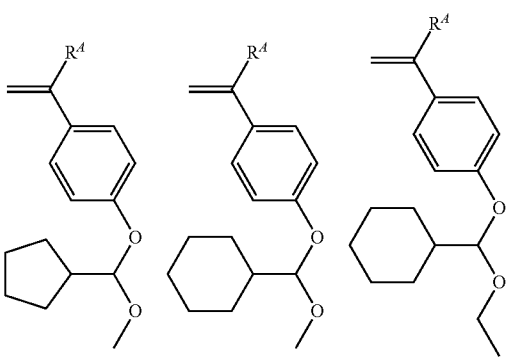
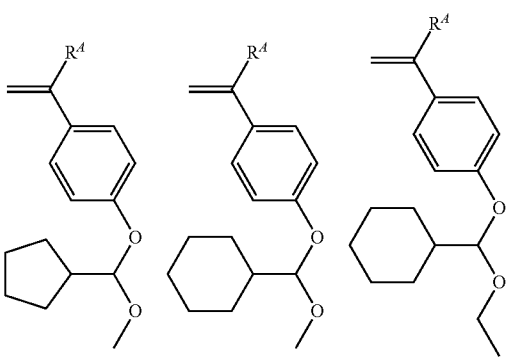
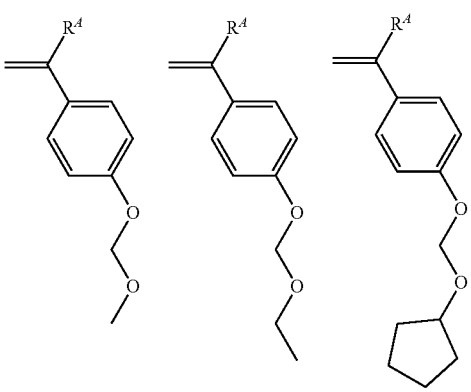
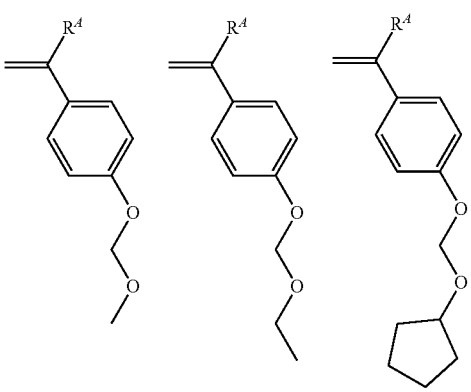
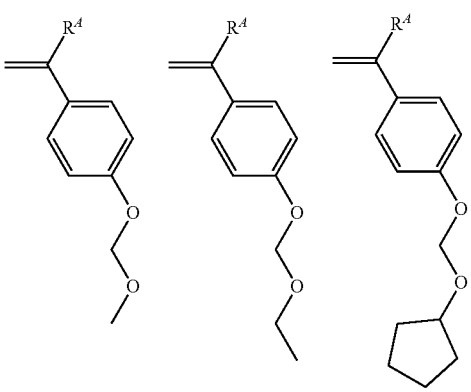
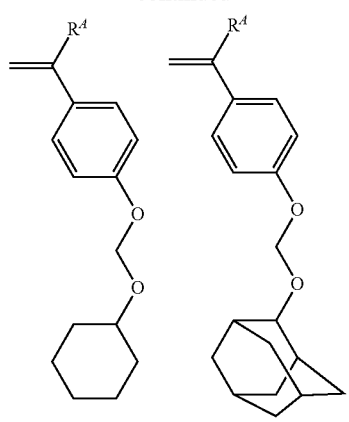
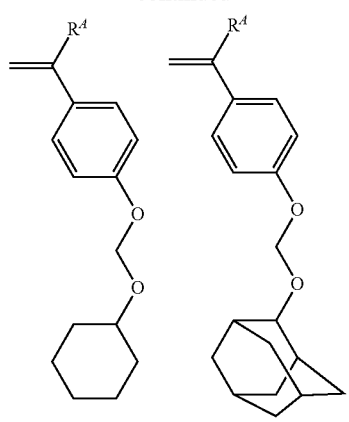
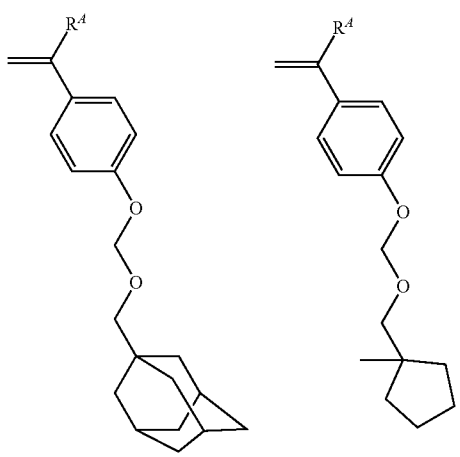
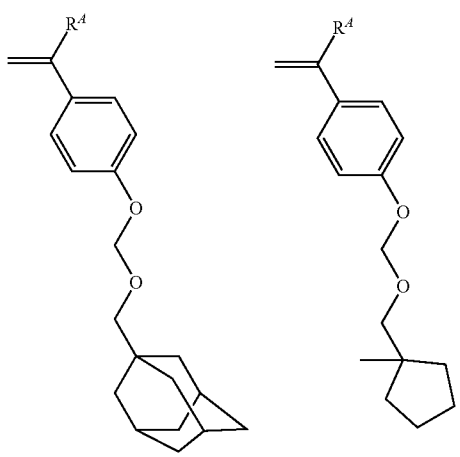
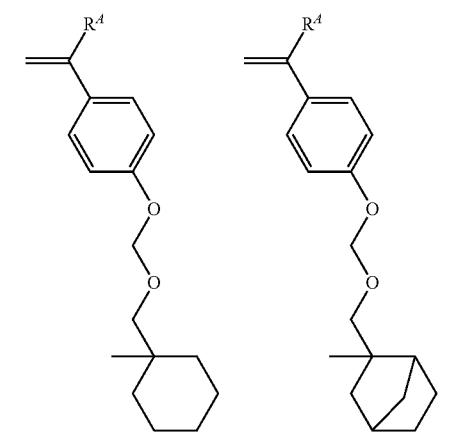
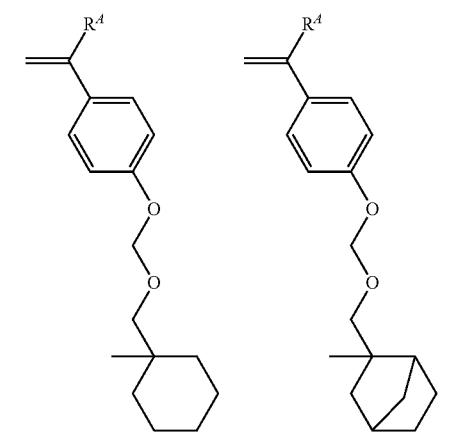

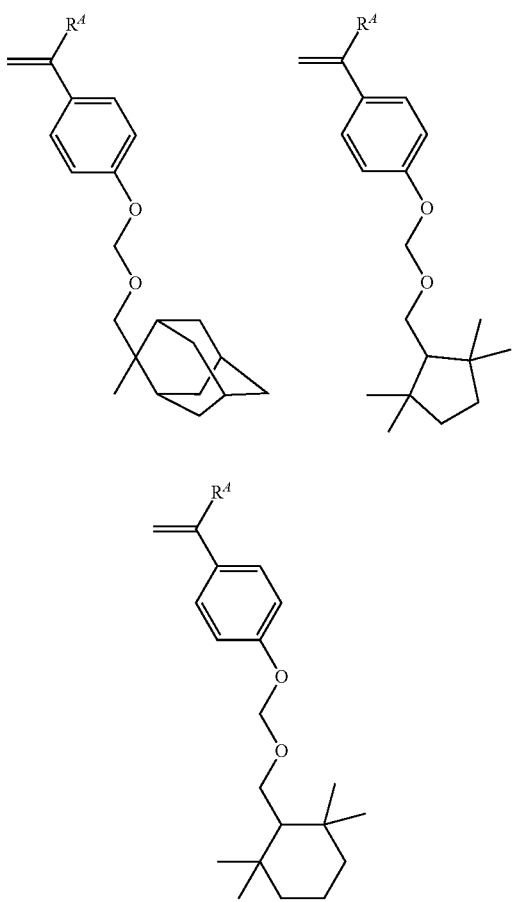

In a further embodiment, the base polymer comprises recurring units of at least one type selected from recurring units having the formula (B), recurring units having the formula (C), recurring units having the formula (D), and securing units having the formula (E), all defined below. These recurring units are also referred to as recurring units (B) to (E), respectively.

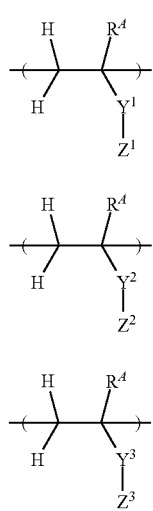

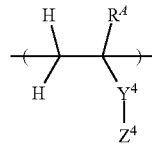

In formulae (B) to (D), $R^A$ is hydrogen, fluorine, methyl or trifluormethyl. $Z^1$ is a $C_1$-$C_{20}$ fluoroalcohol-containing substituent group. $Z^2$ is a $C_1$-$C_{20}$ phenolic hydroxyl-containing substituent group. $Z^3$ is a $C_1$-$C_{20}$ carboxyl-containing substituent group. $Z^4$ is a substituent group containing lactone skeleton, sultone skeleton, carbonate skeleton, cyclic ether skeleton, acid anhydride skeleton, alcoholic hydroxyl moiety, alkoxycarbonyl moiety, sulfonamide moiety, or carbamoyl moiety. $Y^1$ to $Y^4$ are each independently a single bond, methylene, ethylene, phenylene, fluorinated phenylene, naphthylene, —O—$Y^5$—, —C(=O)—O—$Y^5$—, or —C(=O)—NH—$Y^5$—. $Y^5$ is a $C_1$-$C_6$ alkanediyl, $C_2$-$C_6$ alkenediyl, phenylene or naphthylene group, which may contain a carbonyl moiety, ester bond, ether bond or hydroxyl moiety.

The recurring unit (B) has a $C_1$-$C_{20}$ fluoroalcohol-containing substituent group having high affinity to alkaline aqueous solution. Preferred examples of the fluoroalcohol-containing unit include recurring units having a 1,1,1,3,3,3-hexafluoro-2-propenol residue or 2-hydroxy-2-trifluoromethyloxolane structure as described in JP-A 2007-297590, JP-A 2008-111103, JP-A 2008-122932, and JP-A 2012-128067.

It is possible that once fluoroalcohol is protected with an acyl group or acid labile group, a fluoroalcohol-containing unit corresponding to formula (B) is generated by hydrolysis in alkaline aqueous solution developer or deprotection with acid after exposure. Preferred examples of the recurring unit in this embodiment include those described in JP-A 2012-128067, paragraphs [0036]-[0040] and specifically those of formulae (2a), (2b) and (2f) in paragraph [0041].

Examples of the monomer from which recurring units (B) are derived are shown below, but not limited thereto. $R^A$ is as defined above.

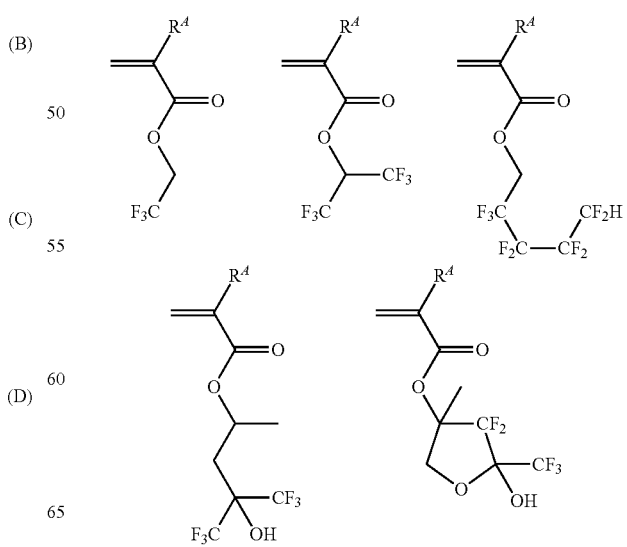

-continued

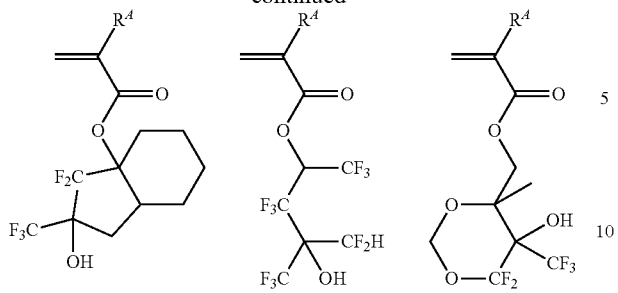
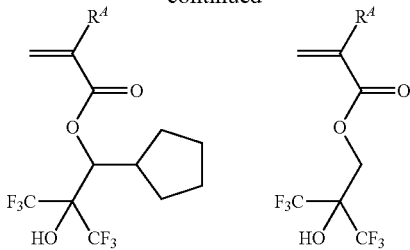

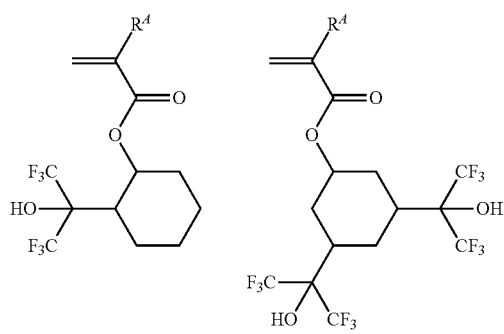

The recurring units (C) are units having a phenolic hydroxyl group, for example, units derived from a monomer having the formula (C-1).

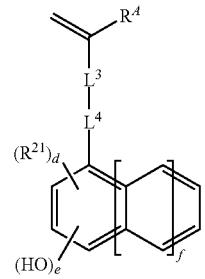

(C-1)

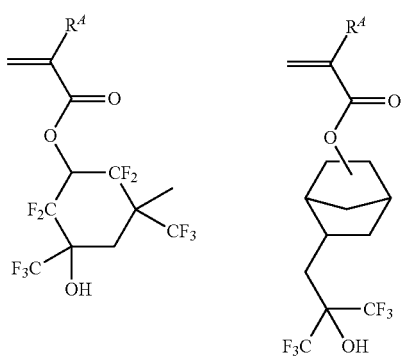

Herein $R^A$ is as defined above. $R^{21}$ is each independently hydrogen or a $C_1$-$C_6$ alkyl group which may contain an ether band or carbonyl moiety. $L^3$ is a single bond, carbonyloxy group or amide group. $L^4$ is a single bond or a $C_1$-$C_7$ alkanediyl group which may contain an ether bond or carbonyl moiety. The subscript d is an integer meeting: $d \le 5+2f-e$, e is an integer of 1 to 5, and f is an integer of 0 to 2.

In formula (C-1), examples of the $C_1$-$C_6$ alkyl group which may contain an ether bond or carbonyl moiety, represented by $R^{21}$, include, but are not limited to, methyl, ethyl, propyl, isopropyl, n-butyl, sec-butyl, tert-butyl, pentyl, hexyl, heptyl, octyl, cyclopentyl, and cyclohexyl as well as the groups shown below.

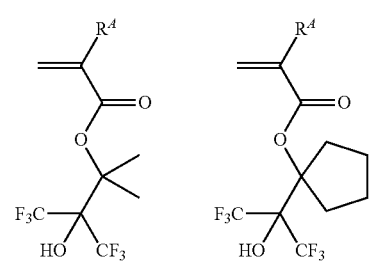

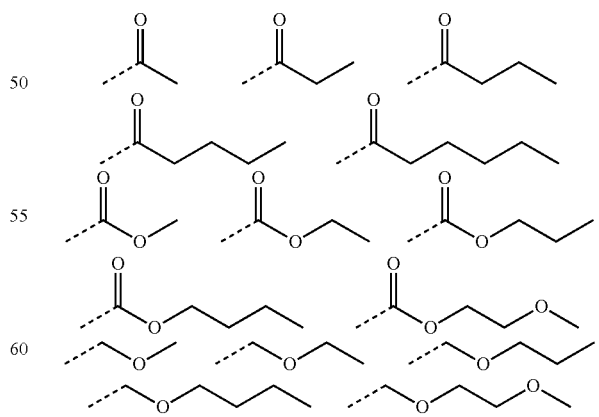

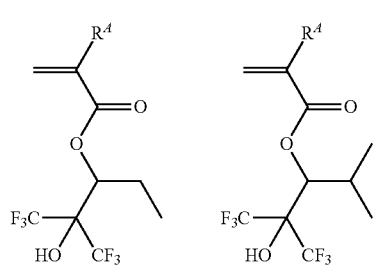

In formula (C-1), examples of the $C_1$-$C_7$ alkenediyl group which may contain an ether bond or carbonyl moiety, represented by $L^4$, include, but are not limited to, methylene, ethylene, propane-1,3-diyl, butane-1,4-diyl, pentane-1,5-diyl, hexane-1,6-diyl, and heptane-1,7-diyl as well as the groups shown below.
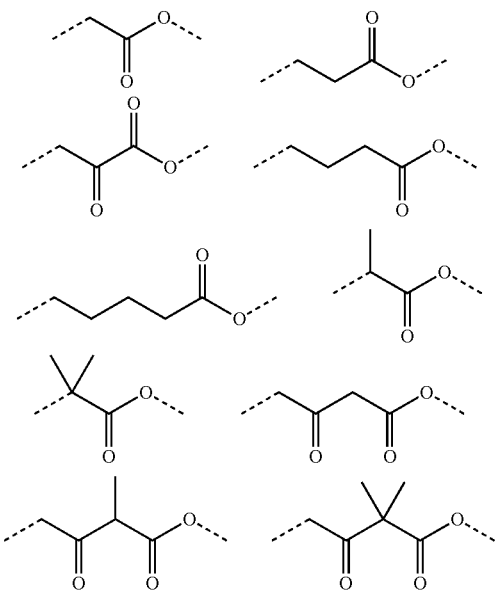
Examples of the monomer from which recurring units (C) we derived are shown below, but not limited thereto. $R^A$ is as defined above.
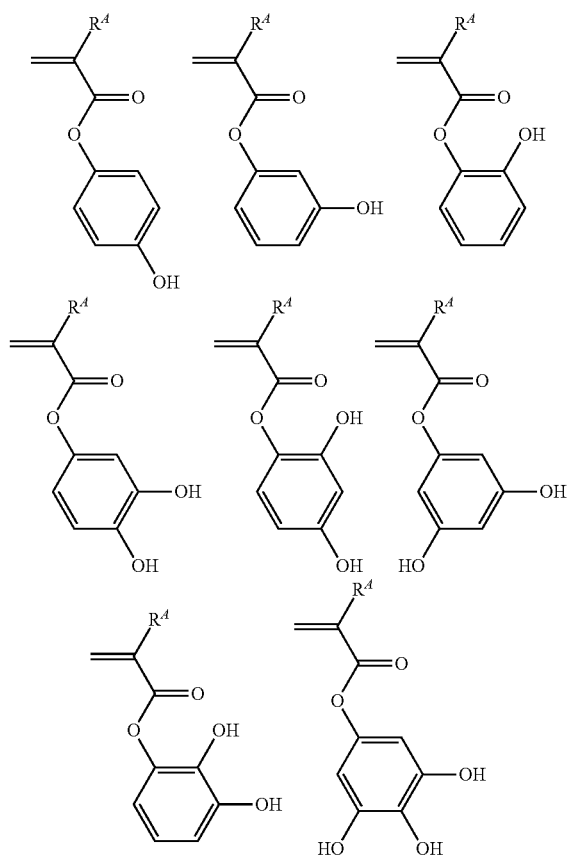
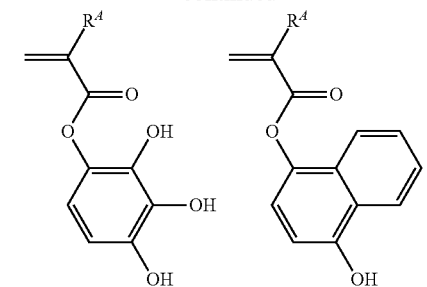
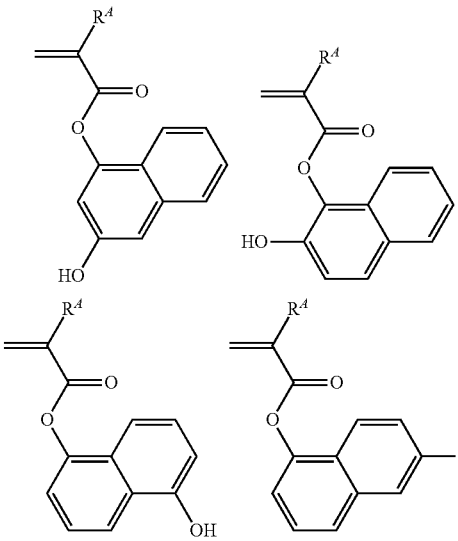
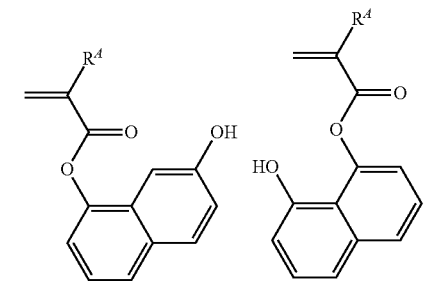
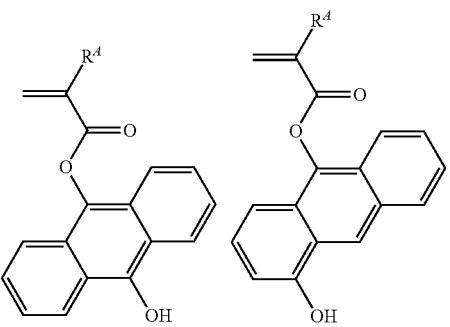
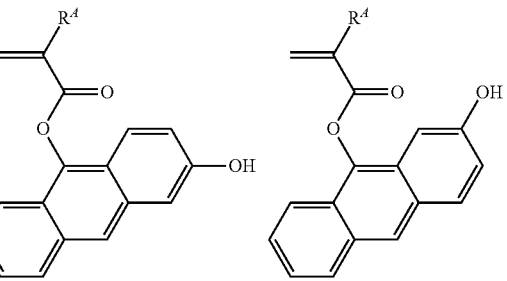

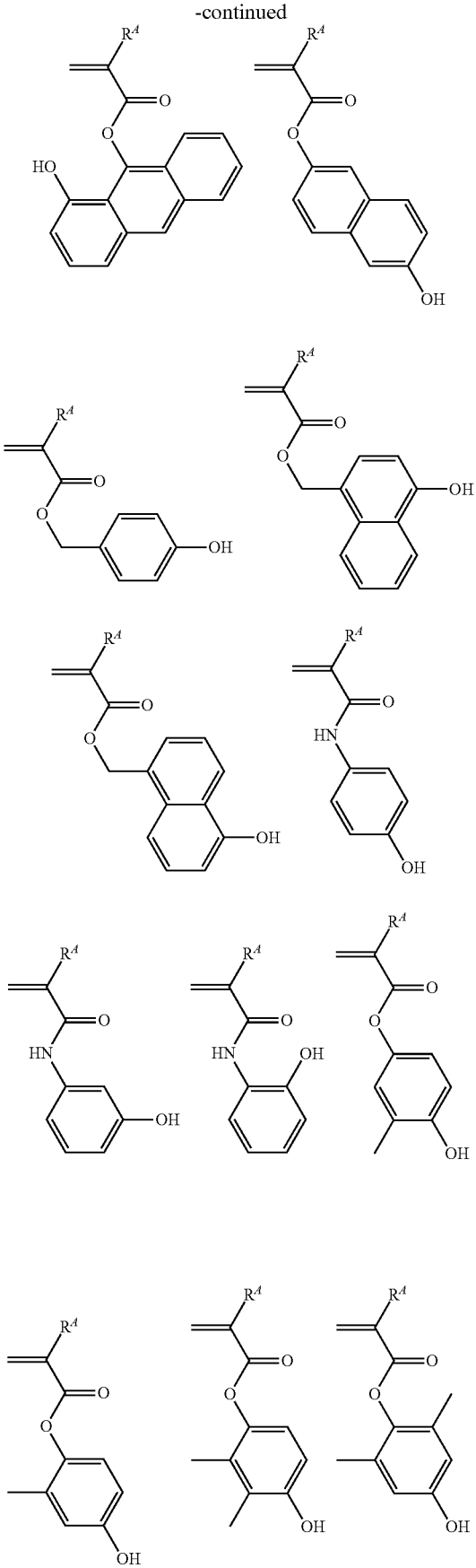
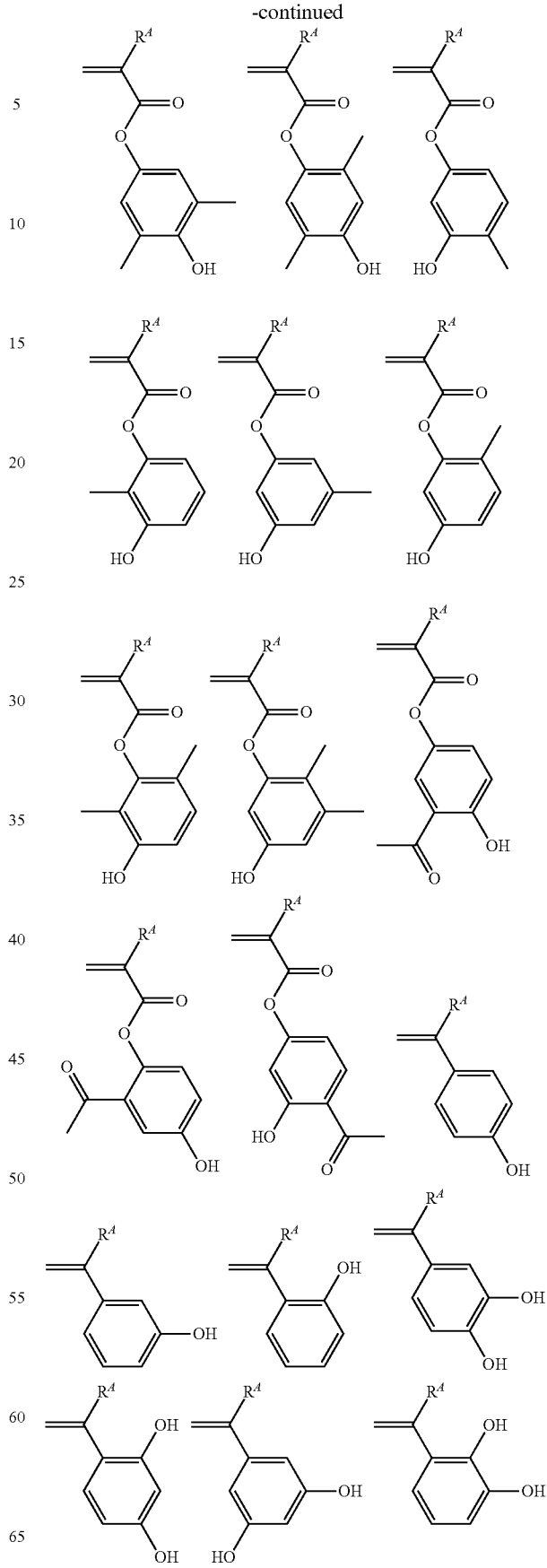

-continued

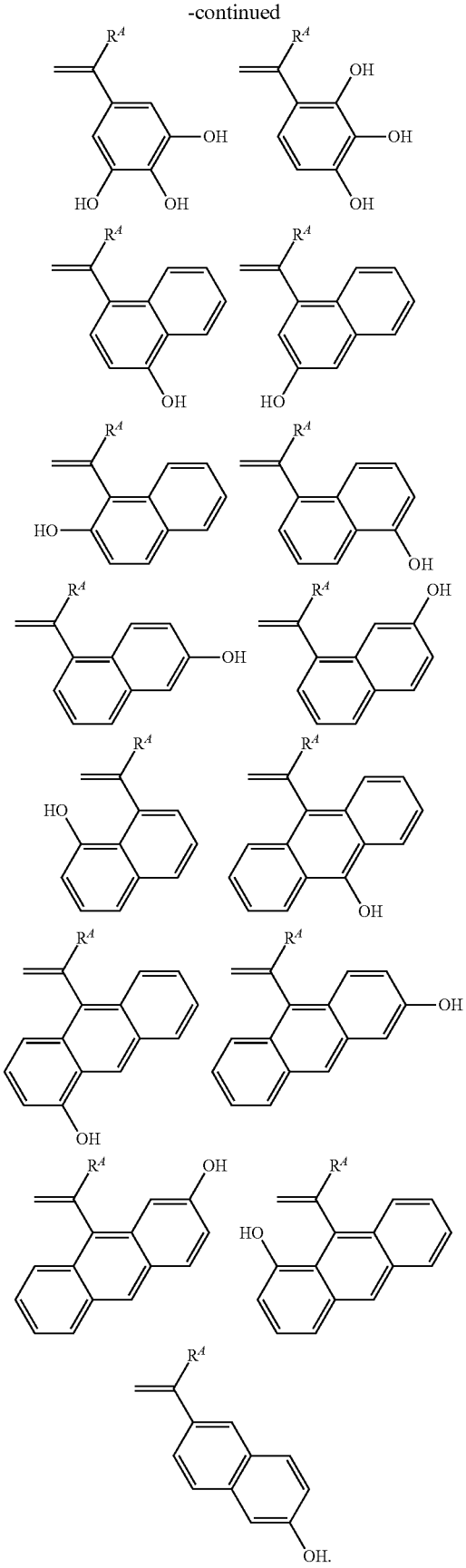

The recurring units (D) are units having a carboxyl group, for example, units derived from monomers having the following formulae. $R^A$ is as defined above.

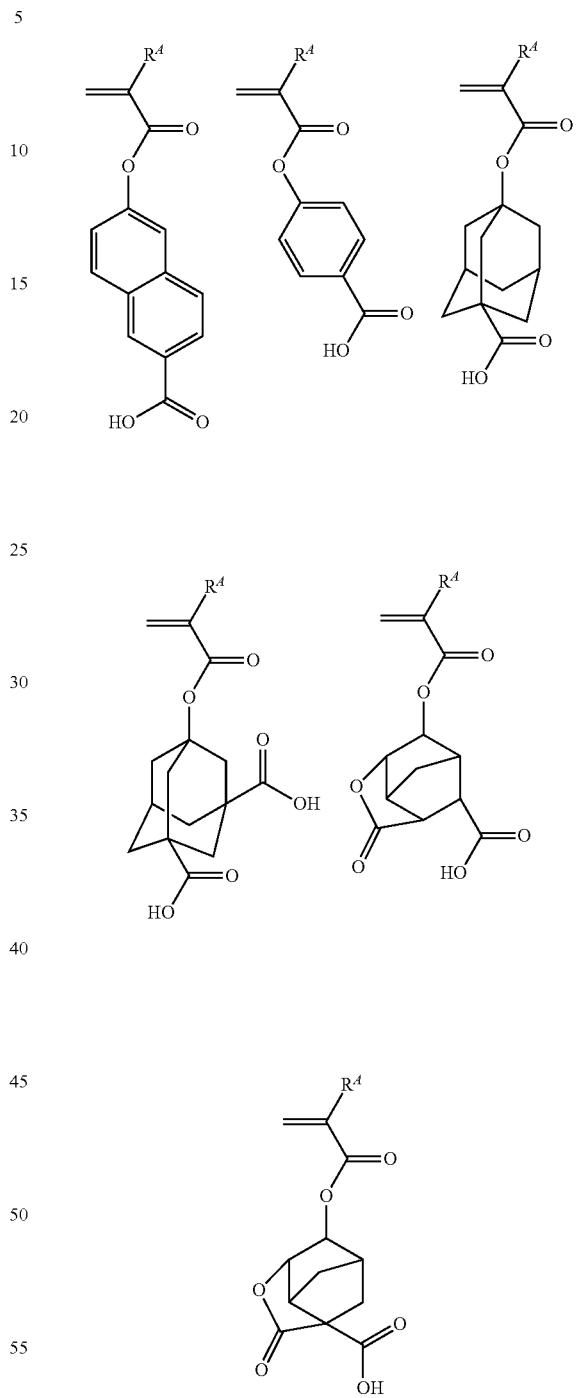

The recurring units (E) are units containing a lactone skeleton, sultone skeleton, carbonate skeleton, cyclic ether skeleton, acid hydride skeleton, alcoholic hydroxyl group, alkoxycarbonyl group, sulfonamide group or carbamoyl group.

Examples of the monomer from which recurring units (E) are derived are shown below, but not limited thereto. $R^A$ is as defined above.

-continued
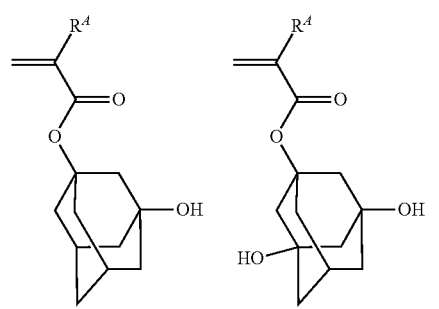
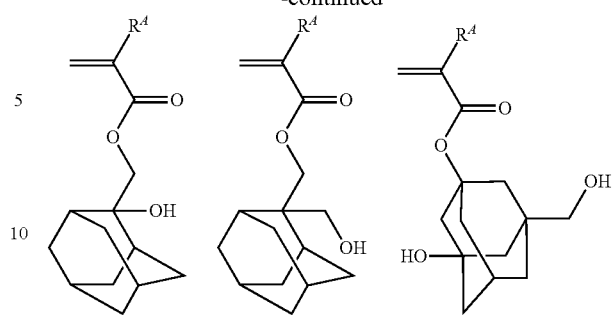
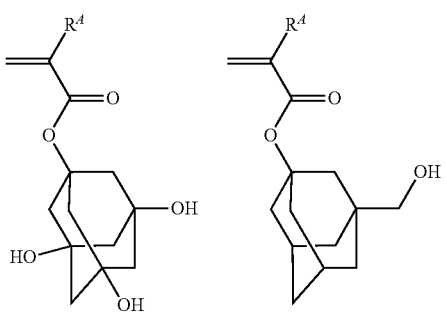
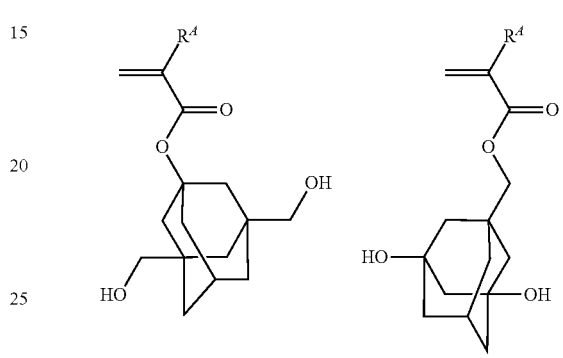
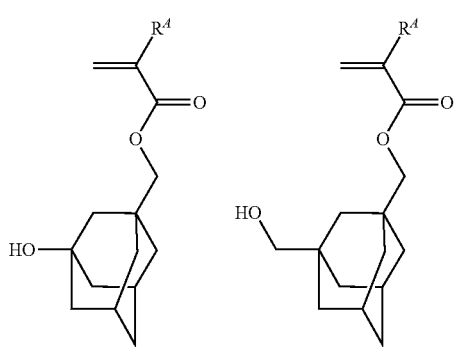
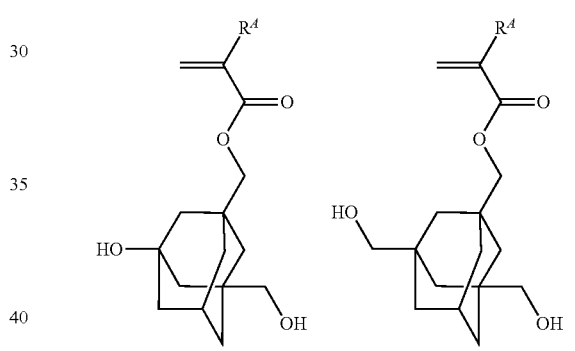
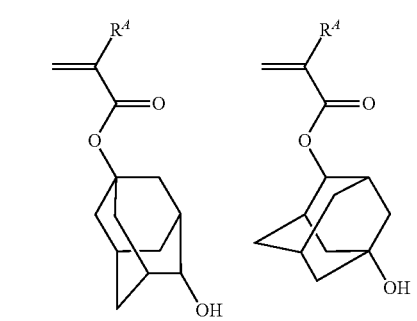
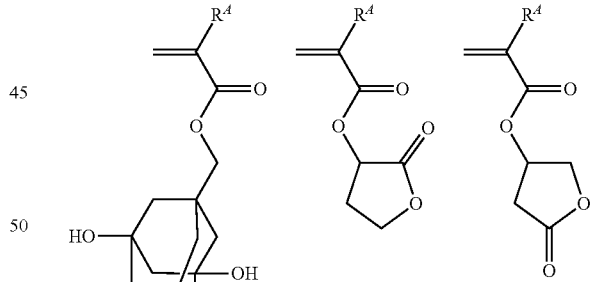
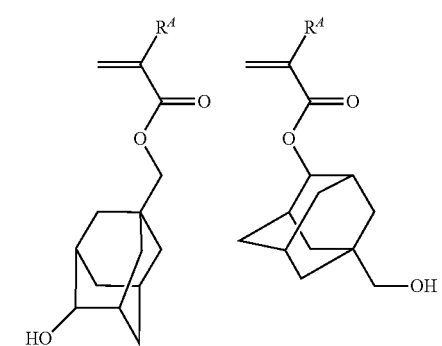
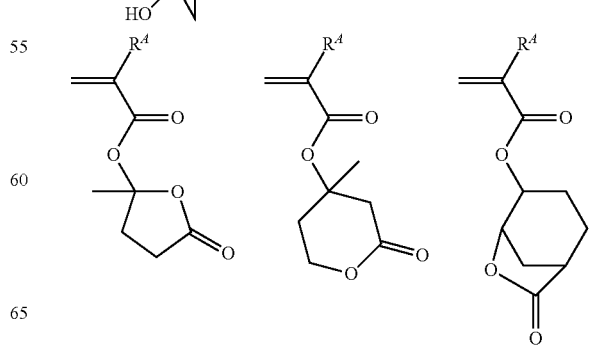

-continued
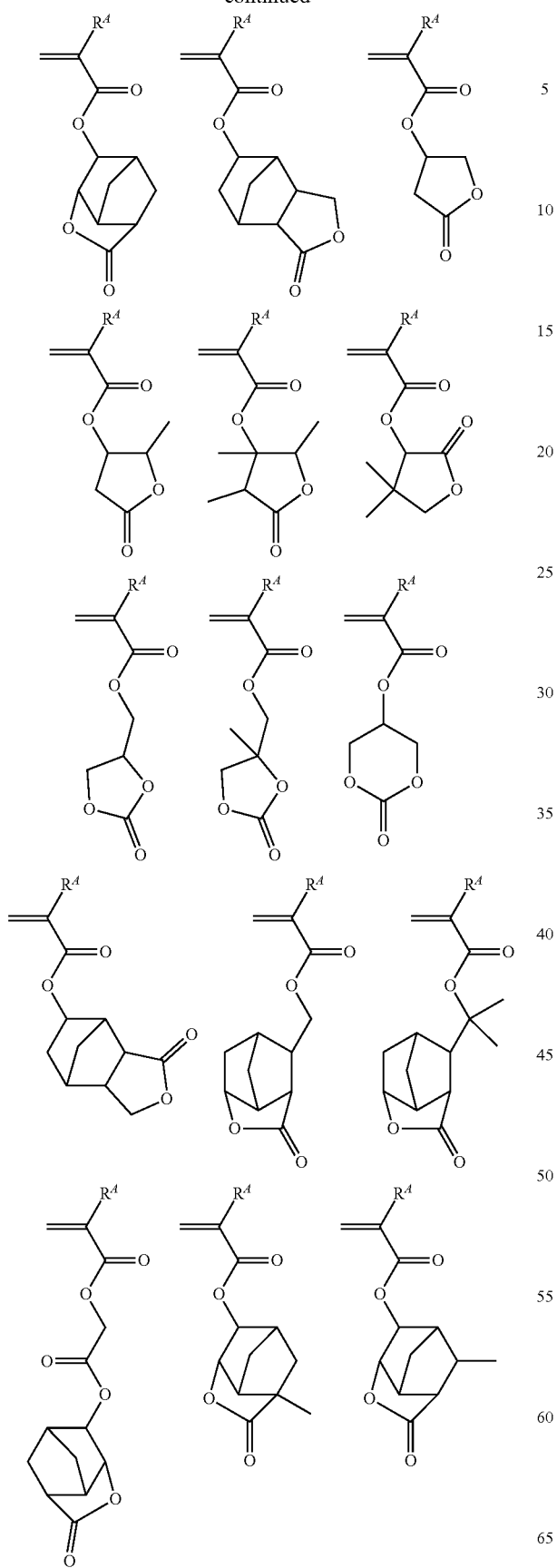
-continued
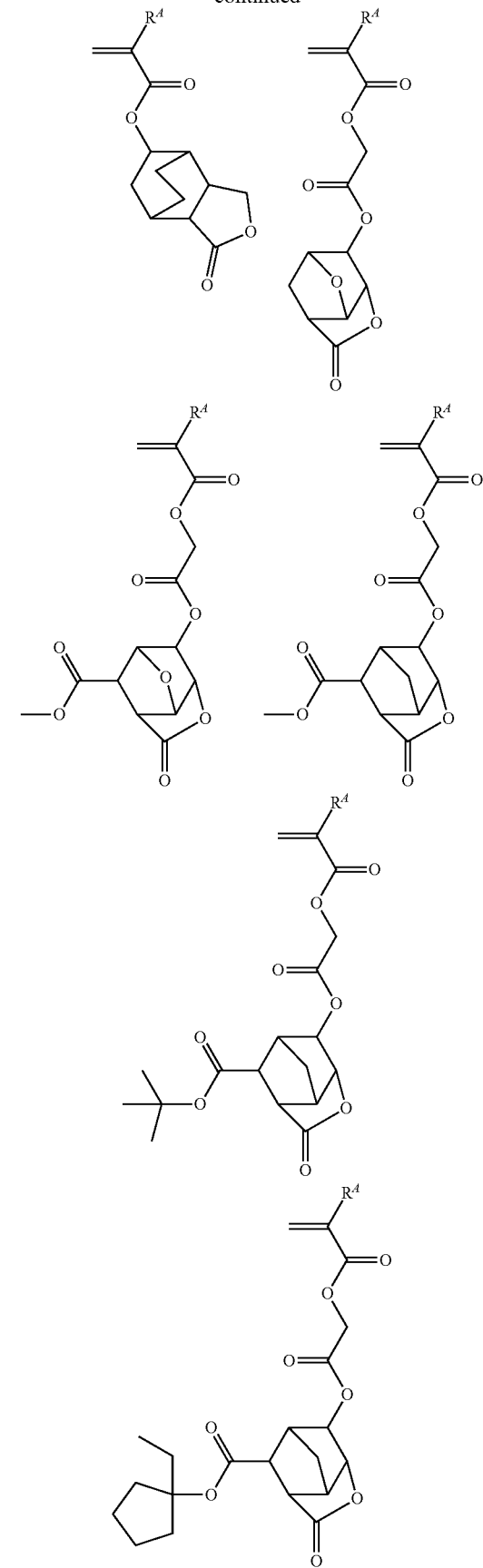

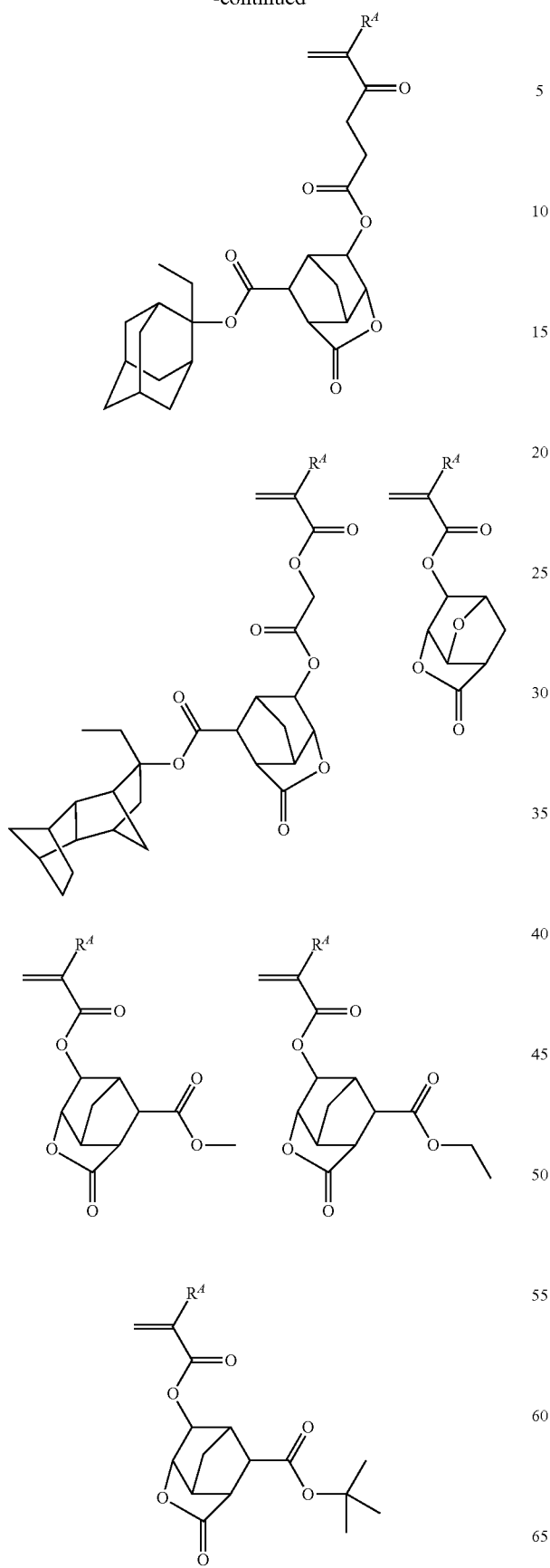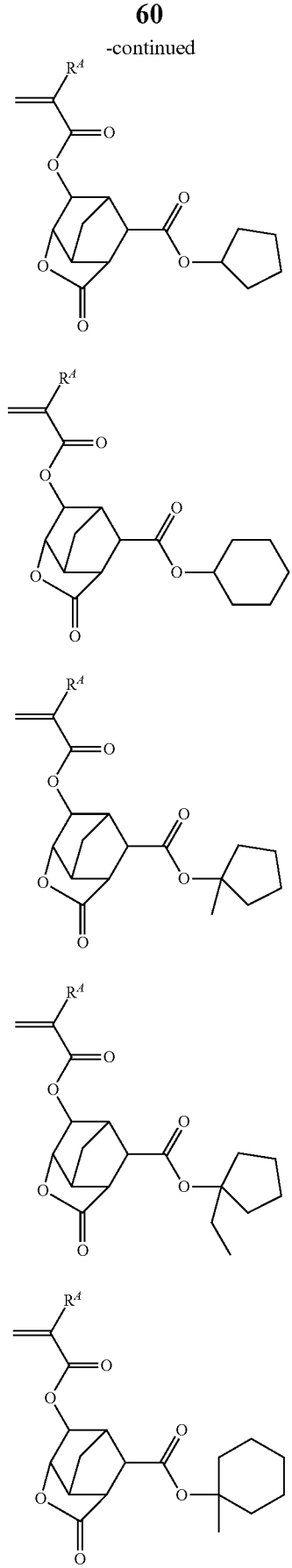

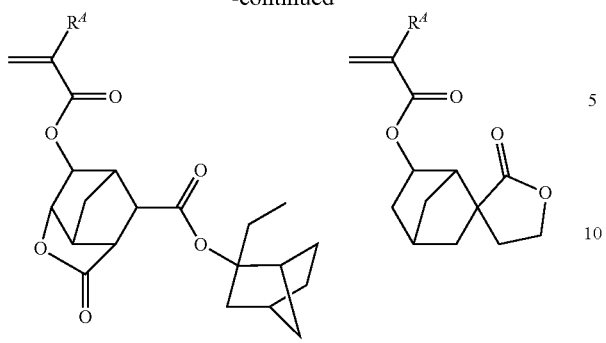
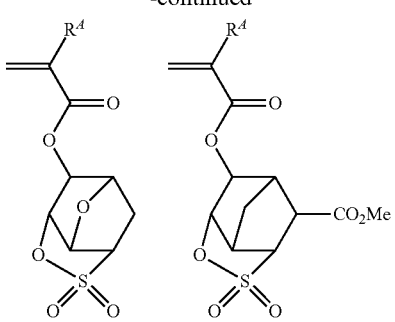

-continued

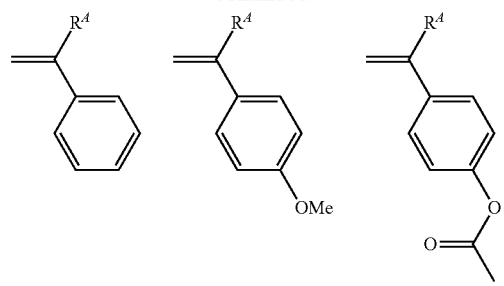

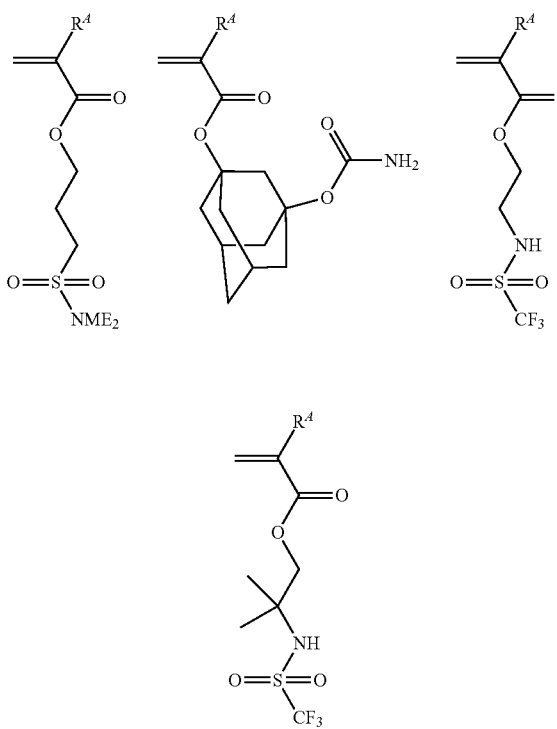

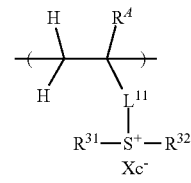

(F1)

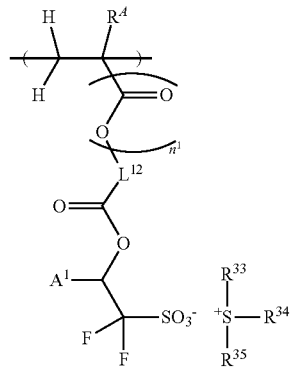

(F2)

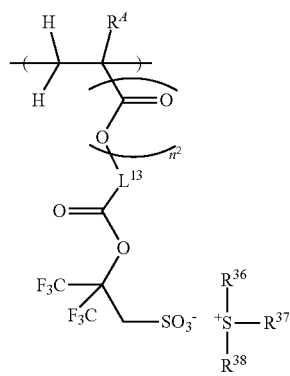

(F3)

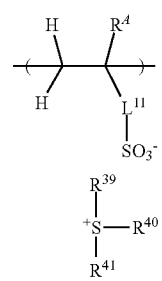

(F4)

In the embodiment wherein the base polymer is a polymer-bound acid generator, the base polymer further comprises recurring units of at least one type selected from recurring units having the formula (F1), recurring units having the formula (F2), recurring units having the formula (F3), ad reaming units having the formula (F4), all defined below. These recurring units are also referred to as recurring units (F1) to (F4), respectively. Where the resist composition contains an acid generator of addition type, which will be described later, the base polymer may or may not comprise recurring units (F1) to (F4).

In formulae (F1) to (F4), $R^A$ is hydrogen, fluorine, methyl or trifluoromethyl. $L^{11}$ is a single bond, phenylene, —O-$L^{11A}$-, —C(=O)—O-$L^{11A}$-, or —C(=O)—NH-$L^{11A}$-, wherein $L^{11A}$ is a $C_1$-$C_{20}$ alkanediyl, $C_1$-$C_{20}$ alkenediyl, or phenylene group which may contain a heteroatom. $L^{12}$ and $L^{13}$ are each independently a single bond or a $C_1$-$C_{20}$ divalent hydrocarbon group which may contain a heteroatom. $L^{14}$ is a single bond, methylene, ethylene, phenylene, fluorinated phenylene, —O-$L^{14A}$-, —C(=O)O-$L^{14A}$-, or —C(O)—NH-$L^{14A}$-, wherein $L^{14A}$ is an optionally substituted phenylene group.

The alkanediyl group $L^{11A}$ may be straight, branched or cyclic and examples thereof include methylene, ethane-1,1-diyl, ethane-1,2-diyl, propane-1,2-diyl, propane-2,2-diyl, propane-1,3-diyl, 2-methylpropane-1,3-diyl, butane-1,3-diyl, butan-2,3-diyl, butane-1,4-diyl, pentane-1,3-diyl, pentane-1,4-diyl, 2,2-dimethylpropane-1,3-diyl, pentane-1,5- diyl, hexane-1,6-diyl, cyclopentane-1,2-diyl, cyclopentane-1,3-diyl, and cyclohexane-1,4-diyl. The alkenediyl group $L^{11}$ may be straight, branched or cyclic and examples thereof include ethene-1,2-diyl, 1-propene-1,3-diyl, 2-butene-1,4-diyl, 1-methy-1-butene-1,4-diyl, and 2-cyclohexene-1,4-diyl.

The divalent hydrocarbon groups $L^{12}$ and $L^{13}$ may be straight, branched or cyclic and examples thereof include alkanediyl and alkenediyl groups as exemplified above.

In formulae (F1) to (F4), $R^{31}$ to $R^{41}$ are each independently a $C_1$-$C_{20}$ monovalent hydrocarbon group which may contain a heteroatom. The monovalent hydrocarbon group may be straight, branched or cyclic. Examples thereof include, but are not limited to, alkyl groups such as methyl, ethyl, n-propyl, isopropyl, n-butyl, and tert-butyl; monovalent saturated alicyclic hydrocarbon groups such as cyclopropyl, cyclopentyl, cyclohexyl, cyclopropylmethyl, 4-methylcyclohexyl, cyclohexylmethyl, norbornyl, and adamantyl; alkenyl groups such as vinyl, allyl, propenyl, butenyl and hexenyl; monovalent unsaturated alicyclic hydrocarbon groups such as cyclohexenyl; aryl groups such as phenyl and naphthyl heteroaryl groups such as thienyl; and aralkyl groups such as benzyl, 1-phenylethyl and 2-phenylethyl. Of these, aryl groups are preferred. In these groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic anhydride or haloalkyl moiety.

Any two of $L^{11}$, $R^{31}$ and $R^{32}$ may bond together to form a ring with the sulfur atom to which they are attached. Any two of $R^{33}$, $R^{34}$ and $R^{35}$, any two of $R^{36}$, $R^{37}$ and $R^{38}$, or any two of $R^{39}$, $R^{40}$ and $R^{41}$ may bond together to form a ring with the sulfur atom to which they are attached.

In formula (F1), $Xc^-$ is a non-nucleophilic counter ion. Examples of the non-nucleophilic counter ion include halide ions such as chloride and bromide ions; fluoroalkylsulfonate ions such as triflate, 1,1,1-trifluoromethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; methide ions such as tris(trifluoromethylsulfonyl)methide and tris(perfluoroethylsulfonyl)methide.

Also included are anions having the formulae (F5) and (F6).

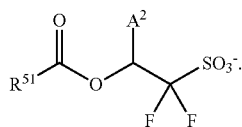

(F5)

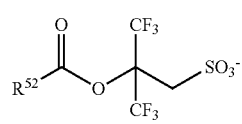

(F6)

In formulae (F5) and (F6), $R^{51}$ and $R^{52}$ are each independently a $C_1$-$C_{40}$ monovalent hydrocarbon group which may contain a heteroatom. $A^2$ is hydrogen or trifluoromethyl. The $C_1$-$C_{40}$ monovalent hydrocarbon group may be straight, branched or cyclic.

In formula (F2), $A^1$ is hydrogen or trifluoromethyl. Exemplary structures of the anion in formula (F2) include those described in JP-A 2014-177407, paragraphs [0021]-[0026]. Exemplary structures of the anion in formula (2) wherein $A^1$ is hydrogen include those described in JP-A 2010-116550, paragraphs [0021]-[0028]. Exemplary structures of the anion in formula (F2) wherein $A^1$ is trifluoromethyl include those described in JP-A 2010-077404, paragraphs [0021]-[0027].

Exemplary structures of the anion in formula (F3) include those examples of formula (F2) wherein —CH($A^1$)CF$_2$SO$_3^-$ is replaced by —C(CF$_3$)$_2$CH$_2$SO$_3^-$.

Preferred examples of the anion in the monomer from which recurring it (F2) we derived are shown below, but not limited thereto. Herein $A^1$ is as defined above.

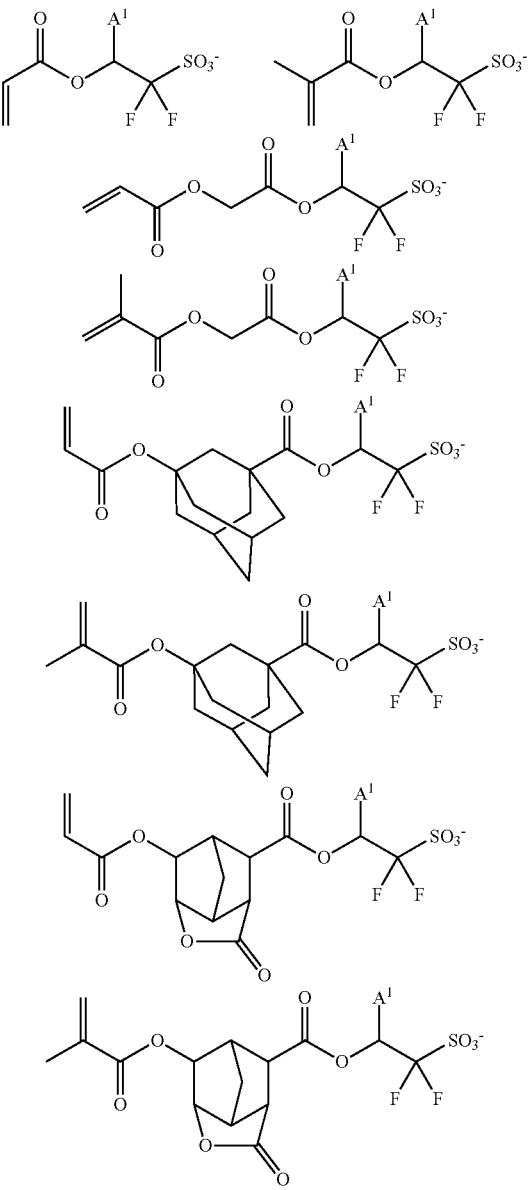

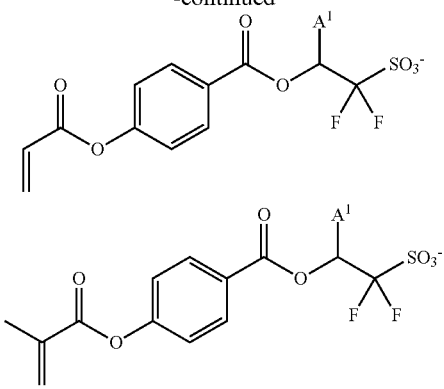
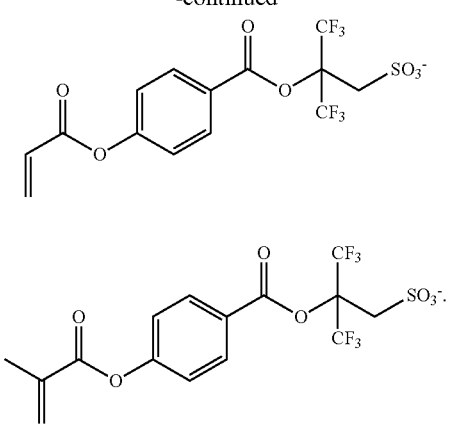
Preferred examples of the anion in the monomer from which recurring units (F3) we derived are shown below, but not limited thereto.
Examples of the sulfonium cation in formulae (F2) to (F4) are shown below, but not limited thereto.
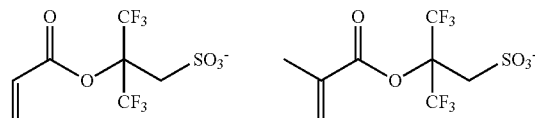
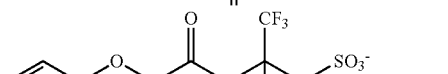
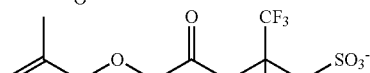
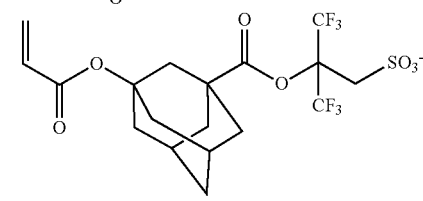
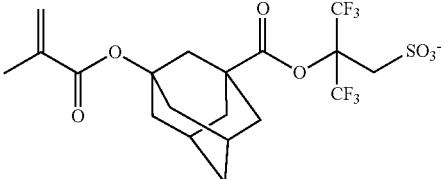
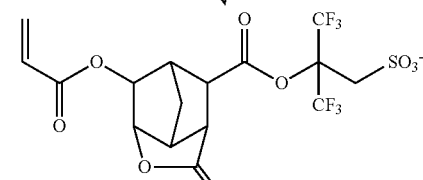
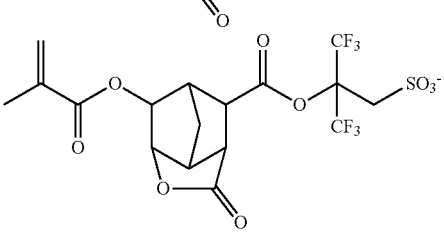
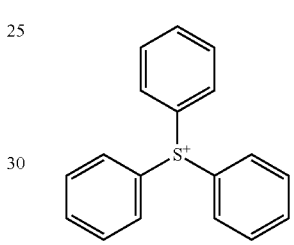
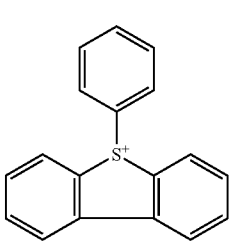
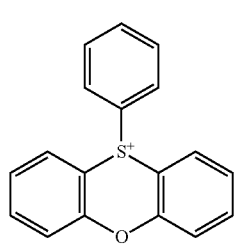
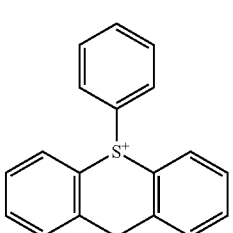
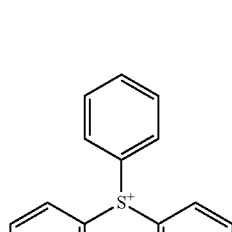
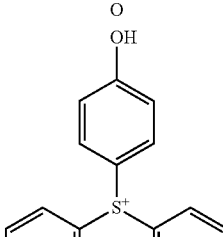
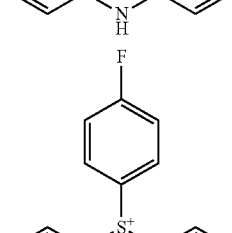
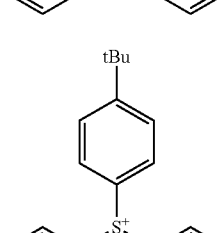

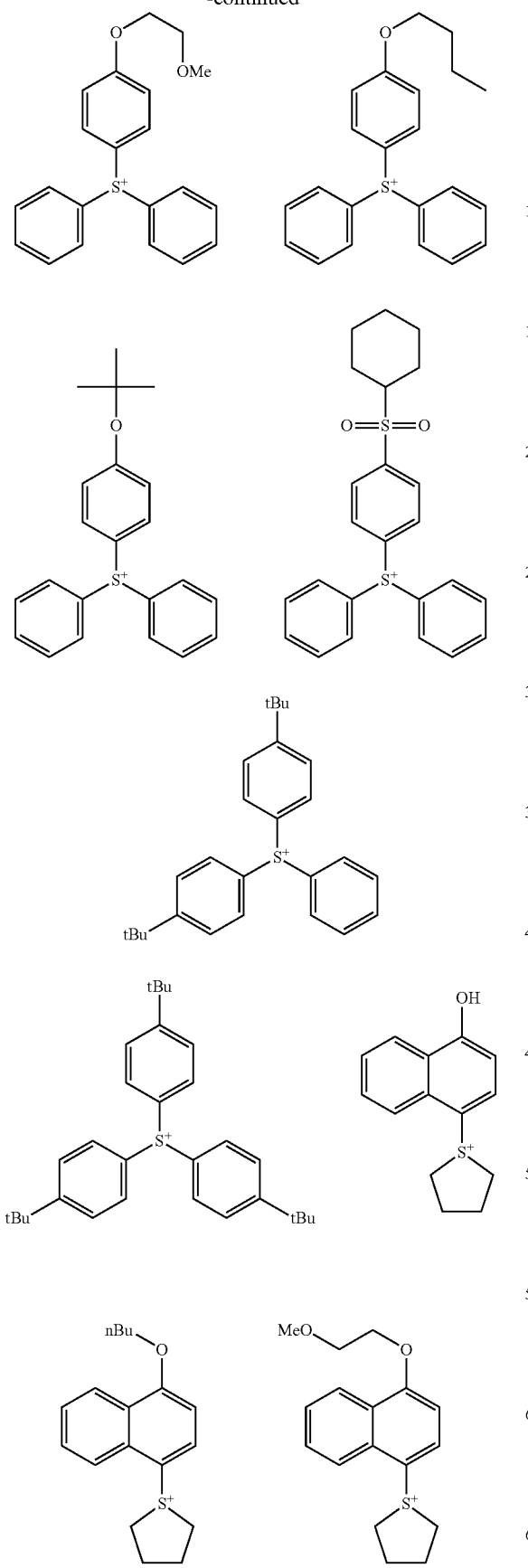

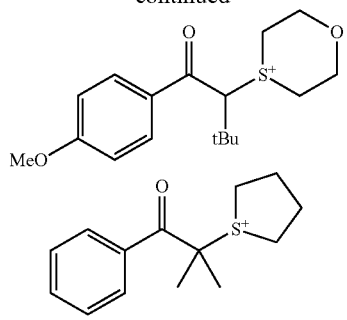

The recurring units (F1) to (F4) have an acid generator function. The base polymer comprising the same also functions as an acid generator. When the base polymer comprising recurring units (F1) to (F4) is used, the acid generator of addition type may or may not be included.

In addition to the foregoing units, the base polymer may further comprise recurring units derived from other monomers having a carbon-carbon double bond, for example, substituted acrylates such as methyl methacrylate, methyl crotonate, dimethyl maleate, and dimethyl itaconate, unsaturated carboxylic acids such as maleic acid, fumaric acid, and itaconic acid, cyclic olefins such as norbornene, norbornene derivatives, tetracyclo[4.4.0.1$^{2,5}$.17$^{7,10}$]dodecene derivatives, unsaturated acid anhydrides such as itaconic anhydride, α-methylene-γ-butyrolactone, indene, acenaphthylene and the like.

While the base polymer comprises recurring units derived from monomers, the molar fractions of respective units preferably fall in the following range (mol %), but are not limited thereto:
(I) 1 to 98 mol %, more preferably 1 to 80 mol %, even more preferably 10 to 70 mol % of recurring units (A) of at least one type,
(II) 2 to 99 mol %, more preferably 2 to 80 mol %, even more preferably 2 to 70 mol % of recurring units of at least one type selected from units (B) to (E),
(III) 0 to 50 mol %, more preferably 0 to 30 mol %, and even more preferably 0 to 20 mol % of recurring units of at least one type selected from units (F1) to (F4), and
(IV) 0 to 97 mol %, more preferably 0 to 70 mol %, and even more preferably 0 to 50 mol % of other recurring units of at least one type.

The base polymer should preferably have a Mw of 1,000 to 500,000, more preferably 3,000 to 100,000. A Mw within the range ensures satisfactory etching resistance, a contrast before and after exposure, and satisfactory resolution. As used herein, Mw is measured versus polystyrene standards by GPC using tetrahydrofuran (THF) or N,N-dimethylformamide (DMF) solvent.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the polymer should preferably have a narrow dispersity (Mw/Mn) of 1.0 to 3.0, more preferably 1.0 to 2.5 in order to provide a resist composition suitable for micropatterning to a small feature size.

The base polymer may be used alone or in admixture.

Generally, the method of synthesizing the polymer involves the steps of feeding a solution of monomers providing any desired recurring units to a reactor and effecting polymerization reaction in the reactor.

For example, the polymer is synthesized by dissolving monomers in a solvent, adding a polymerization initiator to the monomer solution, and heating for polymerization. Examples of the solvent which can be used for polymerization include toluene, benzene, THF, diethyl ether, dioxane, cyclohexane, cyclopentane, methyl ethyl ketone (MEK), propylene glycol monomethyl ether acetate (PGMEA), and γ-butyrolactone (GBL). Examples of the polymerization initiator used herein include 2,2'-azobisisobutyronitrile (AIBN), 2,2'-azobis(2,4-dimethylvaleronitrile), dimethyl 2,2-azobis(2-methylpropionate), 1,1'-azobis(1-acetoxy-1-phenylethane), benzoyl peroxide, and lauroyl peroxide. The initiator is preferably added in an amount of 0.01 to 25 mol % based on the total of monomers to be polymerized. Preferably the reaction temperature is 50 to 150° C., more preferably 60 to 100° C. The reaction time is preferably 2 to 24 hours, more preferably 2 to 12 hours in view of production efficiency.

The polymerization initiator may be fed to the reactor either by adding the initiator to the monomer solution and feeding the solution to the reactor, or by preparing an initiator solution separate from the monomer solution and feeding the initiator solution and the monomer solution independently to the reactor. Since there is a possibility that in the standby duration, the initiator generates a radical which triggers polymerization reaction to form a ultra-high-molecular-weight polymer, it is preferred from the standpoint of quality control to prepare and add dropwise the monomer solution and the initiator solution separately. The acid labile group that has been incorporated in the monomer may be kept as such, or polymerization may be followed by protection or partial protection. During the polymer synthesis, any known chain transfer agent such as dodecyl mercaptan or 2-mercaptoethanol may be added for molecular weight control purpose. The amount of chain transfer agent added is preferably 0.01 to 20 mol % based on the total of monomers to be polymerized.

When hydroxystyrene or hydroxyvinylnaphthalene is copolymerized, one method is by dissolving hydroxystyrene or hydroxyvinylnaphthalene and another monomer in an organic solvent, adding a radical polymerization initiator thereto, and beating the solution for polymerization. In an alternative method, acetoxystyrene or acetoxyvinylnaphthalene is used instead, and after polymerization, the acetoxy group is deprotected by alkaline hydrolysis, for thereby converting the polymer product to polyhydroxystyrene or polyhydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The amounts of monomers in the monomer solution may be determined appropriate so as to provide the preferred fractions of recurring units.

It is described how to use the polymer obtained by the above preparation method. The reaction solution resulting from polymerization reaction may be used as the final product. Alternatively, the polymer may be recovered in powder form through a purifying step such as re-precipitation step of adding the reaction solution to a poor solvent and letting the polymer precipitate as powder, after which the polymer powder is used as the final product. It is preferred from the standpoints of operation efficiency and consistent quality to handle a polymer solution which is obtained by dissolving the powder polymer resulting from the purifying step in a solvent, as the final product. The solvents which can be used herein are described in JP-A 2008-111103, paragraphs [0144]-[0145] (U.S. Pat. No. 7,537,880). Exemplary solvents include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetone alcohol (DAA); ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactones such as γ-butyrolactone (GBL); and high-boiling alcohols such as diethylene glycol, propylene glycol, glycerol, 1,4-butanediol, and 1,3-butanediol, which may be used alone or in admixture.

The polymer solution preferably has a polymer concentration of 0.01 to 30% by weight, more preferably 0.1 to 20% by weight.

Prior to use, the reaction solution or polymer solution is preferably filtered through a filter. Filtration is effective for consistent quality because foreign particles and gel which can cause defects are removed.

Suitable materials of which the filter is made include fluorocarbon, cellulose, nylon, polyester, and hydrocarbon base materials. Preferred for the filtration of a resist composition are filters made of fluorocarbons commonly known as Teflon®, hydrocarbons such as polyethylene and polypropylene, and nylon. While the pore size of the filter may be selected appropriate to comply with the desired cleanness, the filter preferably has a pore size of up to 100 nm, more preferably up to 20 nm. A single filter may be used or a plurality of filters may be used in combination. Although the filtering method may be single pass of the solution, preferably the filtering step is repeated by flowing the solution in a circulating manner. In the polymer preparation process, the filtering step may be carried out any times, in any order and in any stage. The reaction solution as polymerized or the polymer solution may be filtered, preferably both are filtered.

Organic Solvent

Examples of the organic solvent used in the resist composition include ketones such as cyclohexanone, cyclopentanone, methyl-2-n-pentyl ketone, and diacetone alcohol (DAA); alcohols such as 3-methoxybutanol, 3-methyl-3-methoxybutanol, 1-methoxy-2-propanol, and 1-ethoxy-2-propanol; ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether, esters such as propylene glycol monomethyl ether acetate (PGMEA), propylene glycol monoethyl ether acetate, methyl lactate, ethyl lactate, n-butyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate, methyl 2-hydroxyisobutyrate, isopropyl 2-hydroxyisobutyrate, isobutyl 2-hydroxyisobutyrate, and n-butyl 2-hydroxyisobutyrate; and lactones such as γ-butyrolactone (GBL), which may be used alone or in admixture.

In the resist composition, the organic solvent is preferably used in an amount of 50 to 10,000 parts, and more preferably 100 to 5,000 parts by weight per 80 parts by weight of the base polymer.

Acid Generator

Where the base polymer is not a polymer-bound acid generator, the resist composition further comprises an acid generator, also referred to as "acid generator of addition type." Notably, where the base polymer is a polymer-bound acid generator, the resist composition may or may not comprise an acid generator of addition type.

The acid generator of addition type is typically a compound (PAG) capable of generating an acid upon exposure to actinic ray or radiation. Exemplary PAGs are described in JP-A 2008-111103, paragraphs [0122]-[0142] (U.S. Pat. No. 7,537,880). More preferred structures are described in JP-A 2014-001259, paragraphs [0088]-[0092], JP-A 2012-041320, paragraphs [0015]-[0017] (U.S. Pat. No. 8,535,869), and JP-A 2012-106986, paragraphs [0015]-[0029]. The PAGs capable of generating partially fluorinated sulfonic acids described in these patent documents are advantageous for use in the ArF lithography because the strength and diffusion length of generated acid are adequate.

The acid generator of addition type preferably generates a strong acid such as sulfonic acid, imide acid (imidic acid) or methide acid. As used herein, the strong acid refers to a compound having a sufficient acidity to induce deprotection reaction of an acid labile group on the base polymer. Of these, sulfonic acids which are fluorinated at α-position are most commonly used. The fluorination at α-position is not essential when the acid labile group is an acetal group susceptible to deprotection.

The acid generator of addition type is preferably selected from compounds having the formulae (AG1) and (AG2).

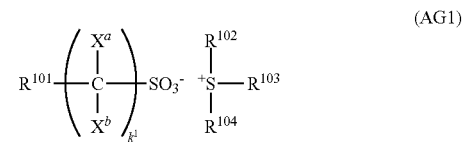

(AG1)

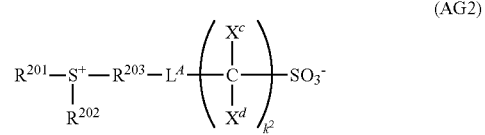

(AG2)

In formula (AG1), $R^{101}$ is hydrogen, fluorine or a $C_1$-$C_{35}$ monovalent hydrocarbon group which may contain a heteroatom. $R^{102}$, $R^{103}$ and $R^{104}$ are each independently a $C_1$-$C_{20}$ monovalent hydrocarbon group which may contain a heteroatom. Any two of $R^{102}$, $R^{103}$ and $R^{104}$ may bond together to form a ring with the sulfur atom to which they are attached.

The monovalent hydrocarbon group $R^{101}$ may be straight, branched or cyclic. Examples thereof include, but are not limited to, methyl, ethyl, propyl, isopropyl, butyl, isobutyl, sec-butyl, tert-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, eicosanyl, allyl, benzyl, diphenylmethyl, tetrahydrofuryl, methoxymethyl, ethoxymethyl, methylthiomethyl, acetamidomethyl, trifluoromethyl, (2-methoxyethoxy)methyl, acetoxymethyl, 2-carboxy-1-cyclohexyl, 2-oxopropyl, 4-oxo-1-adamantyl, and 3-oxocyclohexyl. In these groups, some hydrogen may be substituted by a moiety containing a heteroatom such as oxygen, sulfur, nitrogen or halogen, or a moiety containing a heteroatom such as oxygen, sulfur or nitrogen may intervene between carbon atoms, so that the group may contain a hydroxyl, cyano, carbonyl, ether bond, ester bond, sulfonic acid ester bond, carbonate bond, lactone ring, sultone ring, carboxylic anhydride or haloalkyl moiety.

In formula (AG2), $R^{201}$ and $R^{202}$ are each independently a $C_1$-$C_{20}$ monovalent hydrocarbon group which may contain a heteroatom. $R^{203}$ is a $C_1$-$C_{20}$ divalent hydrocarbon group which may contain a heteroatom. Any two of $R^{201}$, $R^{202}$ and $R^{203}$ may bond together to form a ring with the sulfur atom to which they are attached. $L^A$ is a single bond, ether bond or a $C_1$-$C_{20}$ divalent hydrocarbon group which may contain a heteroatom.

In formulae (AG1) and (AG2), $X^a$, $X^b$, $X^c$ and $X^d$ are each independently hydrogen, fluorine or trifluoromethyl, $k^1$ and $k^2$ are each independently an integer of 1 to 4.

The acid generator having formula (AG1) is preferably one having the formula (AG1'). The acid generator having formula (AG2) is preferably one having the formula (AG2').

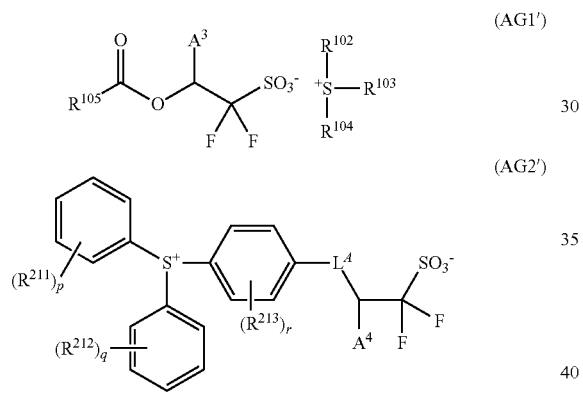

In formulae (AG1') and (AG2'), $R^{102}$, $R^{103}$, $R^{104}$, and $L^A$ are as defined above. $A^3$ and $A^4$ are each independently hydrogen or trifluoromethyl. $R^{105}$ is a $C_1$-$C_{35}$ monovalent hydrocarbon group which may contain a heteroatom. $R^{211}$, $R^{212}$ and $R^{213}$ are each independently hydrogen or a $C_1$-$C_{20}$ monovalent hydrocarbon group which may contain a heteroatom. The subscripts p and q are each independently an integer of 0 to 5, and r is an integer of 0 to 4.

In one preferred embodiment wherein the acid generator of addition type is an acid generator having formula (AG1') or (AG2'), more preferably wherein $A^3$ or $A^4$ is trifluoromethyl, for example, a line-and-space pattern with low LWR and improved acid diffusion length control or a hole pattern with good roundness and improved dimensional control is formed.

Examples of the acid generator having formula (AG1) are given below, but not limited thereto. Herein $A^3$ is as defined above.

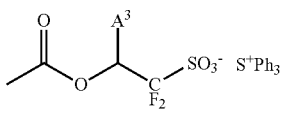

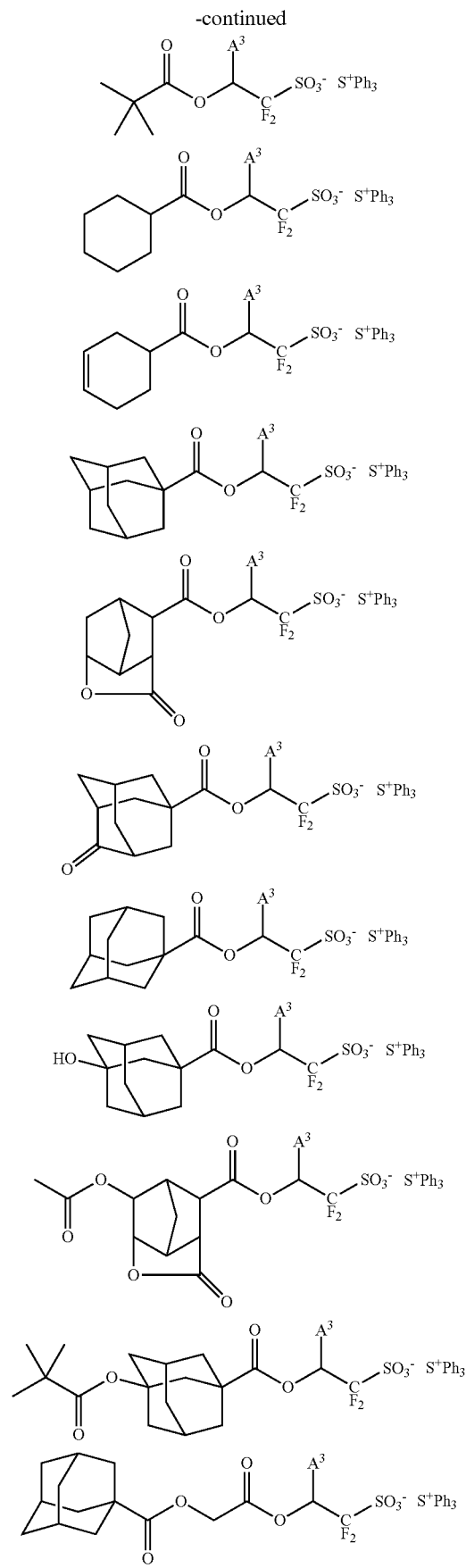

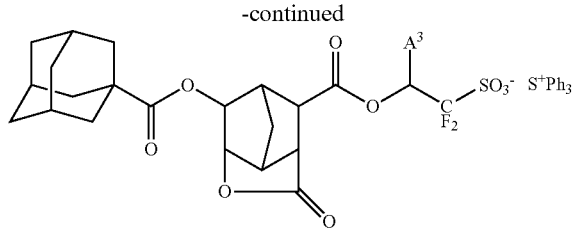
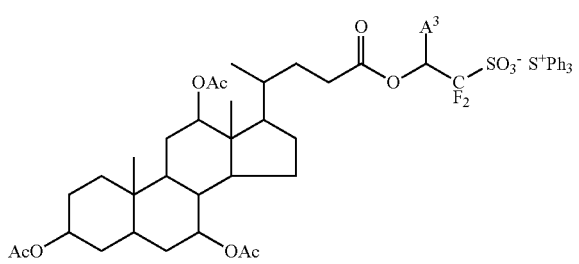
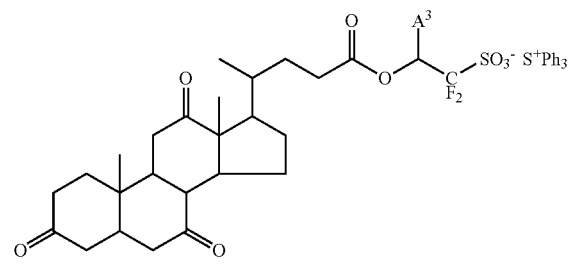
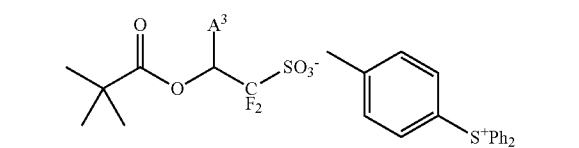
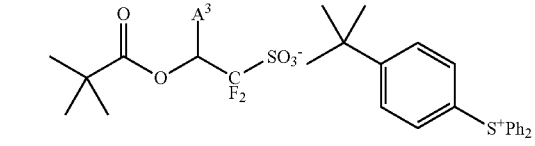
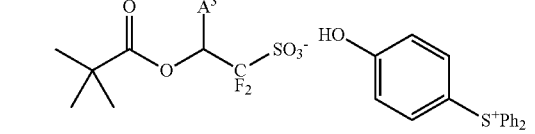
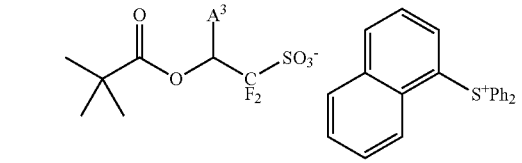
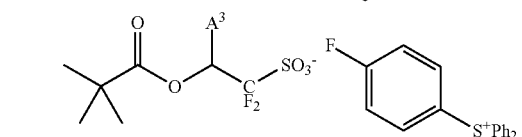
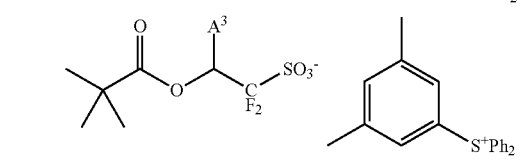
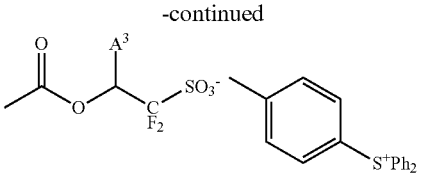
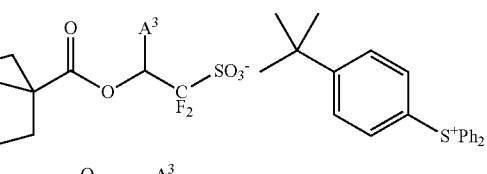
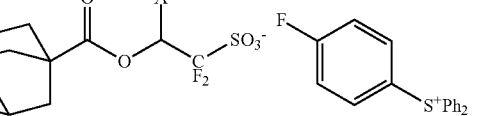
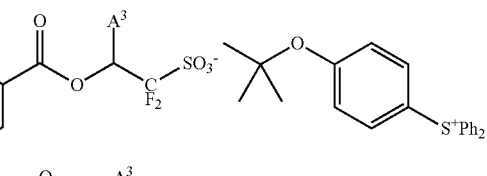
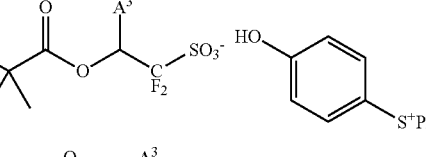
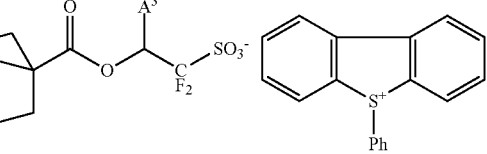
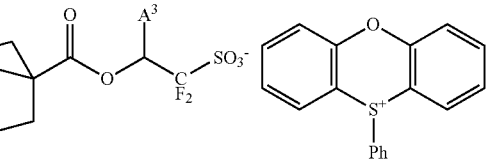
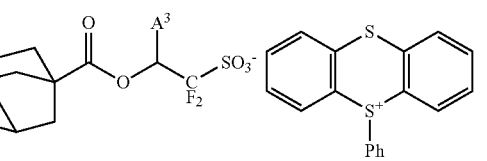
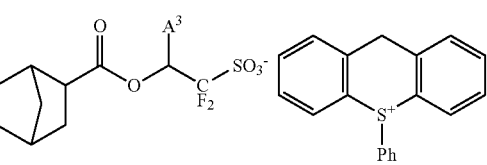
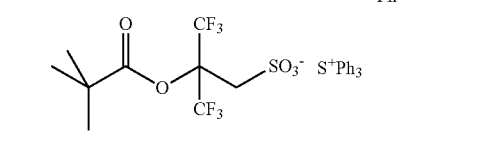
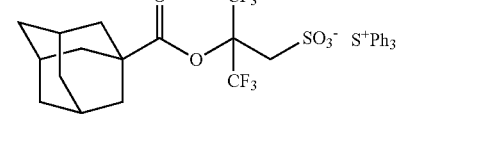

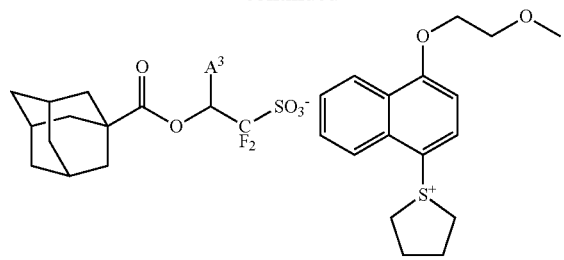
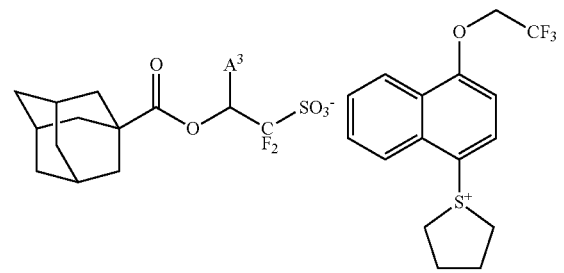
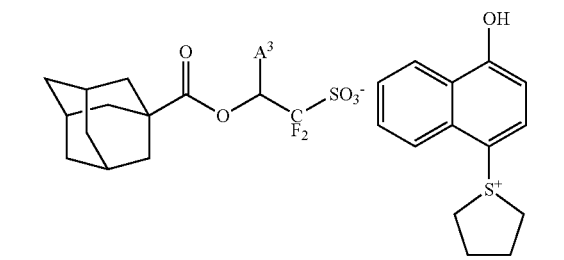
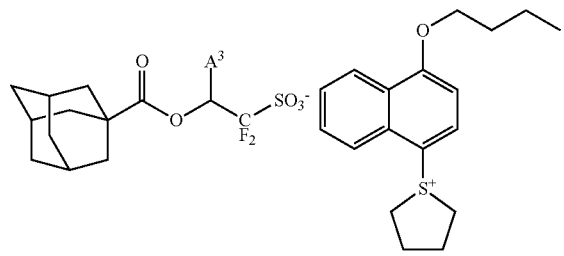
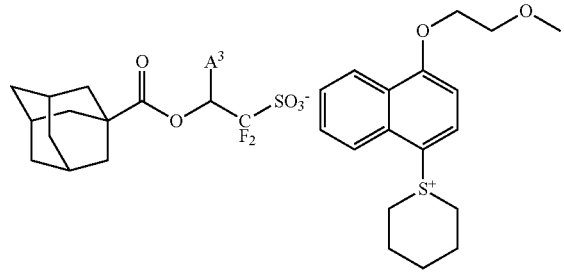
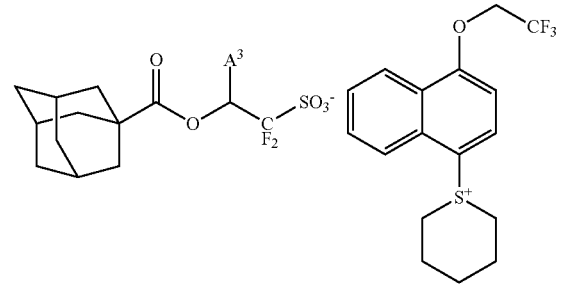
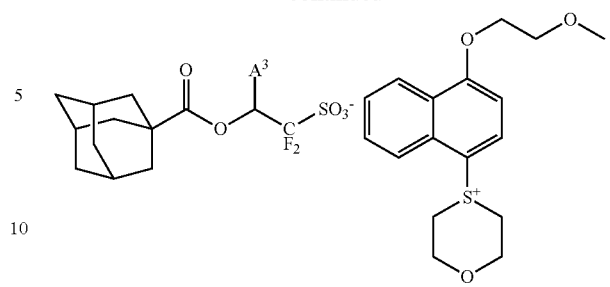
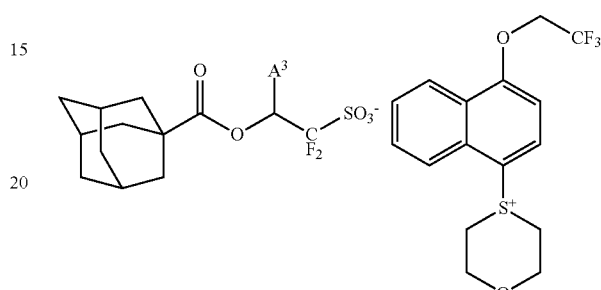
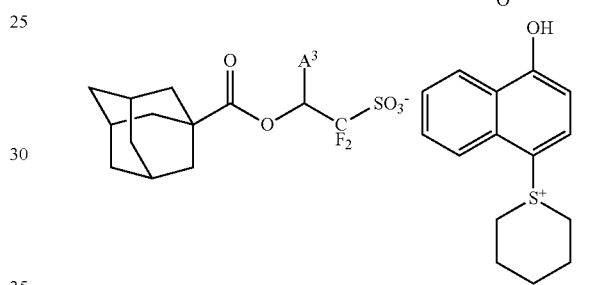
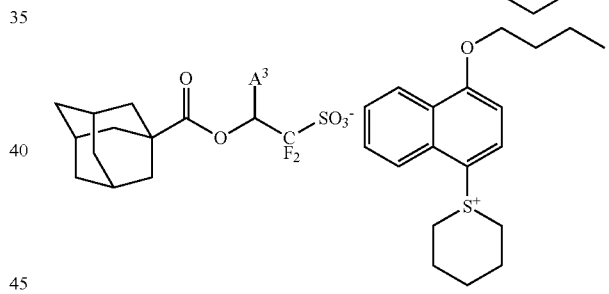
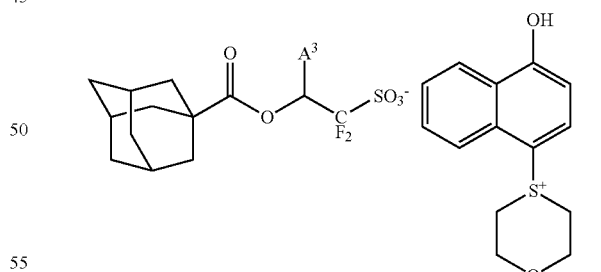
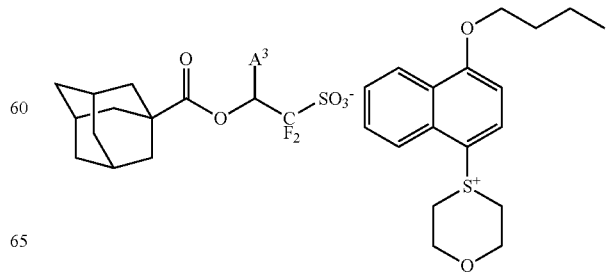

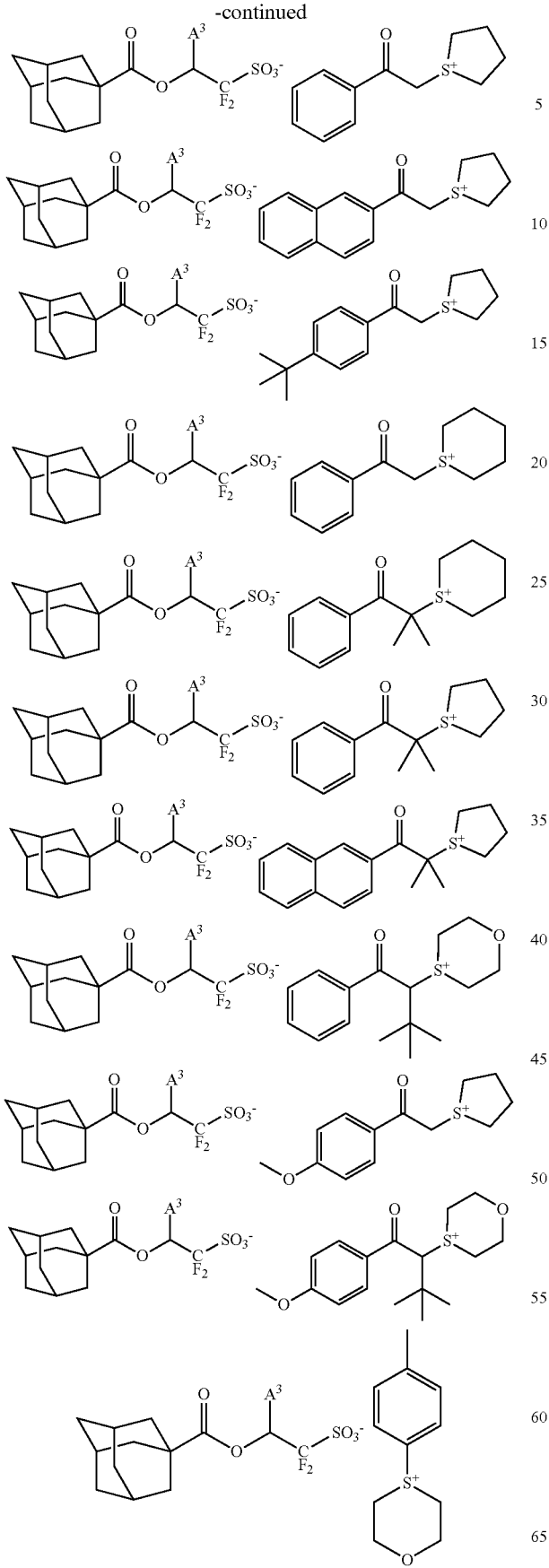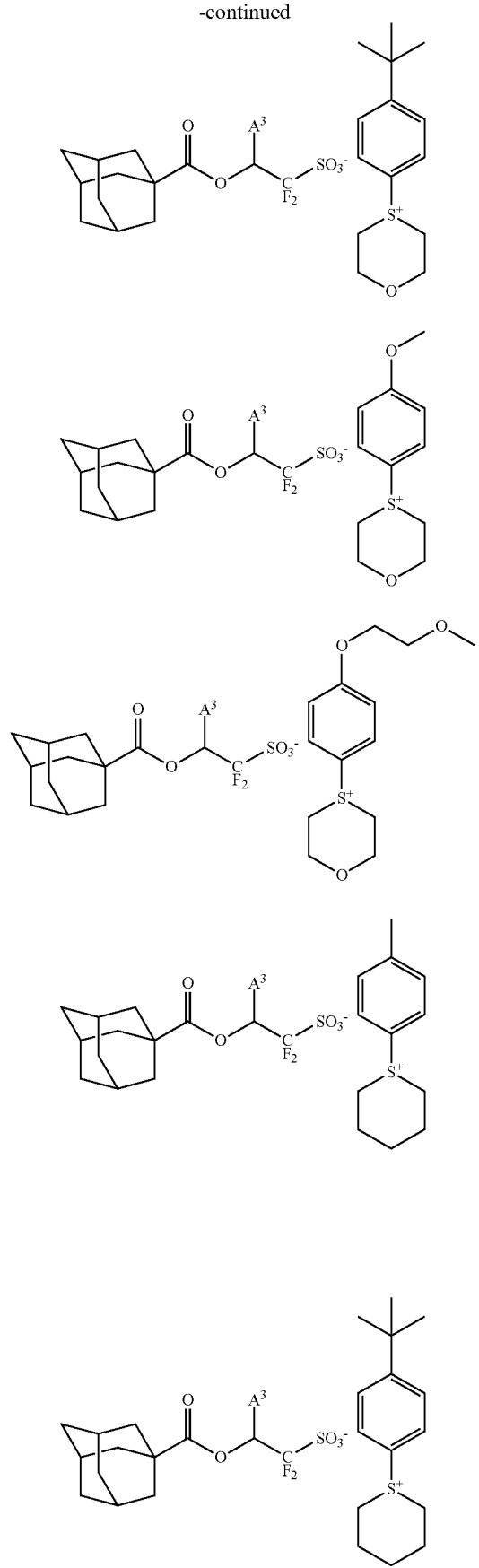

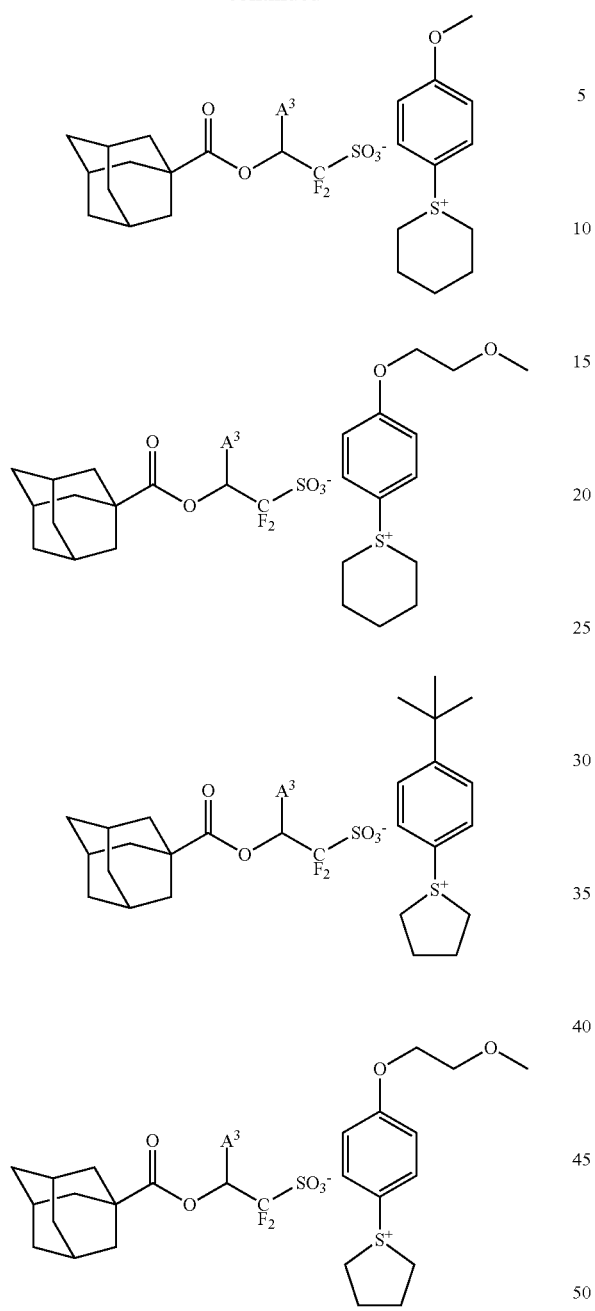
Examples of the acid generator having formula (AG2) are given below, but not limited thereto. Herein $A^4$ is as defined above.
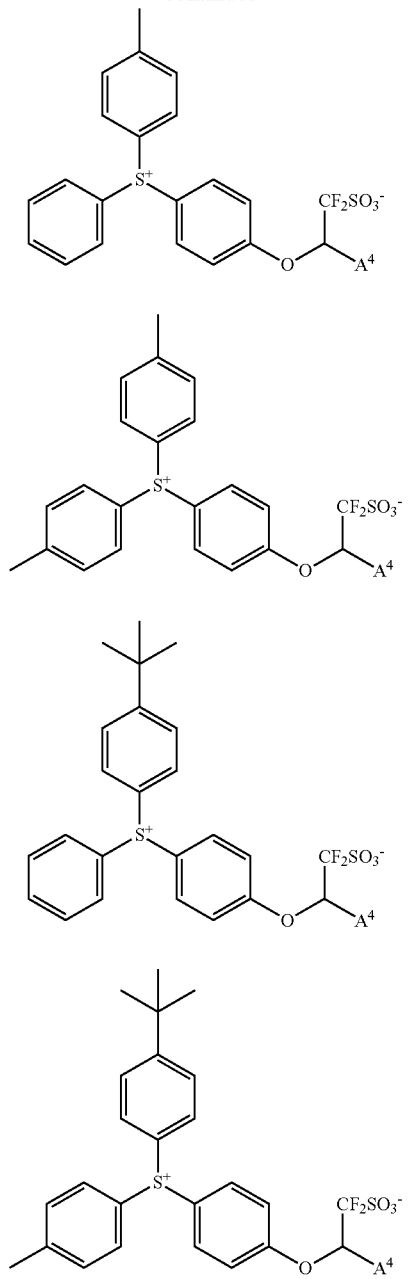

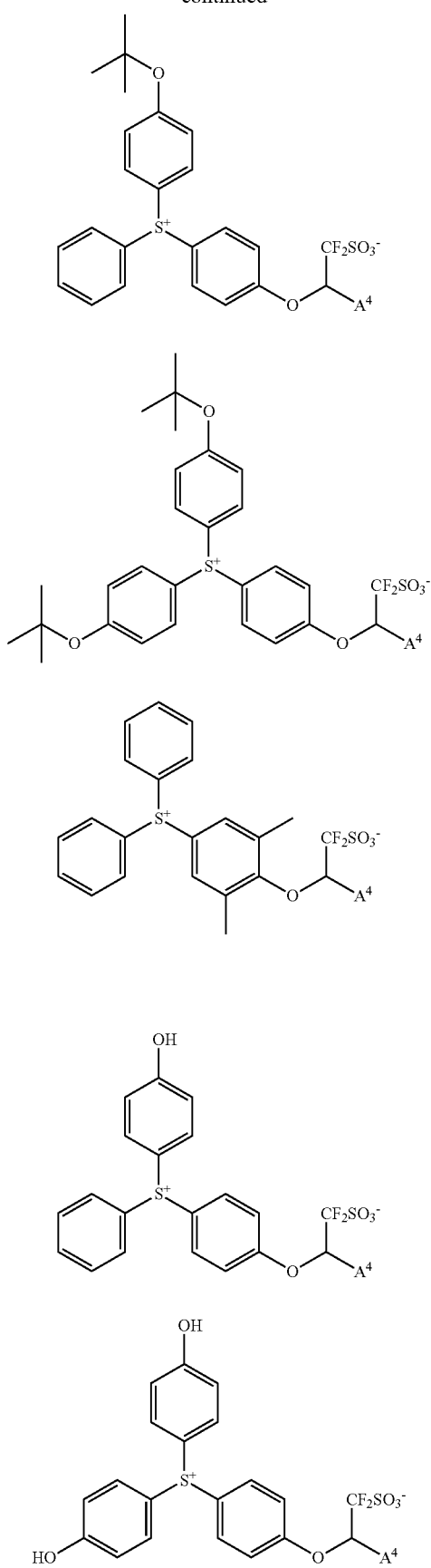
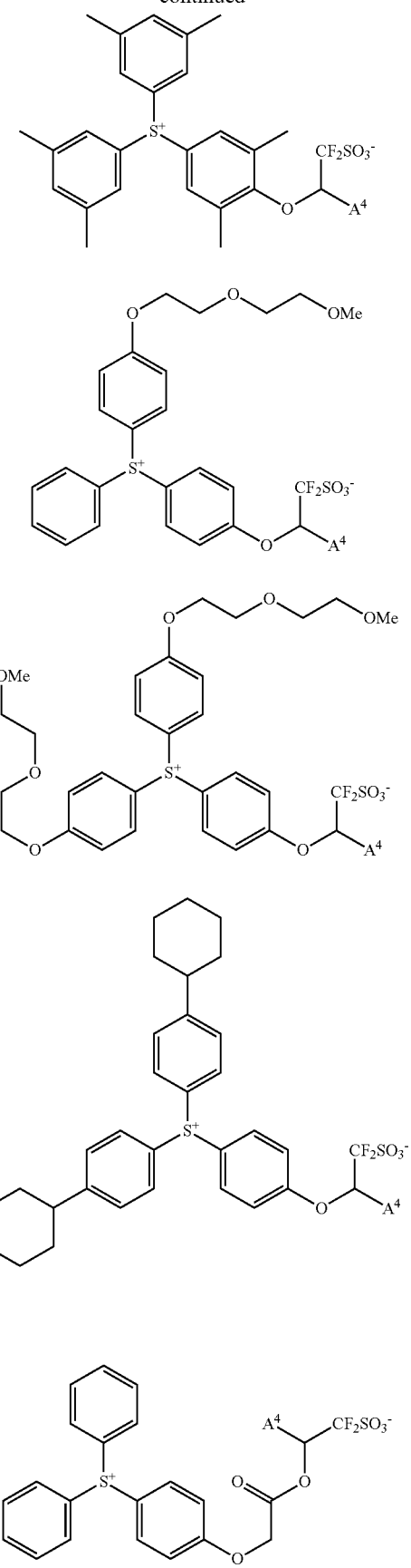

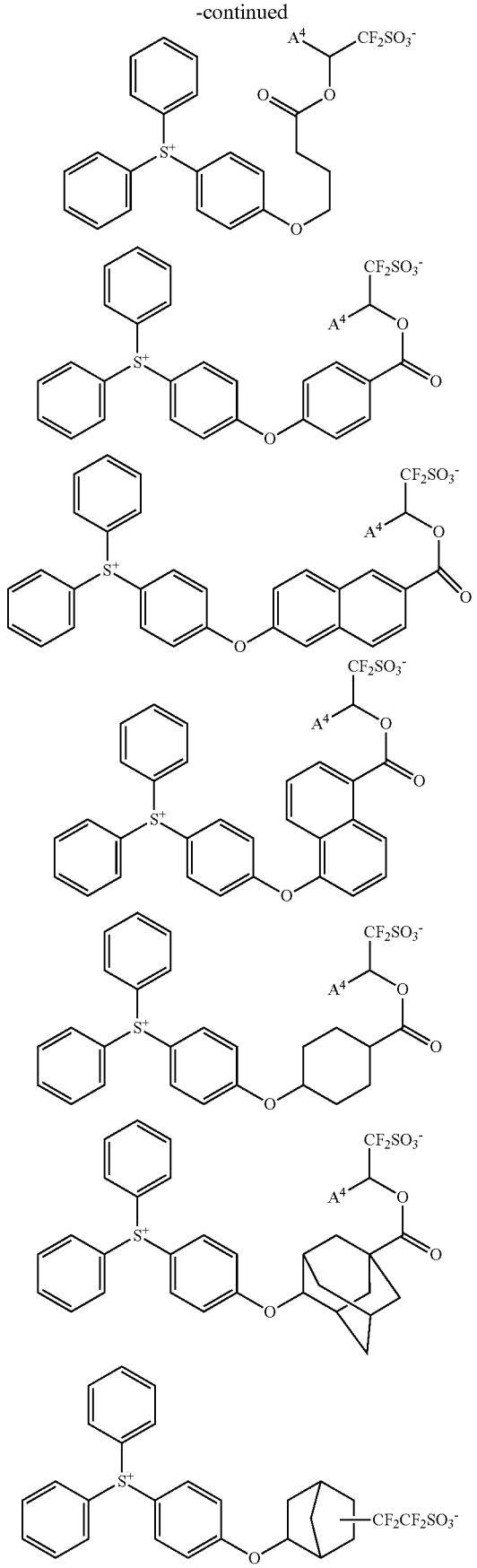
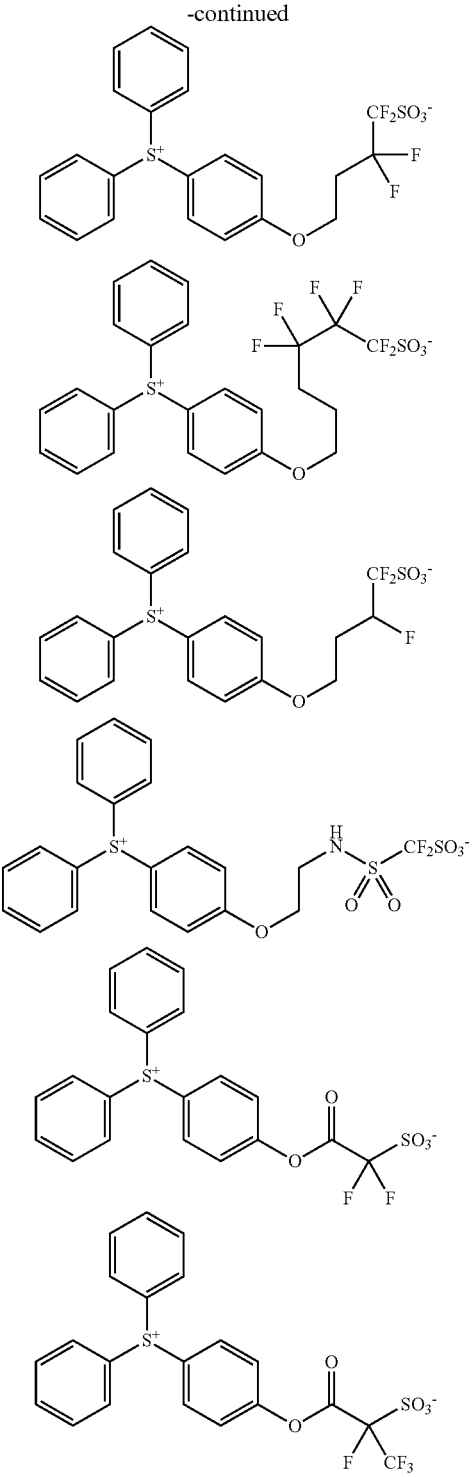

When the resist composition contains the acid generator of addition type, the amount thereof is preferably 0.5 to 30 parts by weight, more preferably 1 to 20 parts by weight per 80 puts by weight of the base polymer. When the base polymer contains recurring units (F1) to (F4) and/or the acid generator of addition type is added, the resist composition functions as a chemically amplified resist composition. The acid generator of addition type may be used alone or in admixture.

Quencher

The resist composition may further comprises a quencher or acid diffusion regulator. As used herein, the quencher refers to a compound capable of trapping the acid generated by the PAG in the resist composition to prevent the acid from diffusing to the unexposed region for thereby forming the desired pattern.

Examples of the quencher include primary, secondary, and tertiary amine compounds, specifically amine compounds having a hydroxyl group, ether bond, ester bond, lactone ring, cyano group or sulfonate bond as described in JP-A 2008-111103, paragraphs [0146]-[0164], and compounds having a carbamate group as described in JP 3790649.

Onium salts having the formulae (xa) and (xb) are also useful as the quencher.

$$R^{q1}-SO_3^- \quad Mq^+ \quad (xa)$$

$$R^{q2}-CO_2^- \quad Mq^+ \quad (xb)$$

In formula (xa), $R^{q1}$ is hydrogen or a $C_1$-$C_{40}$ monovalent hydrocarbon group which may contain a heteroatom, exclusive of the hydrocarbon group in which the hydrogen atoms bonded to the carbon atoms at α- and β-positions of the sulfone group are substituted by fluorine or fluoroalkyl. In formula (xb), $R^{q2}$ is hydrogen or a $C_1$-$C_{40}$ monovalent hydrocarbon group which may contain a heteroatom.

Examples of the monovalent hydrocarbon group $R^{q1}$ include methyl, ethyl, propyl, isopropyl, n-butyl, se-butyl, tert-butyl, tert-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2.6}$]decanyl, adamantyl, phenyl, naphthyl, and anthracenyl. In these groups, some hydrogen may be substituted by a moiety containing a heteroatom such as oxygen, sulfur, nitrogen or halogen, and a moiety containing a heteroatom such as oxygen, sulfur or nitrogen may intervene between carbon atoms, so that the group may contain a hydroxyl moiety, cyano moiety, carbonyl moiety, ether bond, ester bond, sulfonate bond, carbonate bond, lactone ring, sultone ring, carboxylic anhydride, or haloalkyl moiety.

Examples of the monovalent hydrocarbon group $R^{q2}$ as exemplified above for $R^{q1}$. Also included are fluorinated alkyl groups such as trifluromethyl and trifluoroethyl, and fluorinated aryl groups such as pentafluorophenyl and 4-trifluoromethylphenyl.

Illustrative structures of the anion in formula (xa) are shown below, but not limited thereto.

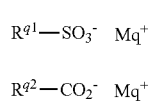

-continued

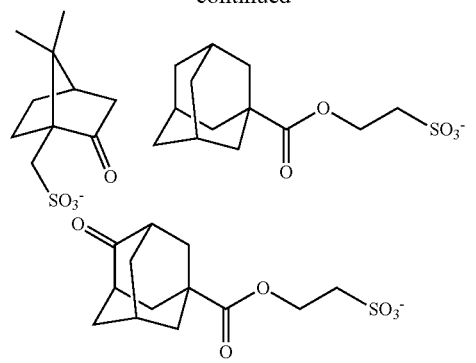

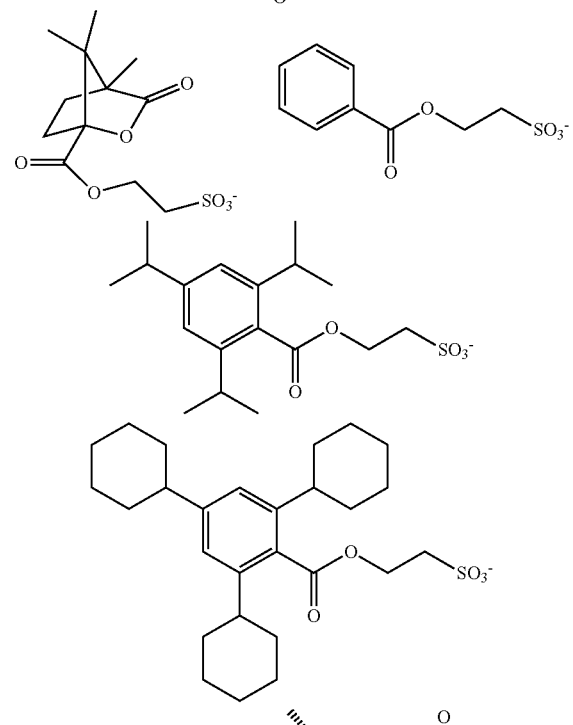

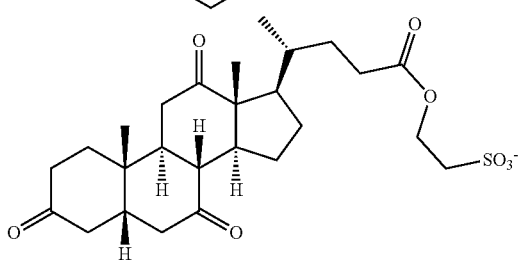

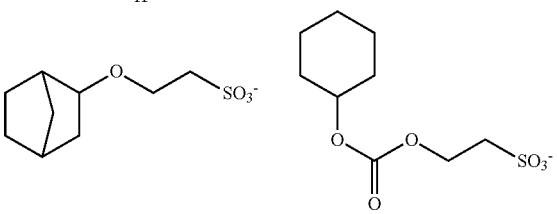

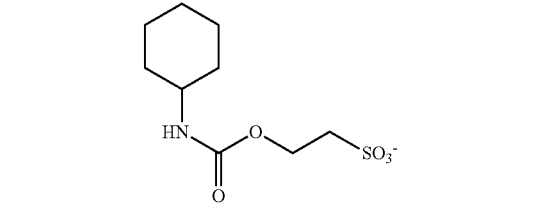

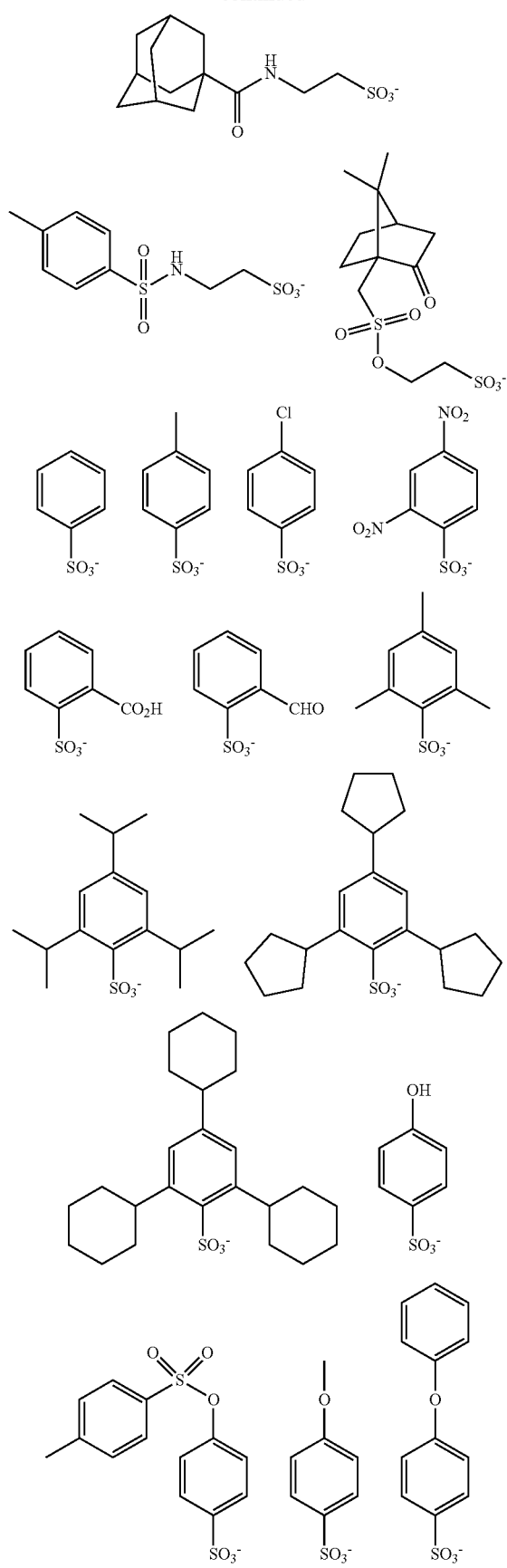
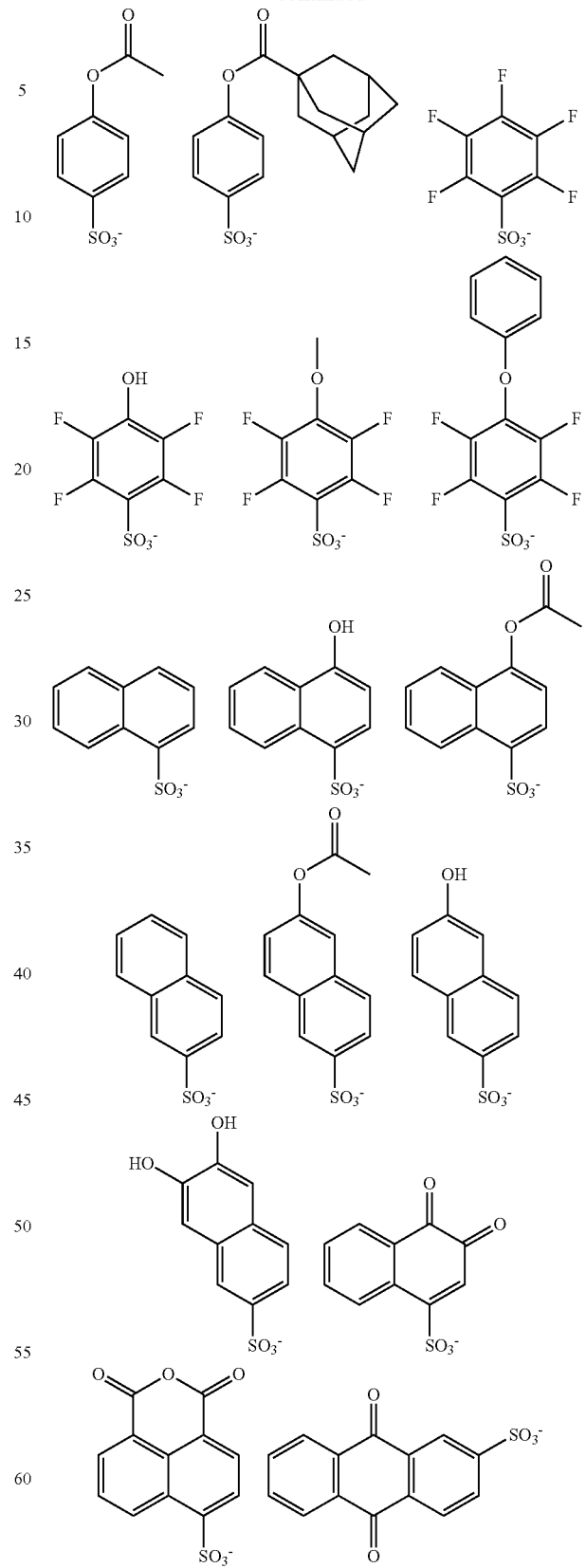
Illustrative structures of the anion in formula (xb) are shown below, but not limited thereto.

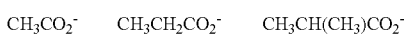
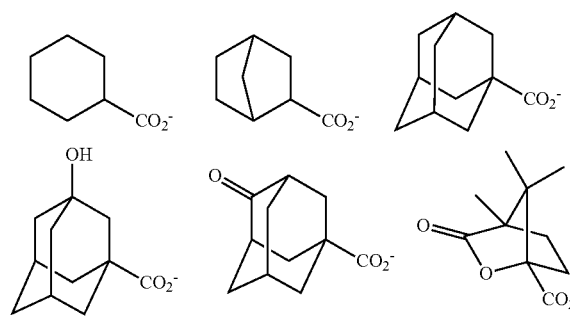
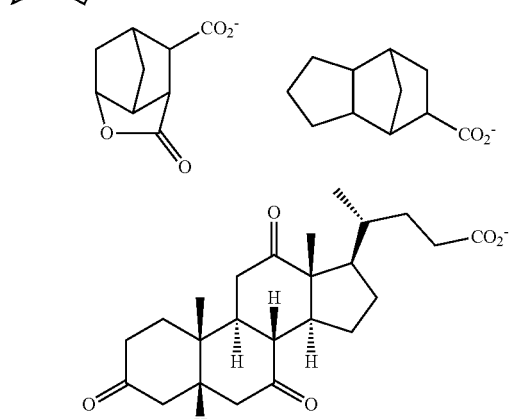
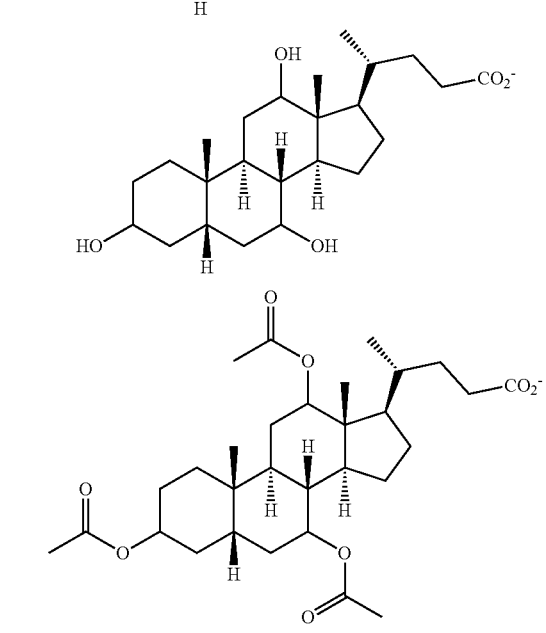
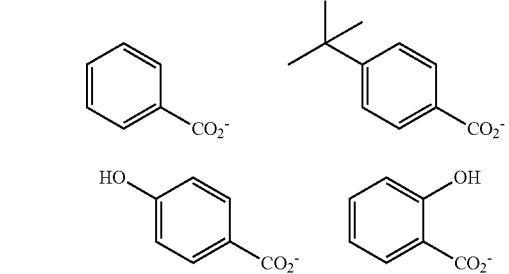
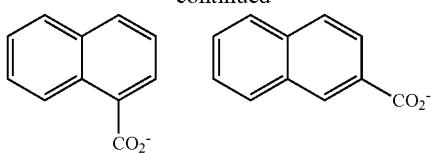
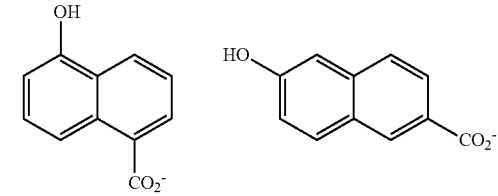
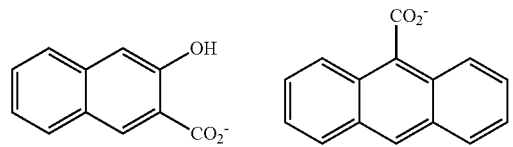
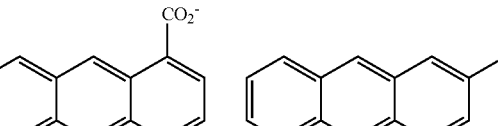
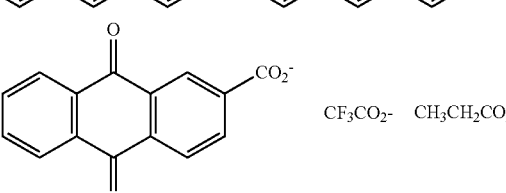
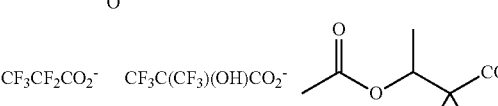
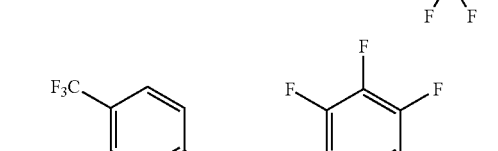
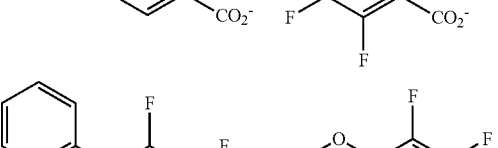
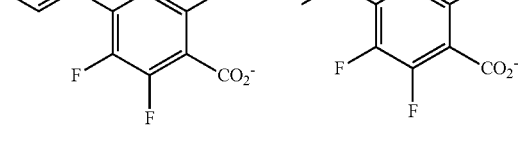
In formulae (xa) and (xb), Mq⁺ is an onium cation having the formula (c1), (c2) or (c3).
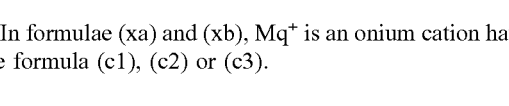 (c1)
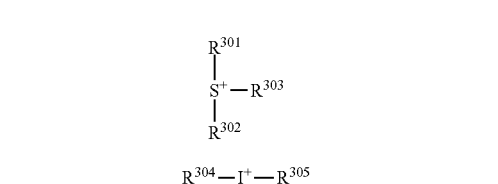 (c2)

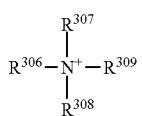
(c3)

In formulae (c1) to (c3), $R^{301}$, $R^{302}$, $R^{303}$, $R^{304}$, $R^{305}$, $R^{306}$, $R^{307}$, $R^{308}$, and $R^{309}$ are each independently a $C_1$-$C_{40}$ monovalent hydrocarbon group which may contain a heteroatom. A pair of $R^{301}$ and $R^{302}$ may bond together to form a ring with the sulfur atom to which they are attached. A pair of $R^{306}$ and $R^{307}$ may bond together to form a ring with the nitrogen atom to which they are attached. Examples of the monovalent hydrocarbon group represented by $R^{301}$ to $R^{309}$ are as exemplified above for $R^{q1}$ in formula (xa).

Examples of the cation moiety ($Mq^+$) in formulae (xa) and (xb) are shown below, but not limited thereto.

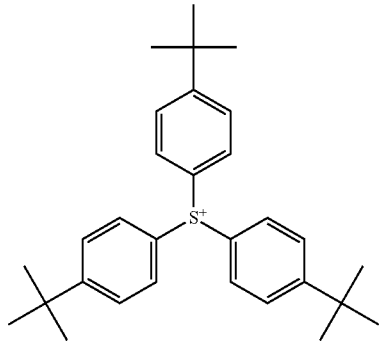

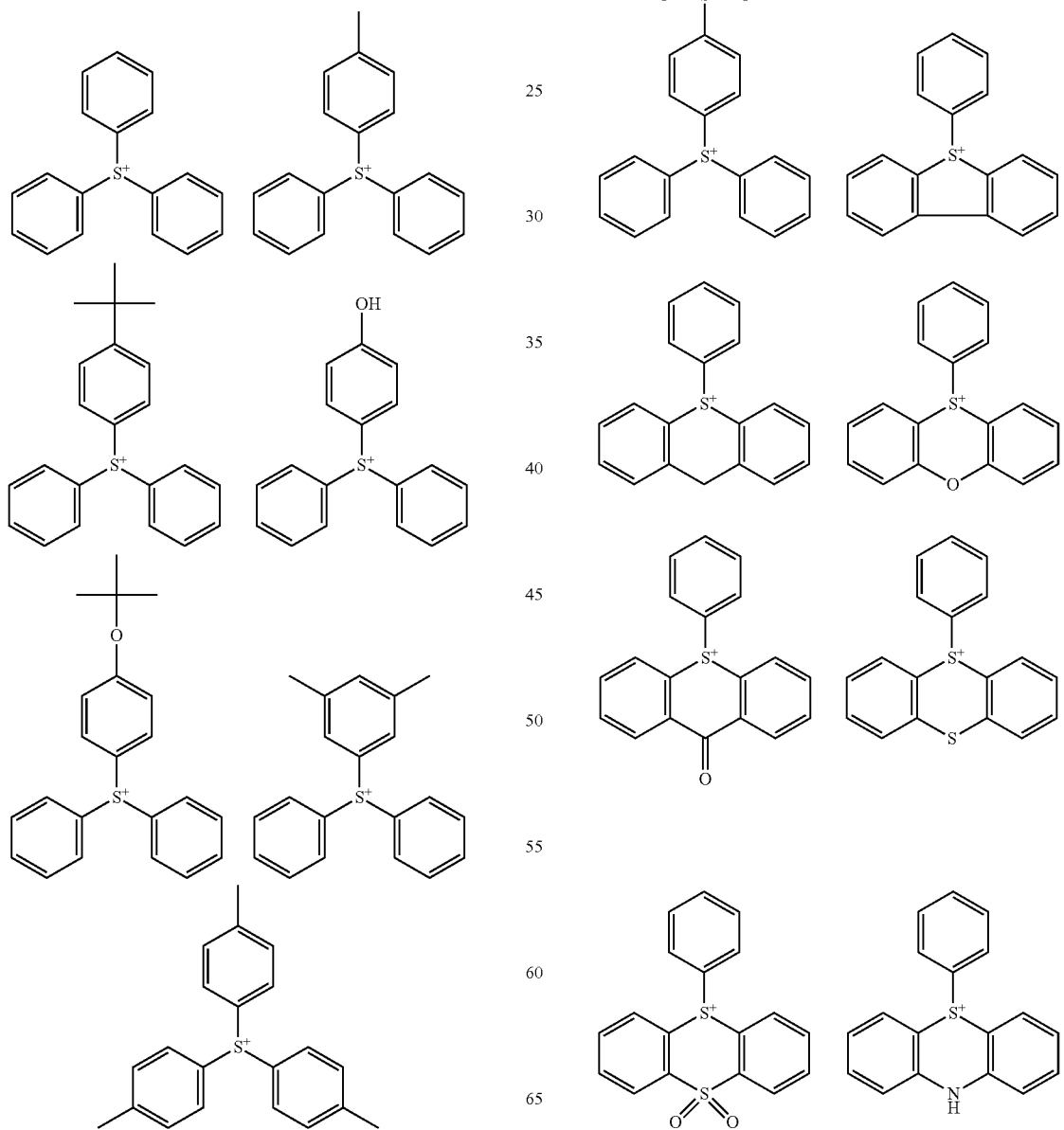

97
-continued
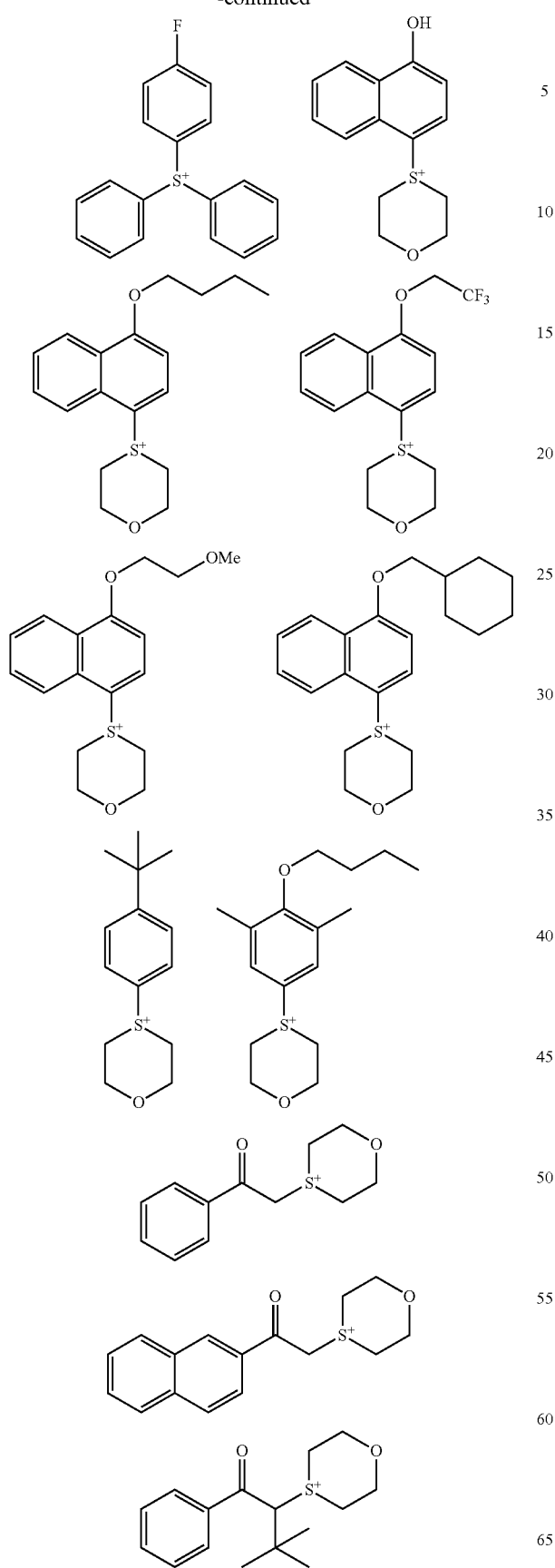
98
-continued
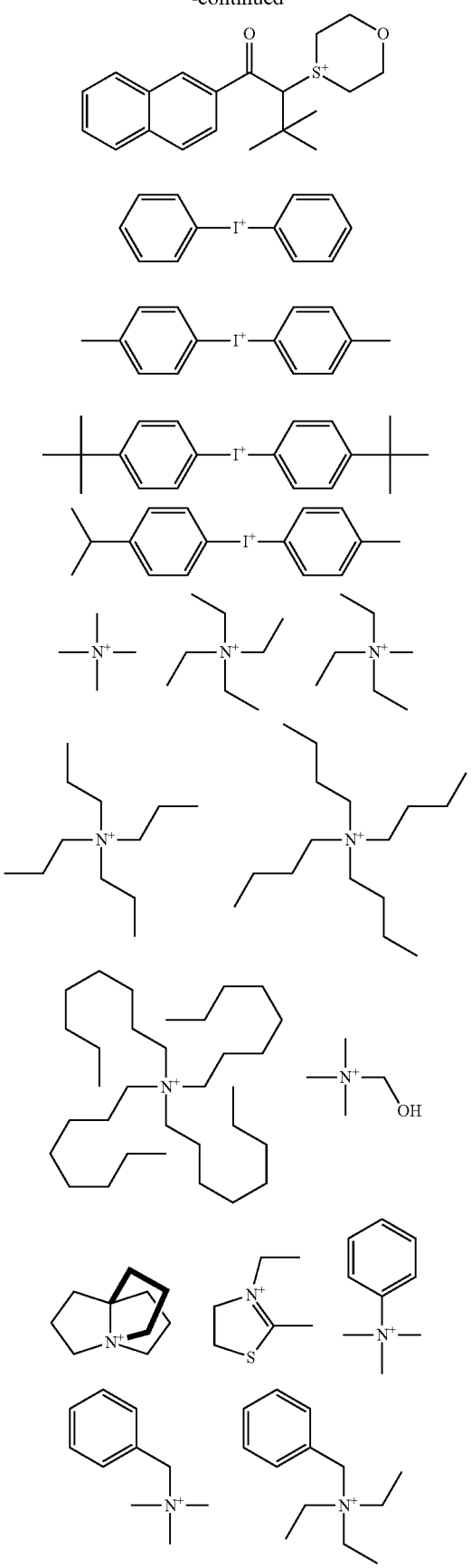

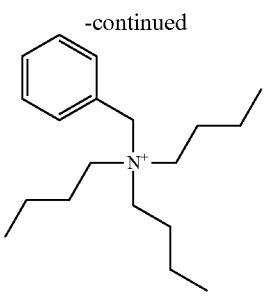

Examples of the onium salt having formula (xa) or (xb) include combinations of anions with cations, both as mentioned above. These onium salts am readily synthesized via ion exchange reaction by any well-known organic chemistry methods. For the ion exchange reaction, reference is made to JP-A 2007-145797, for example.

The onium salt having formula (xa) or (xb) functions as a quencher in the resist composition. This is because the counter anion of the onium salt is a conjugated base of weak acid. As used herein, the weak acid indicates an acidity insufficient to deprotect an acid labile group from an acid labile group-containing unit in the base polymer. The onium salt having formula (xa) or (xb) functions as a quencher when used in combination with an onium salt type photoacid generator having a conjugated base of a strong acid, typically a sulfonic acid which is fluorinated at α-position as the counter anion.

In a system using a mixture of an onium salt capable of generating a strong acid (e.g., α-position fluorinated sulfonic acid) and an onium salt capable of generating a weak acid (e.g., non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If a photoacid generator capable of generating a strong acid is an onium salt, an exchange from the strong acid generated upon exposure to high-energy radiation to a weak acid as above can take place, but it rarely happens that the weak acid generated upon exposure to high-energy radiation collides with the unreacted onium salt capable of generating a strong acid to induce a salt exchange. This is because of a likelihood of an onium cation forming an ion pair with a stronger acid anion.

Also a compound having the formula (xc) is useful as the quencher in the form of an onium salt of weak acid.

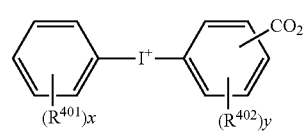

(xc)

In formula (xc), $R^{401}$ and $R^{402}$ are each independently a $C_1$-$C_{12}$ monovalent hydrocarbon group, nitro group, $C_1$-$C_{12}$ alkoxy group, $C_2$-$C_{12}$ acyl group, or $C_2$-$C_{12}$ acyloxy group, x and y are each independently an integer of 0 to 4.

Examples of the compound having formula (xc) are shown below, but not limited thereto.

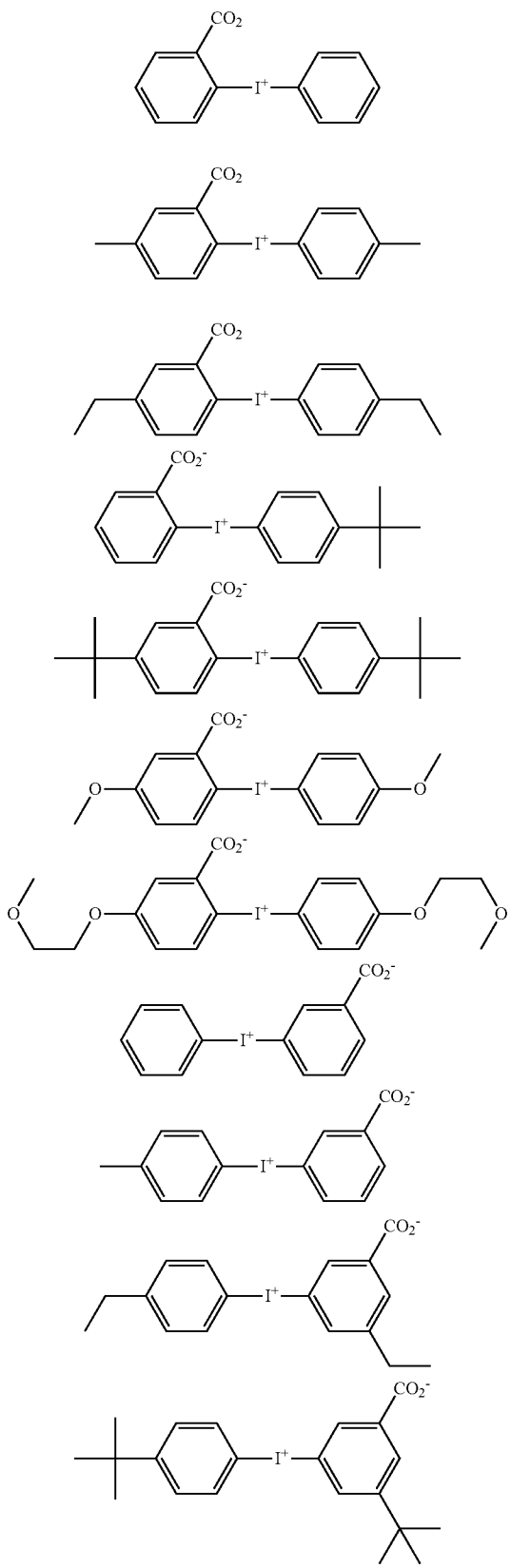

-continued

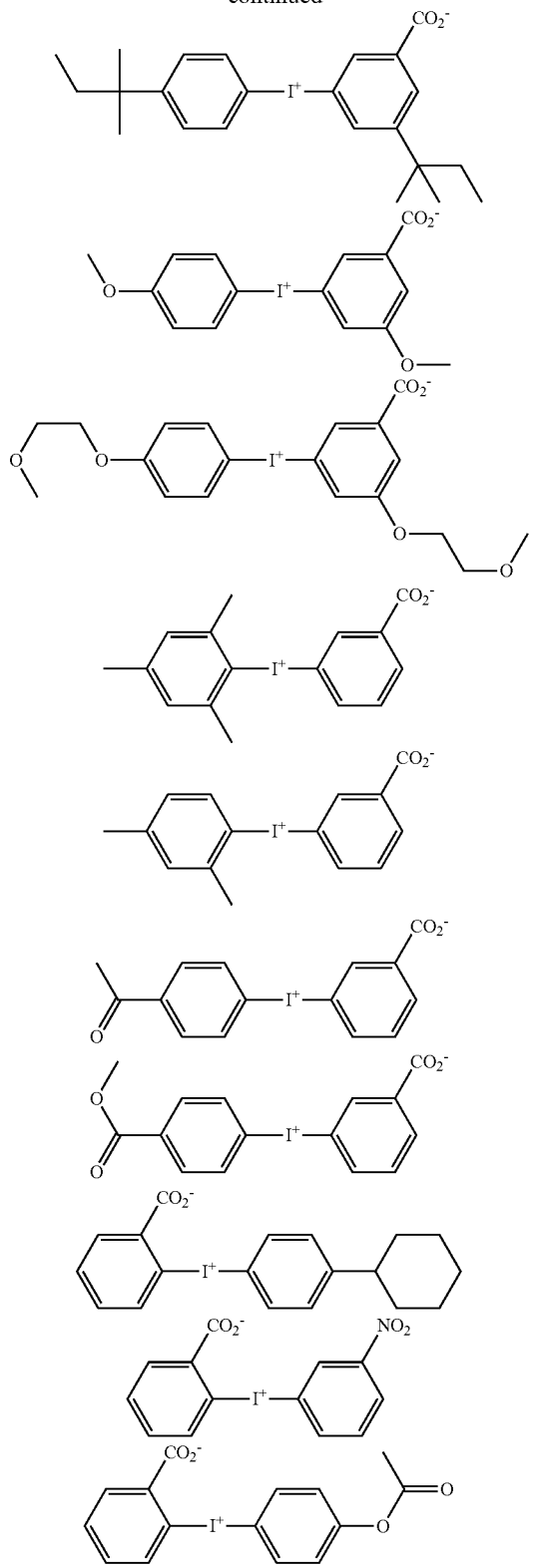

In the resist composition, the quencher is used in an amount of 0 to 100 parts by weight, and when added, preferably 0.001 to 50 parts by weight, per 80 parts by weight of the base polymer. The quencher may be used alone or in admixture.

Other Components

In addition to the foregoing components, the mist composition may comprise other components such as a surfactant, dissolution inhibitor, acetylene alcohol, and water repellency improver, which may be blended in any desired combination for a particular purpose. Suitable surfactants are described in JP-A 2008-111103, paragraphs [0165]-[0166](U.S. Pat. No. 7,537,880). Suitable dissolution inhibitors are described in JP-A 2008-122932, paragraphs [0155]-[0178] (U.S. Pat. No. 7,771,914). Suitable acetylene alcohols are described in JP-A 2008-122932, paragraphs [0179]-[0182] (U.S. Pat. No. 7,771,914).

The dissolution inhibitor is preferably added in an amount of 0 to 50 parts, more preferably 0 to 40 parts by weight per 80 parts by weight of the base polymer. The amounts of the surfactant and acetylene alcohol may be selected appropriate for their purpose.

To the resist composition, a water repellency improver may also be added for improving the water repellency on surface of a resist film as spin coated. The water repellency improver may be used in the topcoatless immersion lithography. Suitable water repellency improvers include compounds of specific structure having a 1,1,1,3,3,3-hexafluoro-2-propanol residue and are described in JP-A 2007-297590, JP-A 2008-111103, JP-A 2008-122932, JP-A 2012-128067, and JP-A 2013-057836.

Suitable water repellency improvers include polymers capable of improving water repellency, preferably polymers consisting of fluorinated units of one type, copolymers consisting of fluorinated units of more than one type, and copolymers consisting of fluorinated units and fluorine-free units.

Examples of the fluorinated units and other units are shown below, but not limited thereto. Herein $R^B$ is hydrogen or methyl.

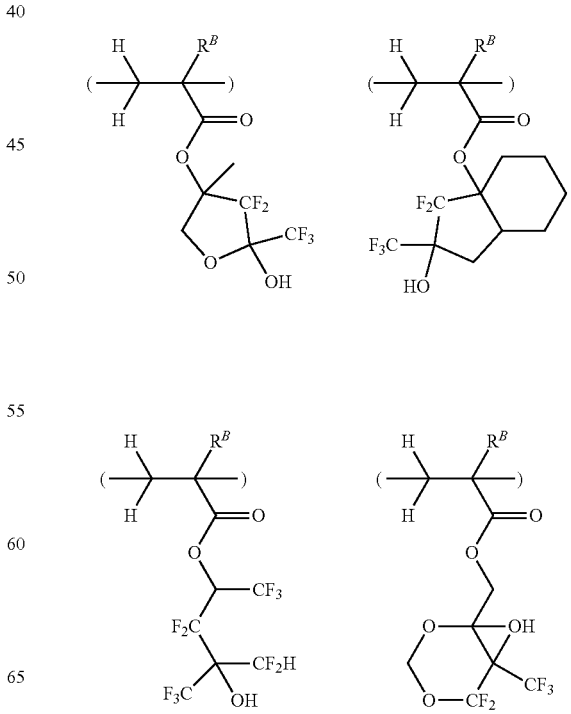

-continued
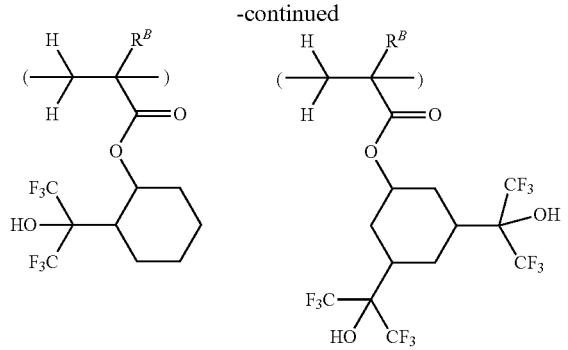
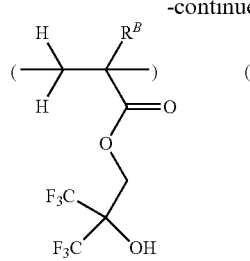
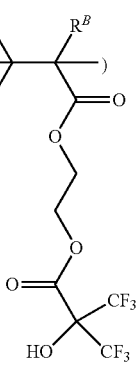
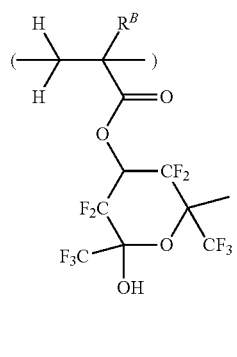
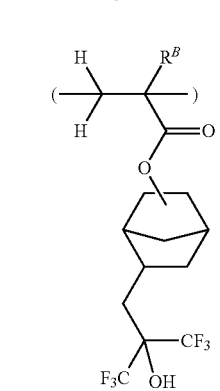
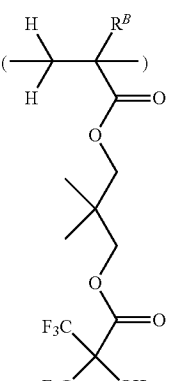
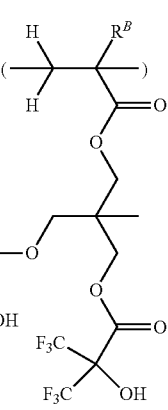
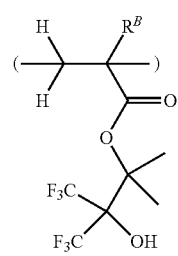
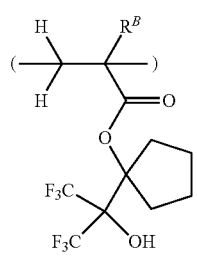
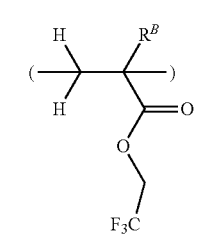
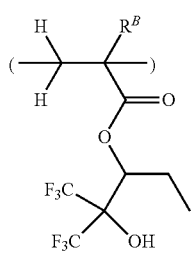
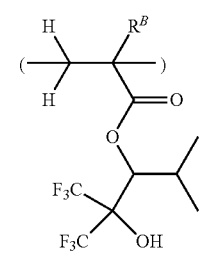
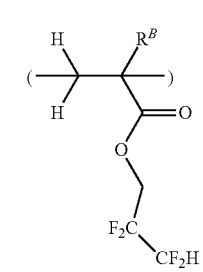
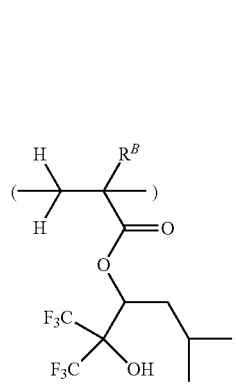
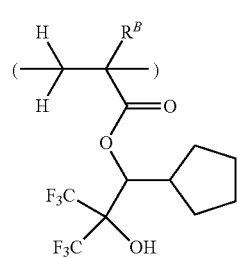
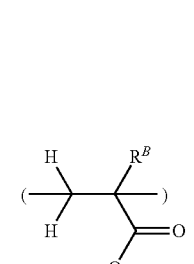
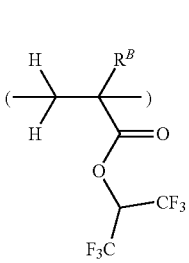
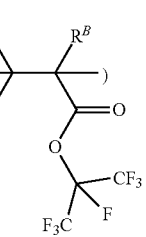

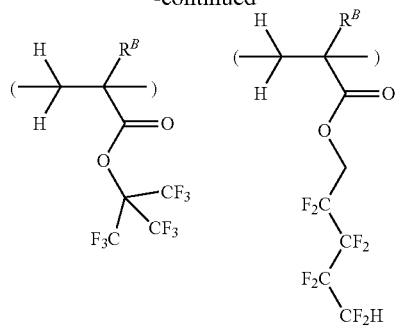
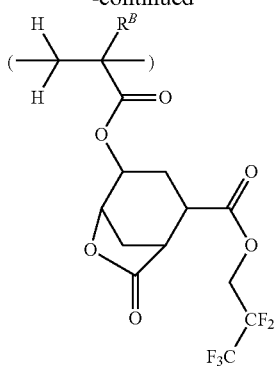
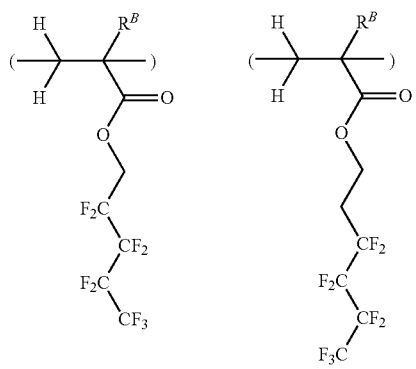
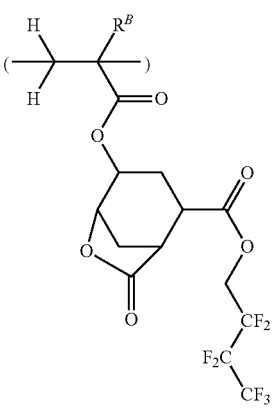
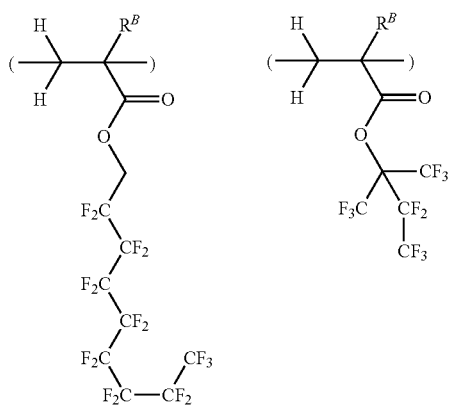
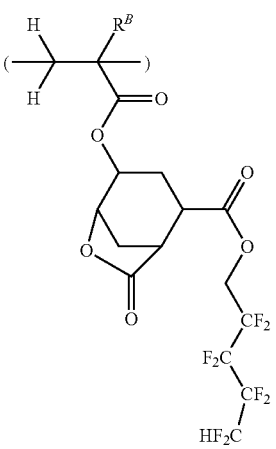
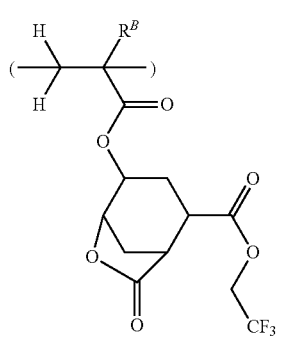
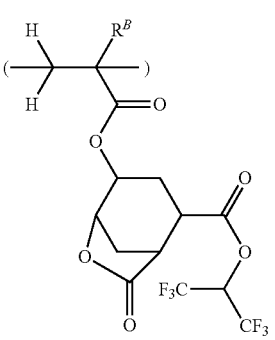

107
-continued
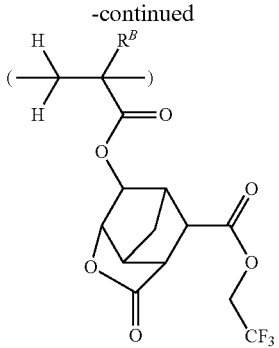
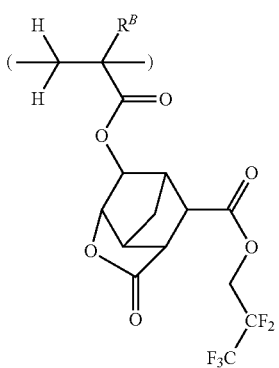
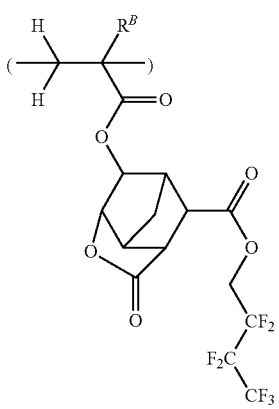
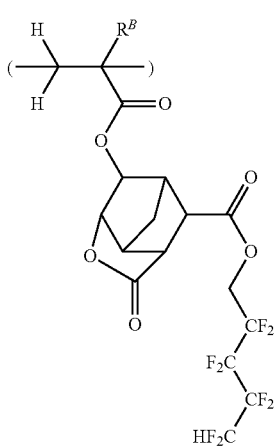
108
-continued
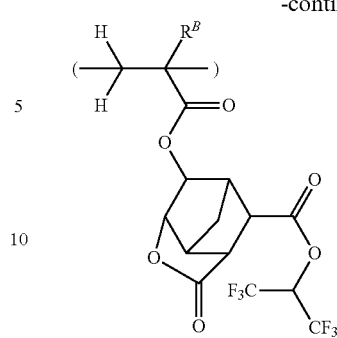
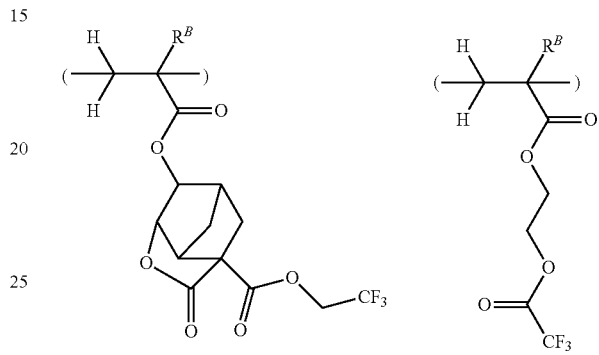
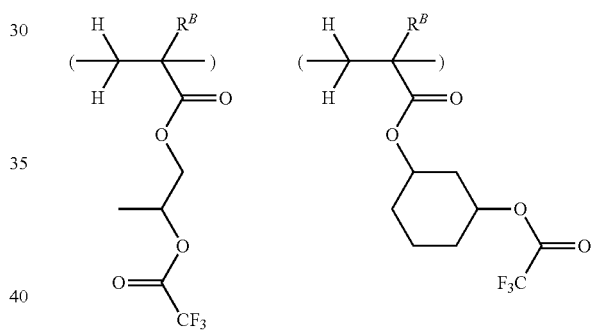
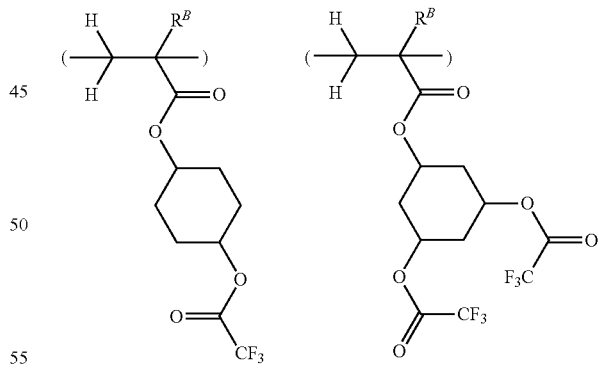
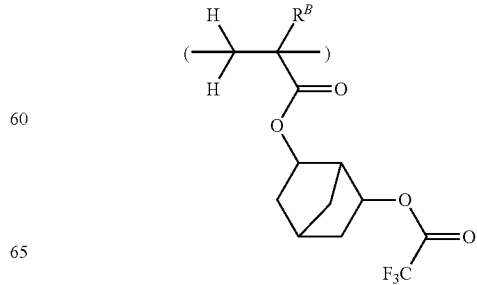

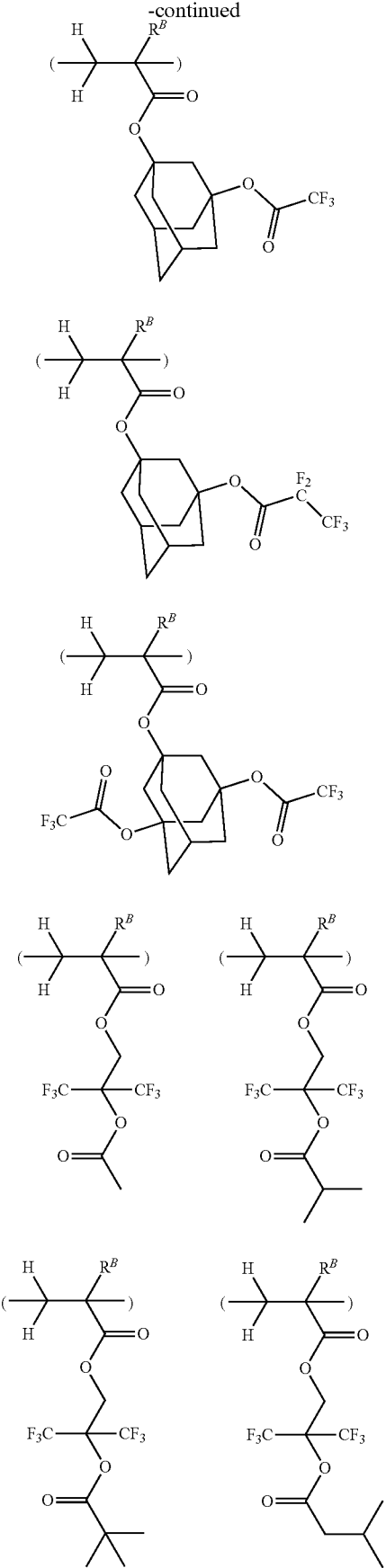
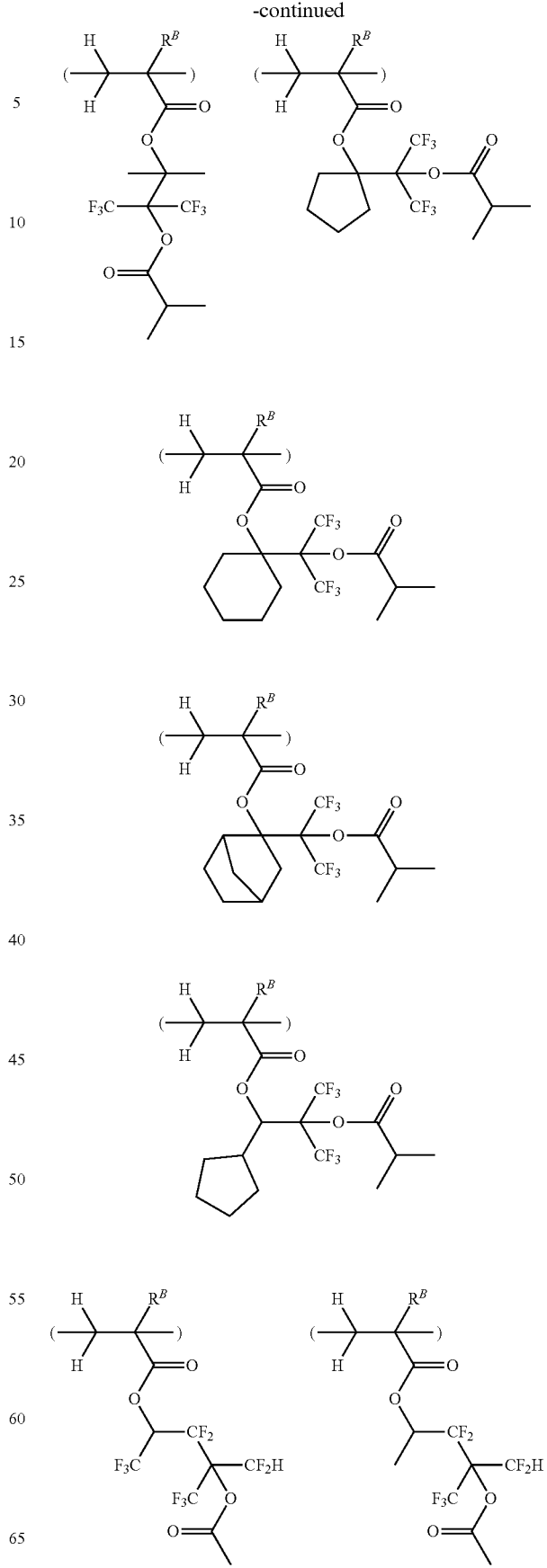

111
-continued
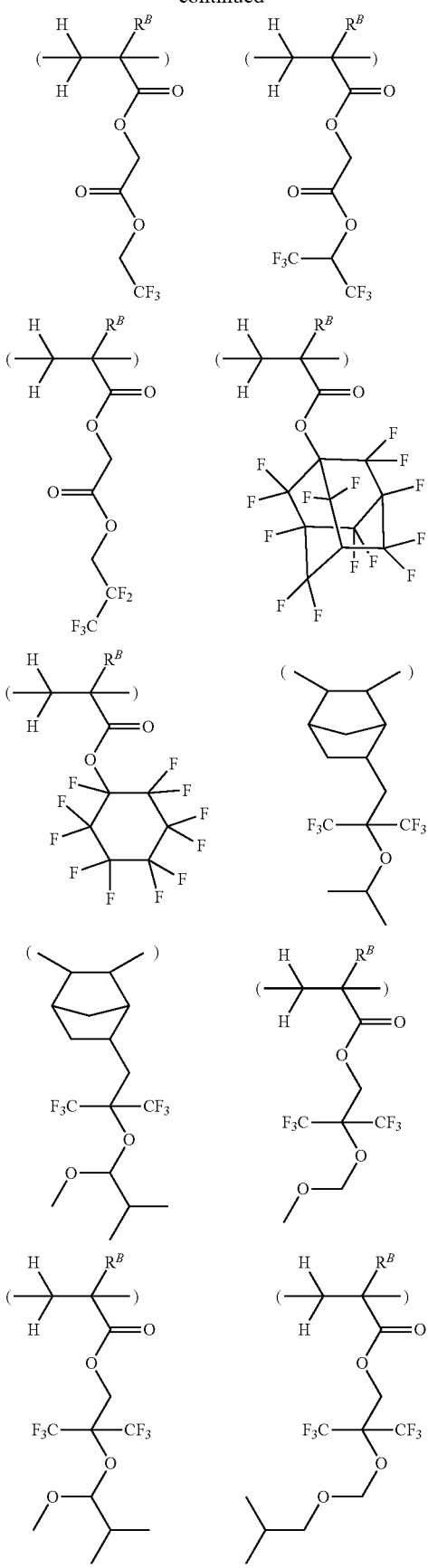
112
-continued
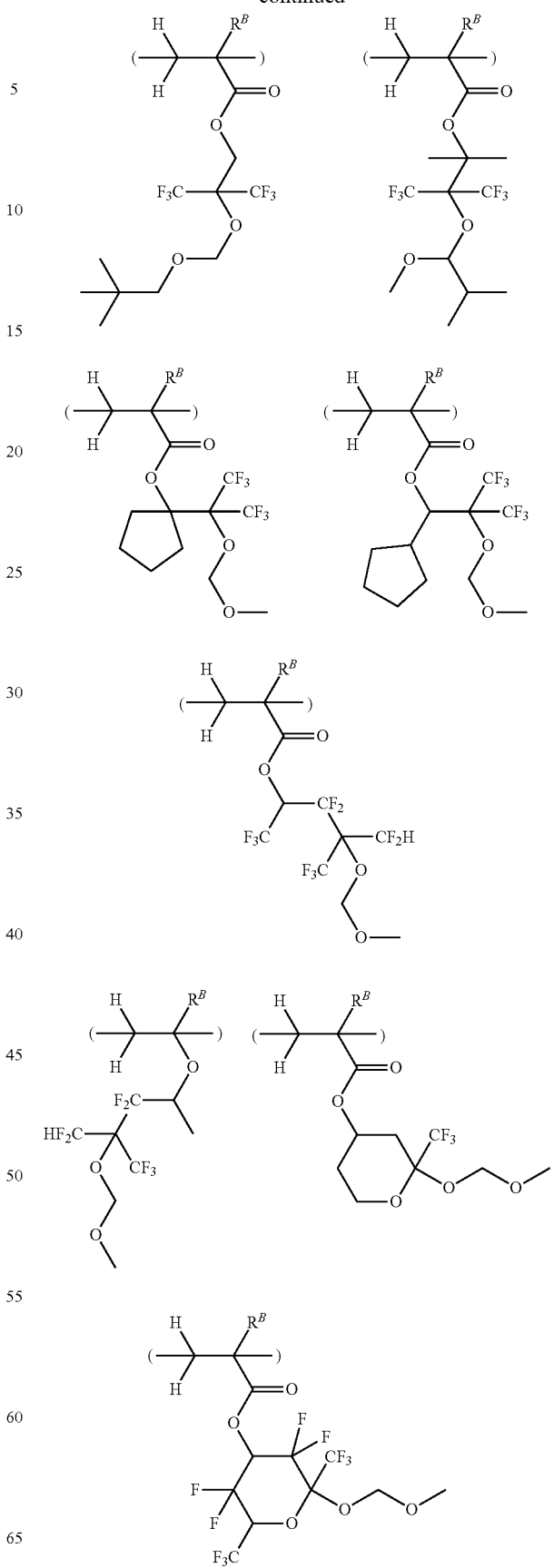

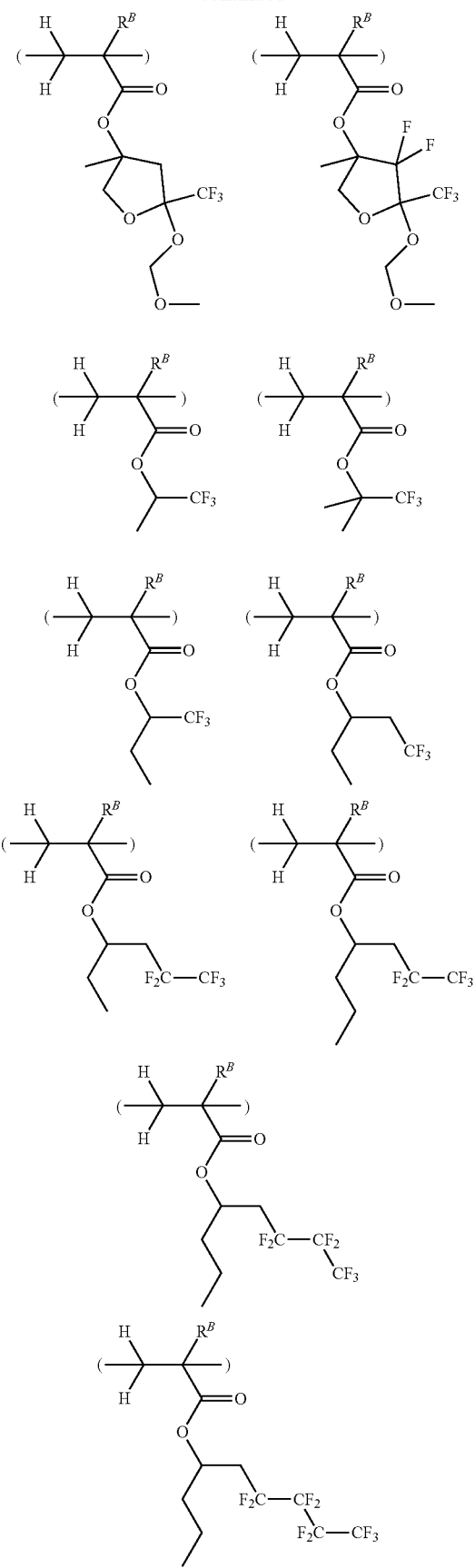
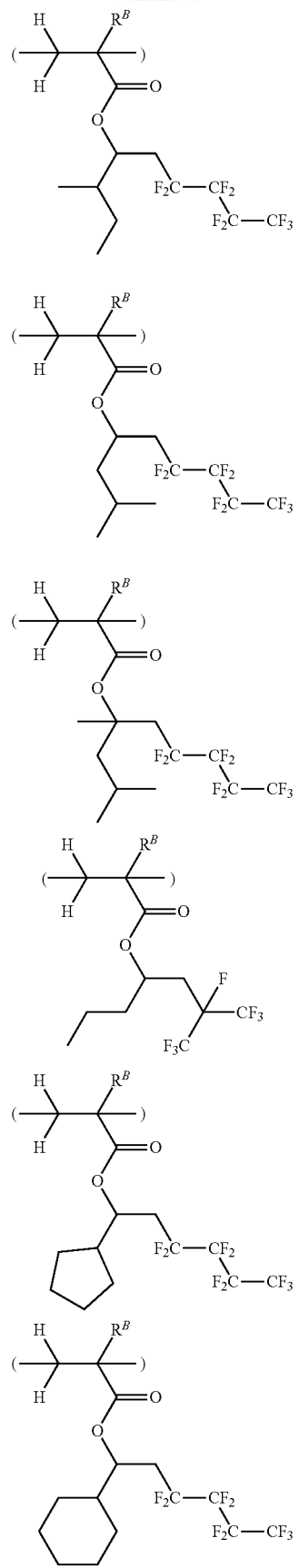

115
-continued
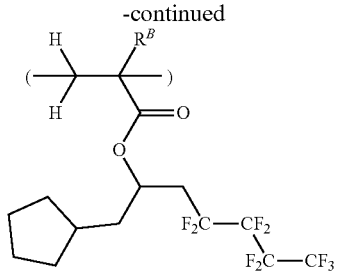
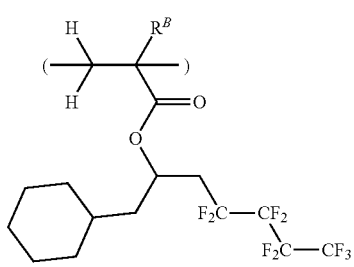
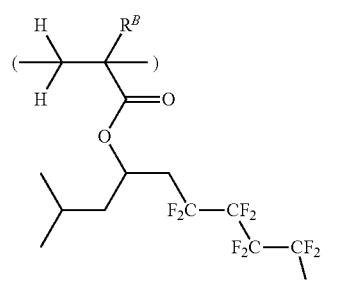
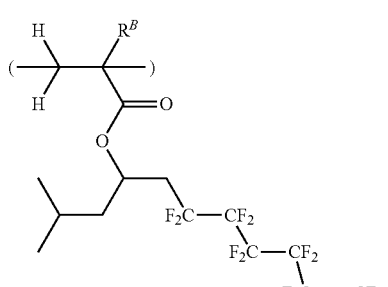
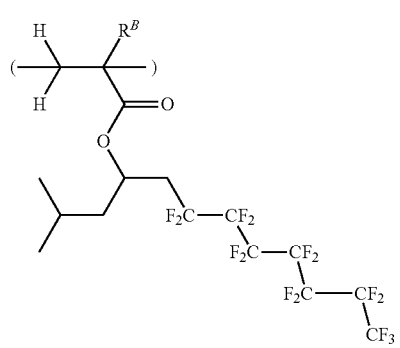
116
-continued
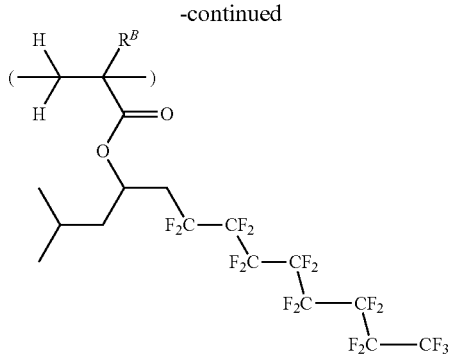
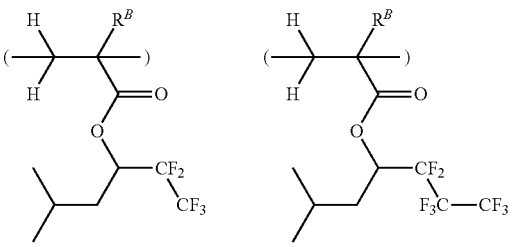
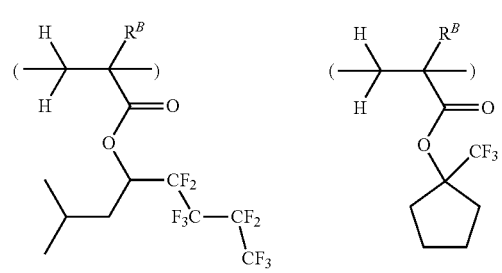
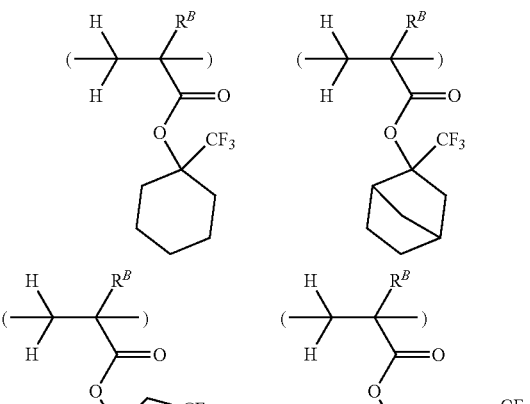
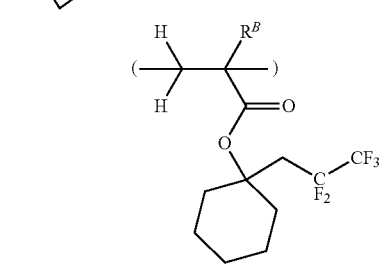

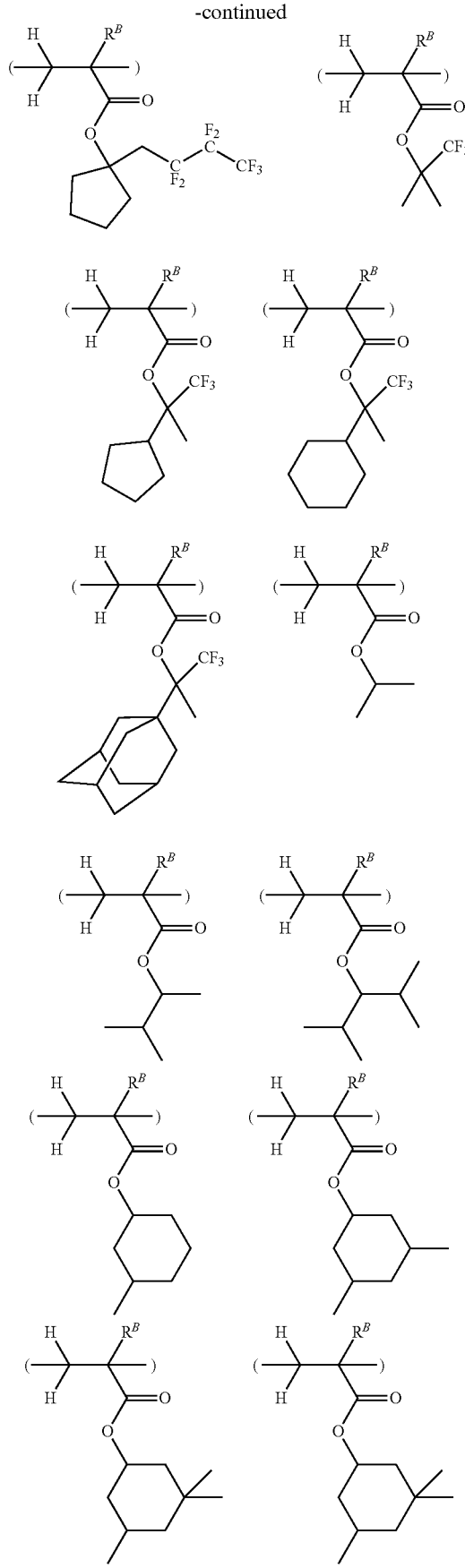
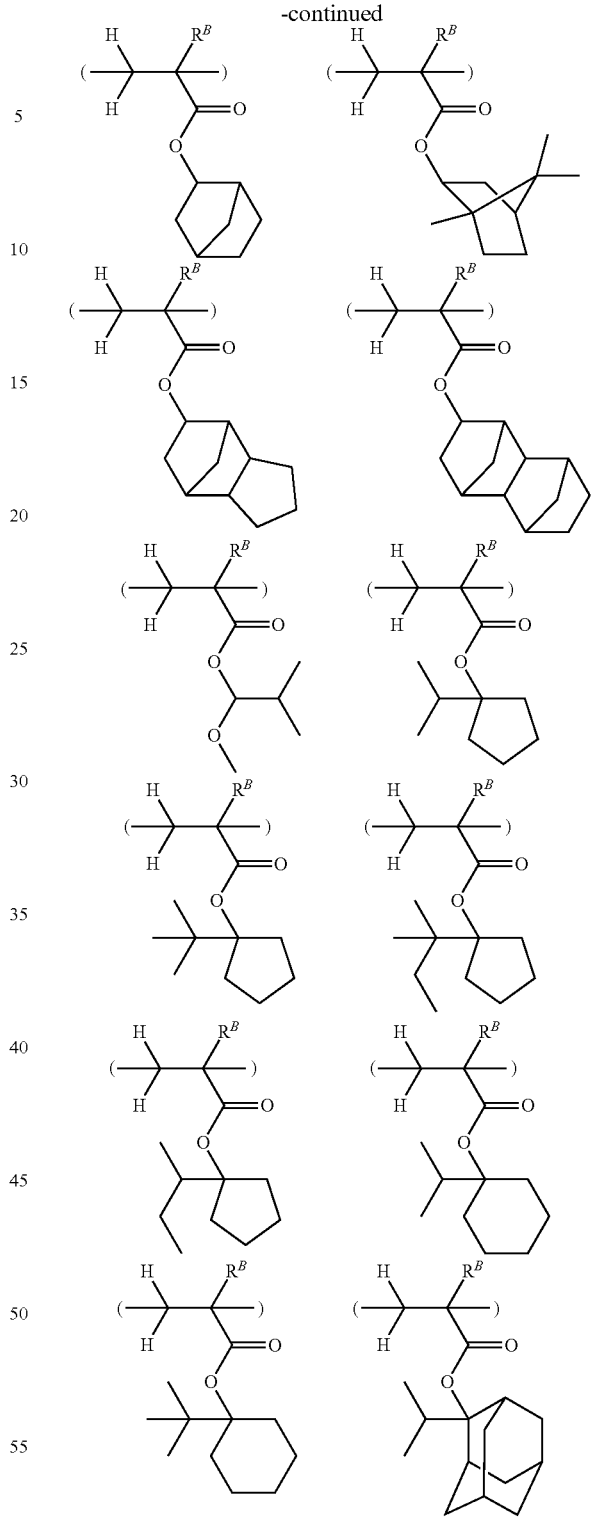

The water repellency improver should be soluble in alkaline aqueous solution as the developer. The water repellency improver having a 1,1,1,3,3,3-hexafluoro-2-propanol residue is well soluble in the developer. A polymer comprising recurring units having an amino group or amine salt serves as the water repellency improver and is effective for preventing evaporation of acid during PEB, thus preventing any opening failure of hole patterns or bridging of line-andspace patterns after development. An appropriate amount of the water repellency improver is 0 to 20 parts, preferably 0.1 to 20 parts, more preferably 0.5 to 10 parts by weight per 80 parts by weight of the base polymer.

Process

A further embodiment of the invention is a pattern forming process comprising the steps of applying the resist composition to form a resist film on a substrate, exposing the resist film to high-energy radiation, and developing the exposed resist film in a developer to form a pattern. If necessary, any additional steps may be added.

For example, the resist composition is first applied onto a substrate on which an integrated circuit is to be formed (e.g., Si, $SiO_2$, SiN, SiON, TiN, WSi, BPSG, SOG, silicon-containing antireflective coating, or multilayer film including organic hydrocarbon film) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hotplate at a temperature of 60 to 150° C. for 10 seconds to 30 minutes, preferably at 80 to 120° C. for 30 seconds to 20 minutes. The resulting resist film is generally 0.01 to 2 µm thick.

The resist film is then exposed to a desired pattern of high-energy radiation such as UV, deep-UV, EB, x-ray, excimer laser light, γ-ray, synchrotron radiation, EUV, or soft x-ray. When UV, deep-UV, x-ray, excimer laser light, γ-ray, synchrotron radiation, EUV or soft x-ray is used as the high-energy radiation, the resist film is exposed thereto through a mask having a desired pattern in a dose of preferably about 1 to 200 $mJ/cm^2$, more preferably about 10 to 100 $mJ/cm^2$. When EB is used as the high-energy radiation, the resist film is exposed thereto through a mask having a desired pattern or directly in a dose of preferably about 0.1 to 100 $\mu C/cm^2$, more preferably about 0.5 to 50 $\mu C/cm^2$. It is appreciated that the inventive resist composition is suited in micropatterning using KrF excimer laser, ArF excimer laser, EB, EUV, x-ray, soft x-ray, γ-ray or synchrotron radiation.

The exposure is generally performed by conventional lithography whereas the immersion lithography of holding a liquid having a refractive index of at least 1.0 between the resist film and a projection lens may also be employed. The liquid is typically water, and in this case, a protective film which is insoluble in water may be formed on the resist film.

While the water-insoluble protective film which is used in the immersion lithography serves to prevent any components from being leached out of the resist film and to improve water sliding on the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

After the exposure, the resist film may be baked (PEB) on a hot plate preferably at 60 to 150° C. for 10 seconds to 30 minutes, more preferably at 80 to 120° C. for 30 seconds to 20 minutes.

After the exposure or PEB, the resist film is developed in a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydride (TPAH), or tetrabutylammonium hydroxide (TBAH). The resist film in the exposed region is dissolved in the developer whereas the resist film in the unexposed region is not dissolved. In this way, the desired positive pattern is formed on the substrate.

In an alternative embodiment using the resist composition, a negative pattern may be formed via organic solvent development. The developer used herein is preferably selected from among 2-octanone, 2-nonanone, 2-heptanone, 3-heptanone, 4-heptanone, 2-hexaone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film may be rinsed with water by standard techniques such as dip, puddle and spray techniques, preferably for 3 seconds to 3 minutes, more preferably 5 seconds to 2 minutes.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLES

Synthesis Examples, Examples and Comparative Examples are given below by way of illustration and not by way of limitation. The abbreviation "pbw" is parts by weight. For all polymers, Mw and Mn axe determined by GPC versus polystyrene standards using tetrahydrofuran (THF) or N,N-dimethylformamide (DMF) solvent.

The monomers used for the preparation of polymers in Examples are shown below.

MA-1

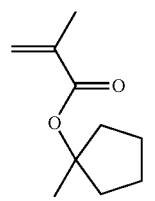

MA-2

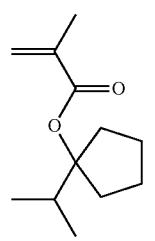

MA-3

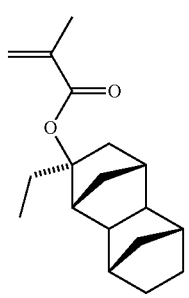

MC-1

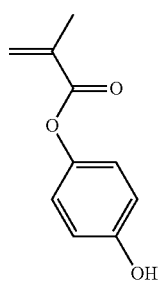

MC-2

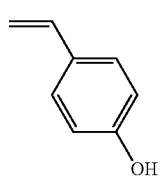

ME-1

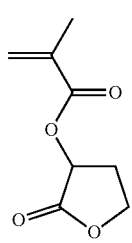

ME-2

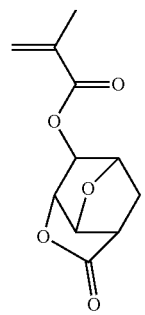

MF-1

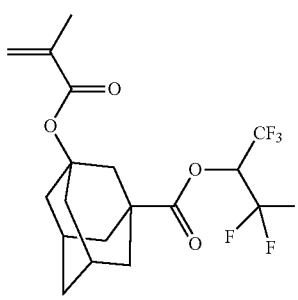

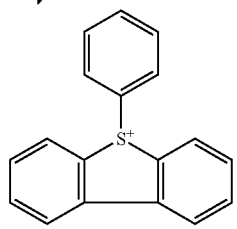

[1] Preparation of Polymers

Synthesis Example 1-1

Preparation of Polymer P-1

Under nitrogen atmosphere, 49.2 g of MA-2, 17.1 g of ME-1, 33.7 g of ME-2, and 5.8 g of dimethyl 2,2'-azobisisobutyrate were dissolved in 175 g of methyl ethyl ketone (MEK). With stirring under nitrogen atmosphere, the resulting solution was added dropwise to 58.3 g of MEK at 80° C. over 4 hours. After the completion of dropwise addition, the polymerization solution was continuously stirred for 2 hours while keeping the temperature of 80° C. The polymerization solution was cooled to room temperature and added dropwise to 1,500 g of hexane. The resulting precipitate was collected by filtration, and vacuum dried at 60° C. for 20 hours, obtaining Polymer P-1 in white solid form (amount 94 g, yield 94%). On $^{13}$C-NMR analysis, Polymer P-1 had a compositional ratio of MA-2/ME-1/ME-2=50/20/30 (molar ratio). On GPC analysis using THF, Polymer P-1 had a Mw of 8,700 and a Mw/Mn of 1.73.

Synthesis Examples 1-2 and 1-3

Synthesis of Polymers P-2 and P-3

Polymers P-2 and P-3 were synthesized by the same procedure as in Synthesis Example 1-1 aside from changing the type and amount of monomers. Polymers P-2 and P-3 were determined for Mw and Mw/Mn by GPC analysis using DMF.

The compositional ratio, Mw and Mw/Mn of Polymers P-1 to P-3 are tabulated in Table 1.

TABLE 1

| Polymer | Unit 1 | Ratio (mol %) | Unit 2 | Ratio (mol %) | Unit 3 | Ratio (mol %) | Unit 4 | Ratio (mol %) | Mw | Mw/Mn |
|---|---|---|---|---|---|---|---|---|---|---|
| P-1 | MA-2 | 50.0 | ME-1 | 20.0 | ME-2 | 30.0 | — | — | 8,700 | 1.73 |
| P-2 | MA-1 | 60.0 | MC-2 | 40.0 | — | — | — | — | 10,000 | 1.68 |
| P-3 | MF-1 | 20.0 | MA-3 | 30.0 | ME-2 | 30.0 | MC-1 | 20.0 | 11,000 | 1.76 |

[2] Preparation of Epoxy Compounds

Example 1-1

Preparation of Epoxy Compound EP-1

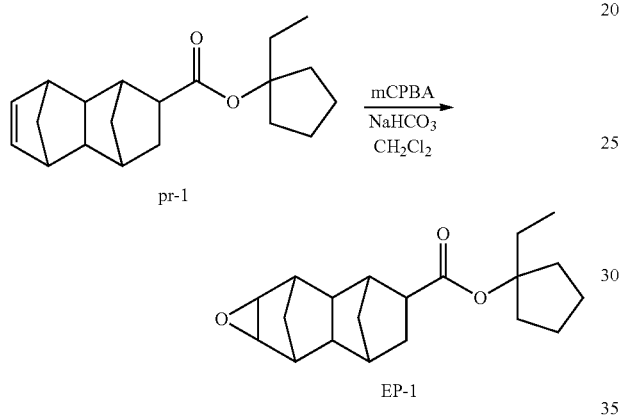

pr-1

EP-1

Under nitrogen atmosphere, 40 g of olefin compound pr-1 was mixed with 18.5 g of sodium hydrogencarbonate and 600 g of dichloromethane to form a suspension, which was ice cooled below 10° C. Below 20° C., 27 g of m-chlorop- erbenzoic acid was added to the suspension over 10 minutes. The solution was stirred at room temperature for 4 hours. After the complete consumption of the olefin compound was confirmed by gas chromatography, the reaction solution was ice cooled again. Below 20° C., an aqueous solution of 37 g of sodium thiosulfate pentahydrate in 500 g of water was added dropwise thereto. At the end of dropwise addition, stirring was continued at room temperature for 2 hours. The solution was combined with 1,000 g of hexane for layer separation. This was followed by consecutive washing with 200 g of water, 200 g of saturated sodium hydrogencarbonate aqueous solution, and 200 g of saturated brine. After the solvent was distilled off in vacuum, the solution was stirred at 80° C. for 2 hours, cooled at room temperature, and distilled in vacuum. There was obtained 37.9 g of epoxy compound EP-1 (yield 90%, boiling point 150° C./10 Pa). The 1H-NMR spectrum of epoxy compound EP-1 is shown in FIG. 1.

Comparative Example 1-1

Preparation of Epoxy Compound EP-X

Figure 2:
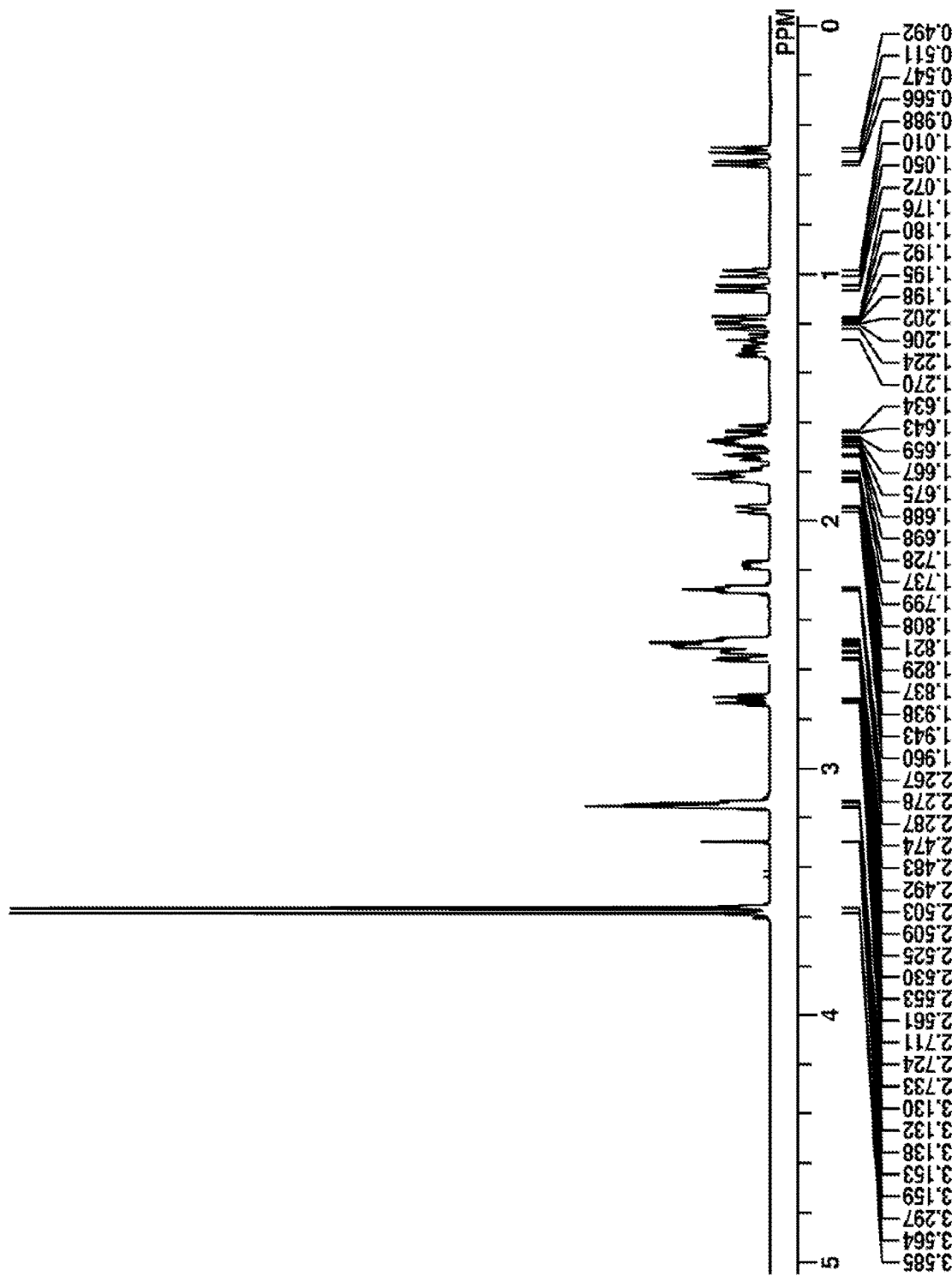
FIG. 2 is a diagram showing the $^1$H-NMR spectrum of epoxy compound EP-X obtained in Comparative Example 1-1.

Epoxy compound EP-X was prepared by the same procedure as in Example 1-1 aside from changing the type of precursor or olefin compound. The $^1$H-NMR spectrum of epoxy compound EP-X is shown in FIG. 2.

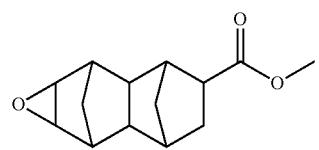

EP-X

Comparative Example 1-2

Preparation of Epoxy Compound EP-Y

Epoxy compound EP-Y was prepared by the same procedure as in Example 1-1 aside from changing the type of precursor or olefin compound.

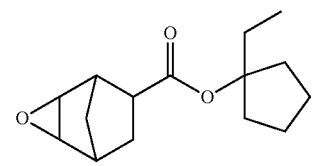

EP-Y

[3] Preparation of Resist Compositions

Examples 2-1 to 2-5 and Comparative Examples 2-1 to 2-6

Resist compositions in solution form were prepared by dissolving Polymer P-1 to P-3, acid generator PAG-1, quencher Q-1 or Q-2, Epoxy compound EP-1, EP-X or EP-Y, and fluorinated polymer SF-1 in a solvent in accordance with the formulation shown in Table 2, and filtering through a Teflon® filter with a pore size of 0.2 μm.

The solvent, acid generator PAG-1, quenchers Q-1, Q-2, and fluorinated polymer SF-1 in Table 2 are identified below.

Solvent

PGMEA: propylene glycol monomethyl ether acetate

GBL: γ-butyrolactone

Acid Generator PAG-1

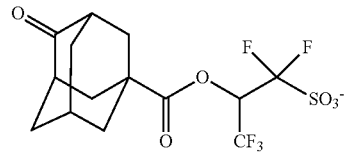

PAG-1

-continued

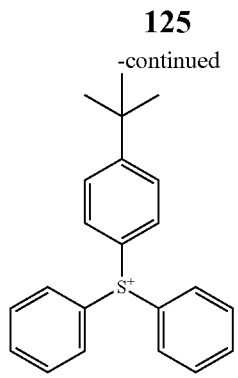

Quenchers Q-1, Q-2

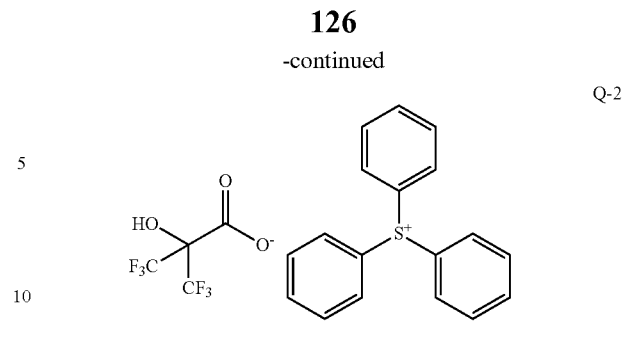

Fluorinated Polymer SF-1

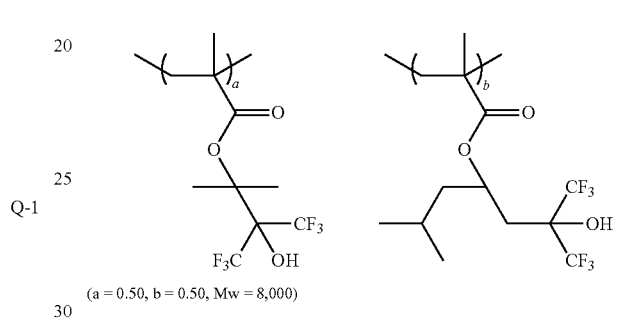

TABLE 2

| | | Resist composition | Polymer (pbw) | Acid generator (pbw) | Quencher (pbw) | Epoxy compound (pbw) | Fluorinated polymer (pbw) | Solvent 1 (pbw) | Solvent 2 (pbw) |
|---|---|---|---|---|---|---|---|---|---|
| Example | 2-1 | R-1 | P-1 (80) | PAG-1 (16.9) | Q-1 (1.2) | EP-1 (2.0) | SF-1 (5) | PGMEA (2,453) | GBL (278) |
| | 2-2 | R-2 | P-1 (80) | PAG-1 (9.8) | Q-2 (4.6) | EP-1 (2.0) | SF-1 (5) | PGMEA (2,453) | GBL (278) |
| | 2-3 | R-3 | P-2 (80) | PAG-1 (42.1) | Q-1 (1.2) | EP-1 (2.0) | — | PGMEA (2,328) | GBL (449) |
| | 2-4 | R-4 | P-2 (80) | PAG-1 (35.1) | Q-2 (7.4) | EP-1 (2.0) | — | PGMEA (2,328) | GBL (449) |
| | 2-5 | R-5 | P-3 (80) | — | Q-2 (5.5) | EP-1 (2.0) | — | PGMEA (2,328) | GBL (449) |
| Comparative Example | 2-1 | CR-1 | P-1 (80) | PAG-1 (16.9) | Q-1 (1.4) | — | SF-1 (5) | PGMEA (2,453) | GBL (278) |
| | 2-2 | CR-2 | P-1 (80) | PAG-1 (9.8) | Q-2 (4.6) | EP-X (2.0) | SF-1 (5) | PGMEA (2,453) | GBL (278) |
| | 2-3 | CR-3 | P-1 (80) | PAG-1 (9.8) | Q-2 (4.6) | EP-Y (2.0) | SF-1 (5) | PGMEA (2,453) | GBL (278) |
| | 2-4 | CR-4 | P-2 (80) | PAG-1 (35.1) | Q-2 (9.2) | — | — | PGMEA (2,328) | GBL (449) |
| | 2-5 | CR-5 | P-2 (80) | PAG-1 (35.1) | Q-2 (7.4) | EP-X (2.0) | — | PGMEA (2,328) | GBL (449) |
| | 2-6 | CR-6 | P-3 (80) | — | Q-2 (5.5) | EP-Y (2.0) | — | PGMEA (2,328) | GBL (449) |

[4] ArF Lithography Patterning Test 1

Examples 3-1 to 3-2 and Comparative Examples 3-1 to 3-3

On a silicon substrate, an antireflective coating solution (ARC29A, Nissan Chemical Corp.) was coated and baked at 180° C. for 60 seconds to form an ARC of 100 nm thick. Each of the resist compositions (R-1, R-2, CR-1 to CR-3) was spin coated onto the ARC and prebaked on a hotplate at 100° C. for 60 seconds to form a resist film of 90 nm thick on the ARC. Using an ArF excimer laser scanner (NSR-S610C by Nikon Corp., NA 1.30, σ 0.94/0.74, 4/5 annular illumination, 6% halftone phase shift mask), the resist film was exposed by the immersion lithography. The immersion liquid used herein was water. Thereafter, the resist film was baked (PEB) at 85° C. for 60 seconds and developed in a 2.38 wt % TMAH aqueous solution for 60 seconds, forming a line-and-space (L/S) pattern.

The L/S pattern was evaluated for sensitivity, LWR, and DOF by the following methods. The pattern of line width 52 nm and pitch 104 nm was observed under an electron microscope. The optimum dose Eop is the dose (mJ/cm$^2$) at which a line width of 45 nm is finished, and reported as a sensitivity. On a L/S pattern printed at the optimum dose Eop, the space width is measured at longitudinally spaced apart 10 points, from which a 3-fold value (3σ) of standard deviation (σ) is determined and reported as LWR. A smaller value of 3σ indicates a pattern having a lower roughness and more uniform space width. Exposure was performed at Eop while shifting the focus up and down. A range (nm) of focus within which a L/S pattern was resolved to a size of 45 nm±10% (i.e., 40.5 to 49.5 nm) was determined and reported as DOF. A greater value indicates a wider margin relative to focus shifts, i.e., better performance.

The results are shown in Table 3.

TABLE 3

| | | Resist composition | Sensitivity (mJ/cm$^2$) | DOF (nm) | LWR (nm) |
|---|---|---|---|---|---|
| Example | 3-1 | R-1 | 32 | 100 | 3.4 |
| | 3-2 | R-2 | 36 | 90 | 2.9 |
| Comparative | 3-1 | CR-1 | 38 | 70 | 4.0 |
| Example | 3-2 | CR-2 | 45 | 60 | 3.7 |
| | 3-3 | CR-3 | 36 | 60 | 3.8 |

As is evident from Table 3, the resist compositions containing epoxy compounds within the scope of the invention exhibit improved values of LWR. The inventive resist compositions show a good balance of sensitivity and LWR without sacrificing sensitivity, as compared with the cases where the amount of quencher is increased, an epoxy compound having lower molecular weight is added, and an epoxy compound free of an acid labile group is added.

[5] EB Lithography Test

Examples 4-1 to 4-3 and Comparative Examples 4-1 to 4-3

An antireflective coating solution (DUV-42, Nissan Chemical Corp.) was coated on a silicon substrate and baked at 200° C. for 60 seconds to form an ARC of 61 nm thick. Each of the resist compositions (R-3 to R-5, CR-4 to CR-6) was spin coated onto the ARC and prebaked on a hotplate at 100° C. for 60 seconds to form a resist film of 45 nm thick. Using an EB lithography system ELS-F125 (Elionix Co., Ltd., accelerating voltage 125 kV), the resist film was exposed to EB through a mask bearing a contact hole (CH) pattern with a hole size of 24 nm and a pitch of 48 nm (on-wafer size) while varying the dose from 50 μC/cm$^2$ at a step of 1 μC/m$^2$. The resist film was baked (PEB) at the temperature shown in Table 4 for 60 seconds. The resist film was then puddle developed in a 2.38 wt % TMAH aqueous solution for 30 seconds, rinsed with deionized water, and spin dried, yielding a positive resist pattern.

The CH pattern was observed under CD-SEM S9380 (Hitachi High Technologies Corp.) whereupon sensitivity and CDU were evaluated by the following methods. The optimum dose Eop was the dose (μC/cm$^2$) which provided a CH pattern with a hole size of 24 nm and a pitch of 48 nm, and reported as a sensitivity. A smaller dose value indicates a higher sensitivity. For the CH pattern formed by exposure at Eop, the hole size was measured at 10 areas subject to an identical dose of shot (9 contact holes per area), from which a 3-fold value (3σ) of standard deviation (σ) was determined and reported as CDU. A smaller value of 3σ indicates a CH pattern having improved CDU.

The results are shown in Table 4.

TABLE 4

| | | Resist composition | Sensitivity (μC/cm$^2$) | CDU (nm) |
|---|---|---|---|---|
| Example | 4-1 | R-3 | 180 | 3.5 |
| | 4-2 | R-4 | 155 | 3.3 |
| | 4-3 | R-5 | 143 | 3.1 |
| Comparative | 4-1 | CR-4 | 200 | 4.0 |
| Example | 4-2 | CR-5 | 190 | 4.2 |
| | 4-3 | CR-6 | 145 | 3.9 |

As is evident from Table 4, the resist compositions containing epoxy compounds within the scope of the invention exhibit a good balance of sensitivity and CDU when patterns are formed by the EB lithography.

Japanese Patent Application No. 2019-040260 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An epoxy compound having the formula (1):

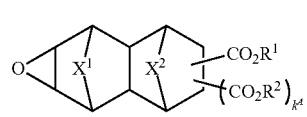

wherein $X^1$ and $X^2$ are each independently —CH$_2$— or —O—, $k^4$ is 0 or 1, $R^1$ and $R^2$ are each independently a C$_4$-C$_{20}$ tertiary hydrocarbon group or a group selected from the following:

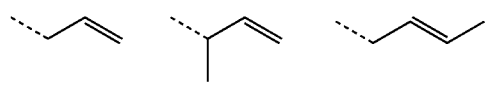

-continued

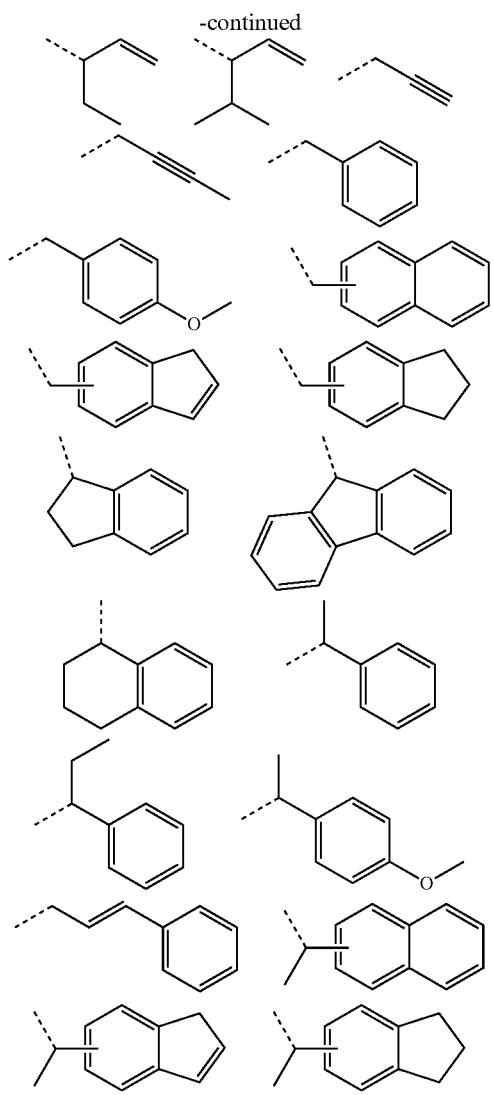

wherein the broken line denotes a valence bond.

2. A resist composition comprising the epoxy compound of claim 1, a base polymer, an acid generator, and an organic solvent, the base polymer comprising reaming units adapted to a polarity switch under the action of acid and recurring units of at least one type selected from the formulae (B) to (E):

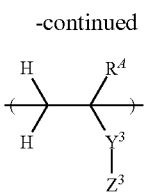 (B)

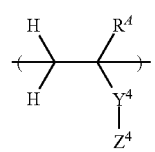 (C)

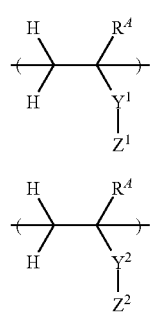

-continued (D)

(E)

wherein $R^A$ is hydrogen, fluorine, methyl or trifluoromethyl, $Z^1$ is a $C_1$-$C_{20}$ fluoroalcohol-containing substituent group, $Z^2$ is a $C_1$-$C_{20}$ phenolic hydroxyl-containing substituent group, $Z^3$ is a $C_1$-$C_{20}$ carboxyl-containing substituent group, $Z^4$ is a substituent group containing lactone skeleton, sultone skeleton, carbonate skeleton, cyclic ether skeleton, acid anhydride skeleton, alcoholic hydroxyl moiety, alkoxycarbonyl moiety, sulfonamide moiety, or carbamoyl moiety, $Y^1$ to $Y^4$ are each independently a single bond, methylene, ethylene, phenylene, fluorinated phenylene, naphthylene, —O—$Y^5$—, —C(=O)—O—$Y^5$—, or —C(=O)—NH—$Y^5$—, $Y^5$ is a $C_1$-$C_6$ alkanediyl, $C_2$-$C_6$ alkenediyl, phenylene or naphthylene group, which may contain a carbonyl moiety, ester bond, ether bond or hydroxyl moiety.

3. The resist composition of claim 2 wherein the base polymer further comprises recurring units of at least one type selected from the formulae (F1) to (F4):

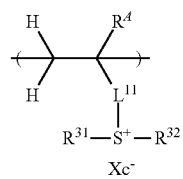 (F1)

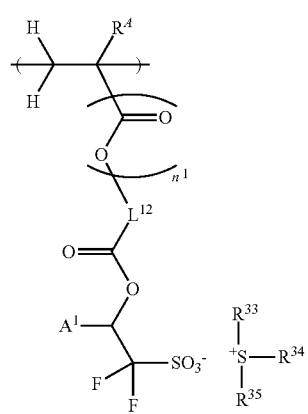 (F2)

(F3)

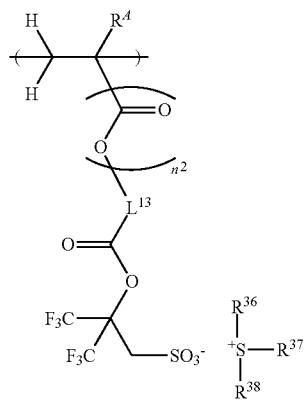

(F4)

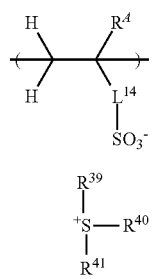

wherein $R^A$ is hydrogen, fluorine, methyl or trifluoromethyl, $L^{11}$ is a single bond, phenylene, —O-$L^{11A}$-, —C(=O)—O-$L^{11A}$-, or —C(=O)NH-$L^{11A}$-, $L^{11A}$ is a $C_1$-$C_{20}$ alkanediyl, $C_2$-$C_{20}$ alkenediyl, or phenylene group which may contain a heteroatom, $L^{12}$ and $L^{13}$ are each independently a single bond or a $C_1$-$C_{20}$ divalent hydrocarbon group which may contain a heteroatom, $L^{14}$ is a single bond, methylene, ethylene, phenylene, fluorinated phenylene, —O-$L^{14A}$-, —C(=O)—O-$L^{14A}$-, or —C(=O)—NH-$L^{14A}$-, $L^{14A}$ is an optionally substituted phenylene group, $R^{31}$ to $R^{41}$ are each independently a $C_1$-$C_{20}$ monovalent hydrocarbon group which may contain a heteroatom, any two of $L^{11}$, $R^{31}$ and $R^{32}$ may bond together to form a ring with the sulfur atom to which they are attached, any two of $R^{33}$, $R^{34}$ and $R^{35}$, any two of $R^{36}$, $R^{37}$ and $R^{38}$, or any two of $R^{39}$, $R^{40}$ and $R^{41}$ may bond together to form a ring with the sulfur atom to which they are attached, $Xc^-$ is a non-nucleophilic counter ion, $A^1$ is hydrogen or trifluoromethyl, $n^1$ is 0 or 1, $n^1$ is 0 when $L^{12}$ is a single bond, $n^2$ is 0 or 1, $n^2$ is 0 when $L^{13}$ is a single bond.

4. A pattern forming process comprising the steps of applying the resist composition of claim 2 to form a resist film on a substrate, exposing the resist film to high-energy radiation, and developing the exposed resist film in a developer.

5. The process of claim 4 wherein an alkaline aqueous solution is used as the developer in the developing step to form a positive pattern wherein the exposed region of film is dissolved and the unexposed region of film is not dissolved.

6. The process of claim 4 wherein an organic solvent is used as the developer in the developing step to form a negative pattern wherein the unexposed region of film is dissolved and the exposed region of film is not dissolved.

7. A resist composition comprising the epoxy compound of claim 1, a base polymer, and an organic solvent, the base polymer comprising recurring units adapted to a polarity switch under the action of acid, recurring units of at least one type selected from the formulae (B) to (E), and recurring units of at least one type selected from the formulae (F1) to (F4):

(B)

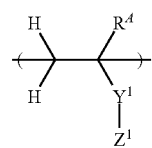

(C)

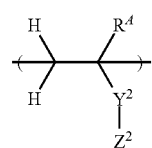

(D)

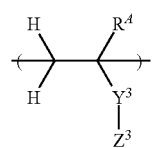

(E)

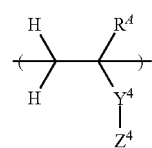

wherein $R^A$ is hydrogen, fluorine, methyl or trifluoromethyl, $Z^1$ is a $C_1$-$C_{20}$ fluoroalcohol-containing substituent group, $Z^2$ is a $C_1$-$C_{20}$ phenolic hydroxyl-containing substituent group, $Z^3$ is a $C_1$-$C_{20}$ carboxyl-containing substituent group, $Z^4$ is a substituent group containing lactone skeleton, sultone skeleton, carbonate skeleton, cyclic ether skeleton, acid anhydride skeleton, alcoholic hydroxyl moiety, alkoxycarbonyl moiety, sulfonamide moiety, or carbamoyl moiety, $Y^1$ to $Y^4$ are each independently a single bond, methylene, ethylene, phenylene, fluorinated phenylene, naphthylene, —O—$Y^5$—, —C(=O)—O—$Y^5$—, or —C(=O)—NH—$Y^5$—, $Y^5$ is a $C_1$-$C_6$ alkanediyl, $C_2$-$C_6$ alkenediyl, phenylene or naphthylene group, which may contain a carbonyl moiety, ester bond, ether bond or hydroxyl moiety, (F1)

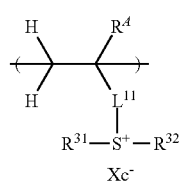

wherein $R^A$ is hydrogen, fluorine, methyl or trifluoromethyl, $L^{11}$ is a single bond, phenylene, —O-$L^{11A}$-, —C(=O)—O-$L^{11A}$-, or —C(=O)NH-$L^{11A}$-, $L^{11A}$ is a $C_1$-$C_{20}$ alkanediyl, $C_2$-$C_{20}$ alkenediyl, or phenylene group which may contain a heteroatom, $L^{12}$ and $L^{13}$ are each independently a single bond or a $C_1$-$C_{20}$ divalent hydrocarbon group which may contain a heteroatom, $L^{14}$ is a single bond, methylene, ethylene, phenylene, fluorinated phenylene, —O-$L^{14A}$-, —C(=O)—O-$L^{14A}$-, or —C(=O)—NH-$L^{14A}$-, $L^{14A}$ is an optionally substituted phenylene group, $R^{31}$ to $R^{41}$ are each independently a $C_1$-$C_{20}$ monovalent hydrocarbon group which may contain a heteroatom, any two of $L^{11}$, $R^{31}$ and $R^{32}$ may bond together to form a ring with the sulfur atom to which they are attached, any two of $R^{33}$, $R^{34}$ and $R^{35}$, any two of $R^{36}$, $R^{37}$ and $R^{38}$, or any two of $R^{39}$, $R^{40}$ and $R^{41}$ may bond together to form a ring with the sulfur atom to which they are attached, $Xc^-$ is a non-nucleophilic counter ion, $A^1$ is hydrogen or trifluoromethyl, $n^1$ is 0 or 1, $n^1$ is 0 when $L^{12}$ is a single bond, $n^2$ is 0 or 1, $n^2$ is 0 when $L^{13}$ is a single bond.

\* \* \* \* \*